United States Patent
Al-Ali et al.

(10) Patent No.: US 10,226,187 B2
(45) Date of Patent: Mar. 12, 2019

(54) PATIENT-WORN WIRELESS PHYSIOLOGICAL SENSOR

(71) Applicant: Masimo Corporation, Irvine, CA (US)

(72) Inventors: Ammar Al-Ali, San Juan Capistrano, CA (US); Kevin Forrest, Rancho Santa Margarita, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 15/253,536

(22) Filed: Aug. 31, 2016

(65) Prior Publication Data

US 2017/0055851 A1    Mar. 2, 2017

Related U.S. Application Data

(60) Provisional application No. 62/212,467, filed on Aug. 31, 2015, provisional application No. 62/212,472, (Continued)

(51) Int. Cl.
*A61B 5/02* (2006.01)
*A61B 5/0205* (2006.01)
(Continued)

(52) U.S. Cl.
CPC .......... *A61B 5/02055* (2013.01); *A61B 5/002* (2013.01); *A61B 5/0004* (2013.01); (Continued)

(58) Field of Classification Search
CPC .... A61B 2562/0219; A61B 2562/0402; A61B 2562/0408; A61B 2562/1117; A61B 2562/6801
See application file for complete search history.

(56) References Cited

U.S. PATENT DOCUMENTS 3,646,606 A    2/1972    Buxton et al.
3,690,313 A    9/1972    Weppner et al.
(Continued)

FOREIGN PATENT DOCUMENTS

EP    0 735 499    10/1996
EP    2 335 569    6/2011
(Continued)

OTHER PUBLICATIONS

US 8,845,543, 09/2014, Diab et al. (withdrawn)
(Continued)

*Primary Examiner* — Puya Agahi
(74) *Attorney, Agent, or Firm* — Knobbe, Martens, Olson & Bear, LLP

(57) ABSTRACT

A wireless, patient-worn, physiological sensor configured to, among other things, help manage a patient that is at risk of forming one or more pressure ulcers is disclosed. According to an embodiment, the sensor includes a base having a top surface and a bottom surface. The sensor also includes a substrate layer including conductive tracks and connection pads, a top side, and a bottom side, where the bottom side of the substrate layer is disposed above the top side of the base. Mounted on the substrate layer are a processor, a data storage device, a wireless transceiver, an accelerometer, and a battery. In use, the sensor senses a patient's motion and wirelessly transmits information indicative of the sensed motion to, for example, a patient monitor. The patient monitor receives, stores, and processes the transmitted information.

11 Claims, 28 Drawing Sheets

Related U.S. Application Data filed on Aug. 31, 2015, provisional application No. 62/212,484, filed on Aug. 31, 2015, provisional application No. 62/212,480, filed on Aug. 31, 2015.

(51) Int. Cl.

| | | |
|---|---|---|
| *A61B 5/0408* | (2006.01) | |
| *A61B 5/11* | (2006.01) | |
| *A61B 5/113* | (2006.01) | |
| *A61B 5/00* | (2006.01) | |
| *A61B 5/05* | (2006.01) | |
| *A61B 5/053* | (2006.01) | |
| *A61B 5/1455* | (2006.01) | |
| *A61B 5/01* | (2006.01) | |
| *A61B 5/0402* | (2006.01) | |
| *G06F 19/00* | (2018.01) | |
| *A61G 7/057* | (2006.01) | |
| *A61B 5/08* | (2006.01) | |

(52) U.S. Cl.
CPC .......... *A61B 5/0015* (2013.01); *A61B 5/0022* (2013.01); *A61B 5/01* (2013.01); *A61B 5/0205* (2013.01); *A61B 5/0402* (2013.01); *A61B 5/0408* (2013.01); *A61B 5/05* (2013.01); *A61B 5/053* (2013.01); *A61B 5/113* (2013.01); *A61B 5/1113* (2013.01); *A61B 5/1116* (2013.01); *A61B 5/1117* (2013.01); *A61B 5/1118* (2013.01); *A61B 5/1121* (2013.01); *A61B 5/1126* (2013.01); *A61B 5/14552* (2013.01); *A61B 5/447* (2013.01); *A61B 5/6801* (2013.01); *A61B 5/6833* (2013.01); *A61B 5/7264* (2013.01); *A61B 5/7275* (2013.01); *A61B 5/7282* (2013.01); *A61B 5/742* (2013.01); *A61B 5/743* (2013.01); *A61B 5/746* (2013.01); *G06F 19/00* (2013.01); *A61B 5/0816* (2013.01); *A61B 5/14551* (2013.01); *A61B 2560/0475* (2013.01); *A61B 2562/0204* (2013.01); *A61B 2562/029* (2013.01); *A61B 2562/0219* (2013.01); *A61B 2562/0223* (2013.01); *A61B 2562/0271* (2013.01); *A61G 7/057* (2013.01); *A61G 2203/32* (2013.01); *A61G 2203/36* (2013.01); *A61G 2203/42* (2013.01); *A61G 2203/46* (2013.01)

(56) References Cited

U.S. PATENT DOCUMENTS

| | | |
|---|---|---|
| 3,978,849 A | 9/1976 | Geneen |
| 4,108,166 A | 8/1978 | Schmid |
| 4,129,125 A | 12/1978 | Lester et al. |
| 4,231,354 A | 11/1980 | Kurtz et al. |
| 4,589,415 A | 5/1986 | Haaga |
| 4,662,378 A | 5/1987 | Thomis |
| 4,838,275 A | 6/1989 | Lee |
| 4,852,570 A | 8/1989 | Levine |
| 4,960,128 A | 10/1990 | Gordon et al. |
| 4,964,408 A | 10/1990 | Hink et al. |
| 4,966,154 A | 10/1990 | Cooper et al. |
| 5,041,187 A | 8/1991 | Hink et al. |
| 5,069,213 A | 12/1991 | Polczynski |
| 5,092,340 A | 3/1992 | Yamaguchi et al. |
| 5,140,519 A | 8/1992 | Friesdorf et al. |
| 5,159,932 A | 11/1992 | Zanetti et al. |
| 5,161,539 A | 11/1992 | Evans et al. |
| 5,163,438 A | 11/1992 | Gordon et al. |
| 5,262,944 A | 11/1993 | Weisner et al. |
| 5,277,189 A | 1/1994 | Jacobs |
| 5,278,627 A | 1/1994 | Aoyagi et al. |
| 5,282,474 A | 2/1994 | Valdes Sosa et al. |
| 5,296,688 A | 3/1994 | Hamilton et al. |
| 5,318,037 A | 6/1994 | Evans et al. |
| 5,319,355 A | 6/1994 | Russek |
| 5,331,549 A | 7/1994 | Crawford, Jr. |
| 5,333,106 A | 7/1994 | Lanpher et al. |
| 5,337,744 A | 8/1994 | Branigan |
| 5,341,805 A | 8/1994 | Stavridi et al. |
| 5,348,008 A | 9/1994 | Bornn et al. |
| 5,358,519 A | 10/1994 | Grandjean |
| D353,195 S | 12/1994 | Savage et al. |
| D353,196 S | 12/1994 | Savage et al. |
| 5,375,599 A | 12/1994 | Schimizu |
| 5,377,676 A | 1/1995 | Vari et al. |
| 5,400,794 A | 3/1995 | Gorman |
| 5,416,695 A | 5/1995 | Stutman et al. |
| D359,546 S | 6/1995 | Savage et al. |
| 5,431,170 A | 7/1995 | Mathews |
| 5,434,611 A | 7/1995 | Tamura |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,483,968 A | 1/1996 | Adam et al. |
| 5,490,505 A | 2/1996 | Diab et al. |
| 5,494,041 A | 2/1996 | Wilk |
| 5,494,043 A | 2/1996 | O'Sullivan et al. |
| 5,503,149 A | 4/1996 | Beavin |
| 5,505,202 A | 4/1996 | Mogi et al. |
| 5,533,511 A | 7/1996 | Kaspari et al. |
| 5,534,851 A | 7/1996 | Russek |
| 5,544,649 A | 8/1996 | David et al. |
| 5,553,609 A | 9/1996 | Chen et al. |
| 5,558,638 A | 9/1996 | Evers et al. |
| 5,561,275 A | 10/1996 | Savage et al. |
| 5,562,002 A | 10/1996 | Lalin |
| 5,566,676 A | 10/1996 | Rosenfeldt et al. |
| 5,566,678 A | 10/1996 | Cadwell |
| 5,576,952 A | 11/1996 | Stutman et al. |
| 5,579,001 A | 11/1996 | Dempsey et al. |
| 5,590,649 A | 1/1997 | Caro et al. |
| 5,602,924 A | 2/1997 | Durand et al. |
| 5,619,991 A | 4/1997 | Sloane |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,640,967 A | 6/1997 | Fine et al. |
| 5,645,440 A | 7/1997 | Tobler et al. |
| 5,685,299 A | 11/1997 | Diab et al. |
| 5,685,314 A | 11/1997 | Geheb et al. |
| 5,687,717 A | 11/1997 | Halpern et al. |
| 5,694,020 A | 12/1997 | Lang et al. |
| 5,724,580 A | 3/1998 | Levin et al. |
| 5,724,983 A | 3/1998 | Selker et al. |
| 5,725,308 A | 3/1998 | Smith et al. |
| 5,734,739 A | 3/1998 | Sheehan et al. |
| D393,830 S | 4/1998 | Tobler et al. |
| 5,743,262 A | 4/1998 | Lepper, Jr. et al. |
| 5,758,079 A | 5/1998 | Ludwig et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,585 A | 6/1998 | Lavin et al. |
| 5,782,757 A | 7/1998 | Diab et al. |
| 5,782,805 A | 7/1998 | Meinzer |
| 5,785,659 A | 7/1998 | Caro et al. |
| 5,791,347 A | 8/1998 | Flaherty et al. |
| 5,801,637 A | 9/1998 | Lomholt |
| 5,810,734 A | 9/1998 | Caro et al. |
| 5,813,403 A | 9/1998 | Soller et al. |
| 5,822,544 A | 10/1998 | Chaco et al. |
| 5,822,546 A | 10/1998 | George |
| 5,823,950 A | 10/1998 | Diab et al. |
| 5,830,131 A | 11/1998 | Caro et al. |
| 5,833,618 A | 11/1998 | Caro et al. |
| 5,855,550 A | 1/1999 | Lai et al. |
| 5,860,919 A | 1/1999 | Kiani-Azarbayjany et al. |

(56) References Cited

U.S. PATENT DOCUMENTS

| | | |
|---|---|---|
| 5,890,929 A | 4/1999 | Mills et al. |
| 5,904,654 A | 5/1999 | Wohltmann et al. |
| 5,910,139 A | 6/1999 | Cochran et al. |
| 5,919,134 A | 7/1999 | Diab |
| 5,921,920 A | 7/1999 | Marshall et al. |
| 5,924,074 A | 7/1999 | Evans |
| 5,931,160 A | 8/1999 | Gilmore et al. |
| 5,934,925 A | 8/1999 | Tobler et al. |
| 5,940,182 A | 8/1999 | Lepper, Jr. et al. |
| 5,941,836 A | 8/1999 | Friedman |
| 5,942,986 A | 8/1999 | Shabot et al. |
| 5,987,343 A | 11/1999 | Kinast |
| 5,987,519 A | 11/1999 | Peifer et al. |
| 5,995,855 A | 11/1999 | Kiani et al. |
| 5,997,343 A | 12/1999 | Mills et al. |
| 6,002,952 A | 12/1999 | Diab et al. |
| 6,006,119 A | 12/1999 | Soller et al. |
| 6,011,986 A | 1/2000 | Diab et al. |
| 6,014,346 A | 1/2000 | Malone |
| 6,018,673 A | 1/2000 | Chin et al. |
| 6,024,699 A | 2/2000 | Surwit et al. |
| 6,027,452 A | 2/2000 | Flaherty et al. |
| 6,032,678 A | 3/2000 | Rottem |
| 6,035,230 A | 3/2000 | Kang |
| 6,036,642 A | 3/2000 | Diab et al. |
| 6,036,718 A | 3/2000 | Ledford et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,093,146 A | 7/2000 | Filangeri |
| 6,101,478 A | 8/2000 | Brown |
| 6,106,463 A | 8/2000 | Wilk |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,129,686 A | 10/2000 | Friedman |
| 6,132,218 A | 10/2000 | Benja-Athon |
| 6,139,494 A | 10/2000 | Cairnes |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,167,258 A | 12/2000 | Schmidt et al. |
| D437,058 S | 1/2001 | Gozani |
| 6,168,563 B1 | 1/2001 | Brown |
| 6,171,237 B1 | 1/2001 | Avitall et al. |
| 6,183,417 B1 | 2/2001 | Gehab et al. |
| 6,184,521 B1 | 2/2001 | Coffin, IV et al. |
| 6,185,448 B1 | 2/2001 | Borovsky |
| 6,195,576 B1 | 2/2001 | John |
| 6,206,830 B1 | 3/2001 | Diab et al. |
| 6,221,012 B1 | 4/2001 | Maschke et al. |
| 6,224,553 B1 | 5/2001 | Nevo |
| 6,229,856 B1 | 5/2001 | Diab et al. |
| 6,230,142 B1 | 5/2001 | Benigno et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,267,723 B1 | 7/2001 | Matsumura et al. |
| 6,269,262 B1 | 7/2001 | Kandori et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,304,767 B1 | 10/2001 | Soller et al. |
| 6,308,089 B1 | 10/2001 | von der Ruhr et al. |
| 6,312,378 B1 | 11/2001 | Bardy |
| 6,317,627 B1 | 11/2001 | Ennen et al. |
| 6,321,100 B1 | 11/2001 | Parker |
| 6,322,502 B1 | 11/2001 | Schoenberg et al. |
| 6,325,761 B1 | 12/2001 | Jay |
| 6,329,139 B1 | 12/2001 | Nova et al. |
| 6,334,065 B1 | 12/2001 | Al-Ali et al. |
| 6,338,039 B1 | 1/2002 | Lonski et al. |
| 6,343,224 B1 | 1/2002 | Parker |
| 6,349,228 B1 | 2/2002 | Kiani et al. |
| 6,354,235 B1 | 3/2002 | Davies |
| 6,360,114 B1 | 3/2002 | Diab et al. |
| 6,364,834 B1 | 4/2002 | Reuss et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,385,476 B1 | 5/2002 | Osadchy et al. |
| 6,385,589 B1 | 5/2002 | Trusheim et al. |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,470,893 B1 | 10/2002 | Boesen |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,524,240 B1 | 2/2003 | Thede |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,544,173 B2 | 4/2003 | West et al. |
| 6,544,174 B2 | 4/2003 | West et al. |
| 6,551,243 B2 | 4/2003 | Bocionek et al. |
| 6,578,428 B1 | 6/2003 | Dromms et al. |
| 6,580,086 B1 | 6/2003 | Schulz et al. |
| 6,582,393 B2 | 6/2003 | Sage, Jr. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,616,606 B1 | 9/2003 | Peterson et al. |
| 6,632,181 B2 | 10/2003 | Flaherty et al. |
| 6,639,668 B1 | 10/2003 | Trepagnier |
| 6,640,116 B2 | 10/2003 | Diab |
| 6,641,533 B2 | 11/2003 | Causey et al. |
| 6,643,530 B2 | 11/2003 | Diab et al. |
| 6,646,556 B1 | 11/2003 | Smith et al. |
| 6,650,917 B2 | 11/2003 | Diab et al. |
| 6,650,939 B2 | 11/2003 | Takpke, II et al. |
| 6,654,624 B2 | 11/2003 | Diab et al. |
| D483,872 S | 12/2003 | Cruz et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,694,180 B1 | 2/2004 | Boesen |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,719,694 B2 | 4/2004 | Weng et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,746,406 B2 | 6/2004 | Lia et al. |
| 6,751,492 B2 | 6/2004 | Ben-haim |
| 6,760,607 B2 | 7/2004 | Al-Ali |
| 6,766,188 B2 | 7/2004 | Soller |
| 6,770,028 B1 | 8/2004 | Ali et al. |

(56) References Cited

U.S. PATENT DOCUMENTS

| | | |
|---|---|---|
| 6,771,994 B2 | 8/2004 | Kiani et al. |
| 6,783,492 B2 | 8/2004 | Dominguez |
| 6,790,178 B1 | 9/2004 | Mault et al. |
| 6,792,300 B1 | 9/2004 | Diab et al. |
| 6,795,724 B2 | 9/2004 | Hogan |
| 6,796,186 B2 | 9/2004 | Lia et al. |
| 6,804,656 B1 | 10/2004 | Rosenfeld |
| 6,807,050 B1 | 10/2004 | Whitehorn et al. |
| 6,813,511 B2 | 11/2004 | Diab et al. |
| 6,816,741 B2 | 11/2004 | Diab |
| 6,817,979 B2 | 11/2004 | Nihtila et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,837,848 B2 | 1/2005 | Bonner et al. |
| 6,841,535 B2 | 1/2005 | Divita et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,855,112 B2 | 2/2005 | Kao et al. |
| 6,860,266 B2 | 3/2005 | Blike |
| 6,861,639 B2 | 3/2005 | Al-Ali |
| 6,897,788 B2 | 5/2005 | Khair et al. |
| 6,898,452 B2 | 5/2005 | Al-Ali et al. |
| 6,907,237 B1 | 6/2005 | Dorenbosch et al. |
| 6,915,149 B2 | 7/2005 | Ben-haim |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,952,340 B2 | 10/2005 | Son |
| 6,961,598 B2 | 11/2005 | Diab |
| 6,970,792 B1 | 11/2005 | Diab |
| 6,979,812 B2 | 12/2005 | Al-Ali |
| 6,980,419 B2 | 12/2005 | Smith et al. |
| 6,983,179 B2 | 1/2006 | Ben-haim |
| 6,985,764 B2 | 1/2006 | Mason et al. |
| 6,988,989 B2 | 1/2006 | Weiner et al. |
| 6,990,087 B2 | 1/2006 | Rao et al. |
| 6,993,371 B2 | 1/2006 | Kiani et al. |
| 6,996,427 B2 | 2/2006 | Ali et al. |
| 6,997,884 B2 | 2/2006 | Ulmsten |
| 6,999,904 B2 | 2/2006 | Weber et al. |
| 7,003,338 B2 | 2/2006 | Weber et al. |
| 7,003,339 B2 | 2/2006 | Diab et al. |
| 7,004,907 B2 | 2/2006 | Banet et al. |
| 7,015,451 B2 | 3/2006 | Dalke et al. |
| 7,024,233 B2 | 4/2006 | Ali et al. |
| 7,025,729 B2 | 4/2006 | De Chazal et al. |
| 7,027,849 B2 | 4/2006 | Al-Ali |
| 7,030,749 B2 | 4/2006 | Al-Ali |
| 7,033,761 B2 | 4/2006 | Shafer |
| 7,035,686 B2 | 4/2006 | Hogan |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,063,666 B2 | 6/2006 | Weng et al. |
| 7,067,893 B2 | 6/2006 | Mills et al. |
| 7,079,035 B2 | 7/2006 | Bock et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,179,228 B2 | 2/2007 | Banet |
| 7,186,966 B2 | 3/2007 | Al-Ali |
| 7,188,621 B2 | 3/2007 | DeVries et al. |
| 7,190,261 B2 | 3/2007 | Al-Ali |
| 7,208,119 B1 | 4/2007 | Kurtock et al. |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,229,415 B2 | 6/2007 | Schwartz |
| 7,238,159 B2 | 7/2007 | Banet et al. |
| 7,239,905 B2 | 7/2007 | Kiani-Azarbayjany et al. |
| 7,241,287 B2 | 7/2007 | Shehada et al. |
| 7,244,251 B2 | 7/2007 | Shehada et al. |
| 7,245,373 B2 | 7/2007 | Soller et al. |
| 7,245,953 B1 | 7/2007 | Parker |
| 7,252,659 B2 | 8/2007 | Shehada et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,256,708 B2 | 8/2007 | Rosenfeld |
| 7,261,697 B2 | 8/2007 | Berstein |
| 7,264,616 B2 | 9/2007 | Shehada et al. |
| 7,267,671 B2 | 9/2007 | Shehada et al. |
| 7,268,859 B2 | 9/2007 | Sage, Jr. et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,285,090 B2 | 10/2007 | Stivoric |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,307,543 B2 | 12/2007 | Rosenfeld |
| 7,313,423 B2 | 12/2007 | Griffin et al. |
| 7,314,446 B2 | 1/2008 | Byrd et al. |
| 7,315,825 B2 | 1/2008 | Rosenfeld |
| 7,321,862 B2 | 1/2008 | Rosenfeld |
| 7,322,971 B2 | 1/2008 | Shehada et al. |
| 7,328,053 B1 | 2/2008 | Diab et al. |
| 7,332,784 B2 | 2/2008 | Mills et al. |
| 7,336,187 B2 | 2/2008 | Hubbard, Jr. et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,178 B2 | 4/2008 | Ziel et al. |
| 7,356,365 B2 | 4/2008 | Schurman |
| 7,361,155 B2 | 4/2008 | Sage, Jr. et al. |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,378,975 B1 | 5/2008 | Smith et al. |
| 7,382,247 B2 | 6/2008 | Welch et al. |
| 7,383,070 B2 | 6/2008 | Diab et al. |
| 7,390,299 B2 | 6/2008 | Weiner et al. |
| 7,395,216 B2 | 7/2008 | Rosenfeld |
| 7,396,330 B2 | 7/2008 | Banet et al. |
| 7,411,509 B2 | 8/2008 | Rosenfeld |
| 7,413,546 B2 | 8/2008 | Agutter et al. |
| 7,415,297 B2 | 8/2008 | Al-Ali et al. |
| 7,419,483 B2 | 9/2008 | Shehada |
| 7,428,432 B2 | 9/2008 | Ali et al. |
| 7,433,827 B2 | 10/2008 | Rosenfeld |
| 7,438,683 B2 | 10/2008 | Al-Ali et al. |
| 7,439,856 B2 | 10/2008 | Weiner et al. |
| 7,440,787 B2 | 10/2008 | Diab |
| 7,454,240 B2 | 11/2008 | Diab et al. |
| 7,454,359 B2 | 11/2008 | Rosenfeld |
| 7,454,360 B2 | 11/2008 | Rosenfeld |
| 7,462,151 B2 | 12/2008 | Childre et al. |
| 7,467,002 B2 | 12/2008 | Weber et al. |
| 7,467,094 B2 | 12/2008 | Rosenfeld |
| 7,469,157 B2 | 12/2008 | Diab et al. |
| 7,471,969 B2 | 12/2008 | Diab et al. |
| 7,471,971 B2 | 12/2008 | Diab et al. |
| 7,475,019 B2 | 1/2009 | Rosenfeld |
| 7,481,772 B2 | 1/2009 | Banet |
| 7,483,729 B2 | 1/2009 | Al-Ali et al. |
| 7,483,730 B2 | 1/2009 | Diab et al. |

(56) References Cited

U.S. PATENT DOCUMENTS

| | | |
|---|---|---|
| 7,489,250 B2 | 2/2009 | Bock et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,497,828 B1 | 3/2009 | Wilk et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,515,043 B2 | 4/2009 | Welch et al. |
| 7,515,044 B2 | 4/2009 | Welch et al. |
| 7,526,328 B2 | 4/2009 | Diab et al. |
| 7,530,942 B1 | 5/2009 | Diab |
| 7,530,949 B2 | 5/2009 | Al-Ali et al. |
| 7,530,955 B2 | 5/2009 | Diab et al. |
| 7,532,919 B2 | 5/2009 | Soyemi et al. |
| 7,549,961 B1 | 6/2009 | Hwang |
| 7,551,717 B2 | 6/2009 | Tome et al. |
| 7,559,520 B2 | 7/2009 | Quijano et al. |
| 7,563,110 B2 | 7/2009 | Al-Ali et al. |
| 7,577,475 B2 | 8/2009 | Consentino et al. |
| 7,588,558 B2 | 9/2009 | Sage, Jr. et al. |
| 7,590,950 B2 | 9/2009 | Collins et al. |
| 7,596,398 B2 | 9/2009 | Al-Ali et al. |
| 7,597,665 B2 | 10/2009 | Wilk et al. |
| 7,612,999 B2 | 11/2009 | Clark et al. |
| 7,616,303 B2 | 11/2009 | Yang et al. |
| 7,618,375 B2 | 11/2009 | Flaherty |
| D606,659 S | 12/2009 | Kiani et al. |
| 7,639,145 B2 | 12/2009 | Lawson et al. |
| 7,647,083 B2 | 1/2010 | Al-Ali et al. |
| 7,650,291 B2 | 1/2010 | Rosenfeld |
| D609,193 S | 2/2010 | Al-Ali et al. |
| 7,654,966 B2 | 2/2010 | Westinskow et al. |
| 7,658,716 B2 | 2/2010 | Banet et al. |
| 7,684,845 B2 | 3/2010 | Juan |
| 7,689,437 B1 | 3/2010 | Teller et al. |
| RE41,236 E | 4/2010 | Seely |
| D614,305 S | 4/2010 | Al-Ali et al. |
| 7,693,697 B2 | 4/2010 | Westinskow et al. |
| RE41,317 E | 5/2010 | Parker |
| 7,722,542 B2 | 5/2010 | Lia et al. |
| 7,729,733 B2 | 6/2010 | Al-Ali et al. |
| 7,734,320 B2 | 6/2010 | Al-Ali |
| 7,736,318 B2 | 6/2010 | Consentino et al. |
| 7,740,590 B2 | 6/2010 | Bernstein |
| 7,761,127 B2 | 7/2010 | Al-Ali et al. |
| 7,761,128 B2 | 7/2010 | Al-Ali et al. |
| 7,763,420 B2 | 7/2010 | Strizker et al. |
| 7,764,982 B2 | 7/2010 | Dalke et al. |
| D621,515 S | 8/2010 | Chua et al. |
| D621,516 S | 8/2010 | Kiani et al. |
| 7,766,818 B2 | 8/2010 | Iketani et al. |
| 7,774,060 B2 | 8/2010 | Westenskow et al. |
| 7,778,851 B2 | 8/2010 | Schoenberg et al. |
| 7,783,879 B2 | 8/2010 | Krummel et al. |
| 7,791,155 B2 | 9/2010 | Diab |
| 7,794,407 B2 | 9/2010 | Rothenberg |
| 7,801,581 B2 | 9/2010 | Diab |
| 7,803,120 B2 | 9/2010 | Banet et al. |
| 7,806,830 B2 | 10/2010 | Bernstein |
| 7,820,184 B2 | 10/2010 | Strizker et al. |
| 7,822,452 B2 | 10/2010 | Schurman et al. |
| RE41,912 E | 11/2010 | Parker |
| 7,831,450 B2 | 11/2010 | Schoenberg |
| 7,841,986 B2 | 11/2010 | He et al. |
| 7,844,313 B2 | 11/2010 | Kiani et al. |
| 7,844,314 B2 | 11/2010 | Al-Ali |
| 7,844,315 B2 | 11/2010 | Al-Ali |
| 7,848,935 B2 | 12/2010 | Gotlib |
| 7,858,322 B2 | 12/2010 | Tymianski et al. |
| 7,865,222 B2 | 1/2011 | Weber et al. |
| 7,865,232 B1 | 1/2011 | Krishnaswamy et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,881,892 B2 | 2/2011 | Soyemi et al. |
| 7,890,156 B2 | 2/2011 | Ooi et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,914,514 B2 | 3/2011 | Calderon |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,963,927 B2 | 6/2011 | Kelleher et al. |
| 7,967,749 B2 | 6/2011 | Hutchinson et al. |
| 7,976,472 B2 | 7/2011 | Kiani |
| 7,988,637 B2 | 8/2011 | Diab |
| 7,988,639 B2 | 8/2011 | Starks |
| 7,990,382 B2 | 8/2011 | Kiani |
| 7,991,446 B2 | 8/2011 | Al-Ali et al. |
| 7,991,463 B2 | 8/2011 | Kelleher et al. |
| 7,991,625 B2 | 8/2011 | Rosenfeld |
| 7,993,275 B2 | 8/2011 | Banet et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,027,846 B2 | 9/2011 | Schoenberg |
| 8,028,701 B2 | 10/2011 | Al-Ali et al. |
| 8,029,765 B2 | 10/2011 | Bellott et al. |
| 8,033,996 B2 | 10/2011 | Behar |
| 8,036,727 B2 | 10/2011 | Schurman et al. |
| 8,036,728 B2 | 10/2011 | Diab et al. |
| 8,036,736 B2 | 10/2011 | Snyder et al. |
| 8,038,625 B2 | 10/2011 | Afonso et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,068,104 B2 | 11/2011 | Rampersad |
| 8,073,707 B2 | 12/2011 | Teller et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| D659,836 S | 5/2012 | Bensch et al. |
| 8,170,887 B2 | 5/2012 | Rosenfeld |
| 8,175,672 B2 | 5/2012 | Parker |
| 8,175,895 B2 | 5/2012 | Rosenfeld |
| 8,180,420 B2 | 5/2012 | Diab et al. |
| 8,180,440 B2 | 5/2012 | McCombie et al. |
| 8,182,443 B1 | 5/2012 | Kiani |
| 8,185,180 B2 | 5/2012 | Diab et al. |
| 8,190,223 B2 | 5/2012 | Al-ali et al. |
| 8,190,227 B2 | 5/2012 | Diab et al. |
| 8,200,321 B2 | 6/2012 | McCombie et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,206,312 B2 | 6/2012 | Farquhar |
| 8,214,007 B2 | 7/2012 | Baker et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |

(56) References Cited

U.S. PATENT DOCUMENTS

| | | |
|---|---|---|
| 8,233,955 B2 | 7/2012 | Al-Ali et al. |
| 8,235,907 B2 | 8/2012 | Wilk et al. |
| 8,239,010 B2 | 8/2012 | Banet et al. |
| 8,239,780 B2 | 8/2012 | Manetta et al. |
| 8,241,213 B2 | 8/2012 | Lynn et al. |
| 8,244,325 B2 | 8/2012 | Al-Ali et al. |
| 8,249,815 B2 | 8/2012 | Taylor |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,294,588 B2 | 10/2012 | Fisher et al. |
| 8,294,716 B2 | 10/2012 | Lord et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,311,747 B2 | 11/2012 | Taylor |
| 8,311,748 B2 | 11/2012 | Taylor et al. |
| 8,315,683 B2 | 11/2012 | Al-Ali et al. |
| 8,315,812 B2 | 11/2012 | Taylor |
| 8,315,813 B2 | 11/2012 | Taylor et al. |
| 8,315,814 B2 | 11/2012 | Taylor et al. |
| 8,321,004 B2 | 11/2012 | Moon et al. |
| 8,321,150 B2 | 11/2012 | Taylor |
| RE43,860 E | 12/2012 | Parker |
| 8,326,649 B2 | 12/2012 | Rosenfeld |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,360,936 B2 | 1/2013 | Dibenedetto et al. |
| 8,364,223 B2 | 1/2013 | Al-Ali et al. |
| 8,364,226 B2 | 1/2013 | Diab et al. |
| 8,364,250 B2 | 1/2013 | Moon et al. |
| 8,374,665 B2 | 2/2013 | Lamego |
| 8,385,995 B2 | 2/2013 | Al-ali et al. |
| 8,385,996 B2 | 2/2013 | Smith et al. |
| D679,018 S | 3/2013 | Fullerton et al. |
| 8,388,353 B2 | 3/2013 | Kiani et al. |
| 8,399,822 B2 | 3/2013 | Al-Ali |
| 8,401,602 B2 | 3/2013 | Kiani |
| 8,401,874 B2 | 3/2013 | Rosenfeld |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,419,649 B2 | 4/2013 | Banet et al. |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,824 B2 | 5/2013 | Moon et al. |
| 8,437,825 B2 | 5/2013 | Dalvi et al. |
| 8,442,607 B2 | 5/2013 | Banet et al. |
| 8,449,469 B2 | 5/2013 | Banet et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,475,370 B2 | 7/2013 | McCombie et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,506,480 B2 | 8/2013 | Banet et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,527,038 B2 | 9/2013 | Moon et al. |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,545,417 B2 | 10/2013 | Banet et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,554,297 B2 | 10/2013 | Moon et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,574,161 B2 | 11/2013 | Banet et al. |
| 8,577,431 B2 | 11/2013 | Lamego et al. |
| 8,579,813 B2 | 11/2013 | Causey, III et al. |
| 8,581,732 B2 | 11/2013 | Al-Ali et al. |
| 8,588,880 B2 | 11/2013 | Abdul-Hafiz et al. |
| 8,588,924 B2 | 11/2013 | Dion |
| 8,591,411 B2 | 11/2013 | Banet et al. |
| 8,594,776 B2 | 11/2013 | McCombie et al. |
| 8,584,345 B2 | 12/2013 | Al-Ali et al. |
| 8,600,467 B2 | 12/2013 | Al-Ali et al. |
| 8,600,777 B2 | 12/2013 | Schoenberg |
| 8,602,997 B2 | 12/2013 | Banet et al. |
| 8,606,342 B2 | 12/2013 | Diab |
| 8,620,678 B2 | 12/2013 | Gotlib |
| 8,622,922 B2 | 1/2014 | Banet et al. |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,672,854 B2 | 3/2014 | McCombie et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,727,977 B2 | 5/2014 | Banet et al. |
| 8,738,118 B2 | 5/2014 | Moon et al. |
| 8,740,792 B1 | 6/2014 | Kiani et al. |
| 8,740,802 B2 | 6/2014 | Banet et al. |
| 8,740,807 B2 | 6/2014 | Banet et al. |
| 8,747,330 B2 | 6/2014 | Banet et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| D709,846 S | 7/2014 | Oswaks |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |

(56) References Cited

U.S. PATENT DOCUMENTS

| | | |
|---|---|---|
| 8,790,268 B2 | 7/2014 | Al-Ali |
| 8,801,613 B2 | 8/2014 | Al-Ali et al. |
| 8,808,188 B2 | 8/2014 | Banet et al. |
| 8,818,477 B2 | 8/2014 | Soller |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,866,620 B2 | 10/2014 | Amir |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,873,035 B2 | 10/2014 | Yang et al. |
| 8,878,888 B2 | 11/2014 | Rosenfeld |
| 8,886,271 B2 | 11/2014 | Kiani et al. |
| 8,888,539 B2 | 11/2014 | Al-Ali et al. |
| 8,888,700 B2 | 11/2014 | Banet et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,907,287 B2 | 12/2014 | Vanderpohl |
| 8,909,310 B2 | 12/2014 | Lamego et al. |
| 8,909,330 B2 | 12/2014 | McCombie et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,956,293 B2 | 2/2015 | McCombie et al. |
| 8,956,294 B2 | 2/2015 | McCombie et al. |
| 8,965,471 B2 | 2/2015 | Lamego |
| 8,979,765 B2 | 3/2015 | Banet et al. |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,055,928 B2 | 6/2015 | McCombie et al. |
| 9,057,689 B2 | 6/2015 | Soller et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,291 B2 | 8/2015 | Soller et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,149,192 B2 | 10/2015 | Banet et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,700 B2 | 10/2015 | Banet et al. |
| 9,161,713 B2 | 10/2015 | Al-Ali et al. |
| 9,167,995 B2 | 10/2015 | Lamego et al. |
| 9,173,593 B2 | 11/2015 | Banet et al. |
| 9,173,594 B2 | 11/2015 | Banet et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| D745,167 S | 12/2015 | Canas et al. |
| 9,211,072 B2 | 12/2015 | Kiani |
| 9,211,095 B1 | 12/2015 | Al-Ali |
| 9,215,986 B2 | 12/2015 | Banet et al. |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,915 B2 | 4/2016 | McCombie et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,209 B2 | 5/2016 | Banet et al. |
| 9,339,211 B2 | 5/2016 | Banet et al. |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,158 B2 | 6/2016 | Banet et al. |
| 9,364,181 B2 | 6/2016 | Kiani |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Al-Ali et al. |
| 9,380,952 B2 | 7/2016 | Banet et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,408,573 B2 | 8/2016 | Welch et al. |
| 9,436,645 B2 | 9/2016 | Al-Ali et al. |
| 9,439,574 B2 | 9/2016 | McCombie et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,007 B2 | 2/2017 | McCombie et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,655,546 B2 | 5/2017 | Shen et al. |
| 9,662,052 B2 | 5/2017 | Al-Ali et al. |

(56) References Cited

U.S. PATENT DOCUMENTS

| | | |
|---|---|---|
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,728,061 B2 | 8/2017 | Shen et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Al-Ali et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 2001/0011355 A1 | 8/2001 | Kawai |
| 2001/0046366 A1 | 11/2001 | Susskind |
| 2002/0045836 A1 | 4/2002 | Alkawwas |
| 2002/0052311 A1 | 5/2002 | Solomon et al. |
| 2002/0063690 A1 | 5/2002 | Chung et al. |
| 2002/0140675 A1 | 10/2002 | Ali et al. |
| 2002/0177758 A1 | 11/2002 | Schoenberg |
| 2003/0027326 A1 | 2/2003 | Ulmsten et al. |
| 2003/0052787 A1 | 3/2003 | Zerhusen et al. |
| 2003/0058838 A1 | 3/2003 | Wengrovitz |
| 2003/0158466 A1 | 8/2003 | Lynn et al. |
| 2003/0216670 A1 | 11/2003 | Beggs |
| 2004/0013647 A1 | 1/2004 | Solomon et al. |
| 2004/0090742 A1 | 5/2004 | Son et al. |
| 2004/0122787 A1 | 6/2004 | Avinash et al. |
| 2004/0126007 A1 | 7/2004 | Ziel et al. |
| 2004/0147818 A1 | 7/2004 | Levy et al. |
| 2004/0179332 A1 | 9/2004 | Smith et al. |
| 2004/0186357 A1 | 9/2004 | Soderberg et al. |
| 2004/0230179 A1 | 11/2004 | Shehada et al. |
| 2004/0243017 A1 | 12/2004 | Causevic |
| 2004/0254431 A1 | 12/2004 | Shehada et al. |
| 2004/0254432 A1 | 12/2004 | Shehada et al. |
| 2005/0005710 A1 | 1/2005 | Sage, Jr. |
| 2005/0009926 A1 | 1/2005 | Kreye et al. |
| 2005/0020918 A1 | 1/2005 | Wilk et al. |
| 2005/0038332 A1 | 2/2005 | Saidara et al. |
| 2005/0038680 A1 | 2/2005 | McMahon |
| 2005/0065417 A1 | 3/2005 | Ali et al. |
| 2005/0080336 A1 | 4/2005 | Byrd et al. |
| 2005/0096542 A1 | 5/2005 | Weng et al. |
| 2005/0113653 A1 | 5/2005 | Fox et al. |
| 2005/0124864 A1 | 6/2005 | Mack et al. |
| 2005/0125256 A1 | 6/2005 | Schoenberg |
| 2005/0148882 A1 | 7/2005 | Banet et al. |
| 2005/0164933 A1 | 7/2005 | Tymianski et al. |
| 2005/0191294 A1 | 9/2005 | Arap et al. |
| 2005/0208648 A1 | 9/2005 | Sage, Jr. et al. |
| 2005/0209518 A1 | 9/2005 | Sage, Jr. et al. |
| 2005/0228244 A1 | 10/2005 | Banet |
| 2005/0228299 A1 | 10/2005 | Banet |
| 2005/0242946 A1 | 11/2005 | Hubbard, Jr. et al. |
| 2005/0245831 A1 | 11/2005 | Banet |
| 2005/0245839 A1* | 11/2005 | Stivoric ............. G06F 19/3418 600/549 |
| 2005/0261594 A1 | 11/2005 | Banet |
| 2005/0261598 A1 | 11/2005 | Banet et al. |
| 2005/0268401 A1 | 12/2005 | Dixon et al. |
| 2005/0277872 A1 | 12/2005 | Colby, Jr. et al. |
| 2006/0009697 A1 | 1/2006 | Banet et al. |
| 2006/0009698 A1 | 1/2006 | Banet et al. |
| 2006/0049936 A1 | 3/2006 | Collins, Jr. et al. |
| 2006/0058647 A1 | 3/2006 | Strommer et al. |
| 2006/0084878 A1 | 4/2006 | Banet et al. |
| 2006/0089543 A1 | 4/2006 | Kim et al. |
| 2006/0094936 A1 | 5/2006 | Russ |
| 2006/0149393 A1 | 7/2006 | Calderon |
| 2006/0155175 A1 | 7/2006 | Ogino et al. |
| 2006/0161054 A1 | 7/2006 | Reuss et al. |
| 2006/0200009 A1 | 9/2006 | Wekell et al. |
| 2006/0217684 A1 | 9/2006 | Shehada et al. |
| 2006/0217685 A1 | 9/2006 | Shehada et al. |
| 2006/0224413 A1 | 10/2006 | Kim et al. |
| 2006/0235300 A1 | 10/2006 | Weng et al. |
| 2006/0253042 A1 | 11/2006 | Stahmann et al. |
| 2007/0000490 A1 | 1/2007 | DeVries et al. |
| 2007/0021675 A1 | 1/2007 | Childre et al. |
| 2007/0027368 A1 | 2/2007 | Collins et al. |
| 2007/0032733 A1 | 2/2007 | Burton et al. |
| 2007/0055116 A1 | 3/2007 | Clark et al. |
| 2007/0055544 A1 | 3/2007 | Jung et al. |
| 2007/0060798 A1 | 3/2007 | Krupnik et al. |
| 2007/0088406 A1 | 4/2007 | Bennett et al. |
| 2007/0096897 A1 | 5/2007 | Weiner |
| 2007/0100222 A1 | 5/2007 | Mastrototaro et al. |
| 2007/0118399 A1 | 5/2007 | Avinash et al. |
| 2007/0140475 A1 | 6/2007 | Kurtock et al. |
| 2007/0142715 A1 | 6/2007 | Banet et al. |
| 2007/0156033 A1 | 7/2007 | Causey et al. |

(56) References Cited

U.S. PATENT DOCUMENTS

| | | |
|---|---|---|
| 2007/0157285 A1 | 7/2007 | Frank et al. |
| 2007/0159332 A1 | 7/2007 | Koblasz |
| 2007/0163589 A1 | 7/2007 | DeVries et al. |
| 2007/0180140 A1 | 8/2007 | Welch et al. |
| 2007/0185390 A1 | 8/2007 | Perkins et al. |
| 2007/0185393 A1 | 8/2007 | Zhou et al. |
| 2007/0232941 A1 | 10/2007 | Rabinovich |
| 2007/0244724 A1 | 10/2007 | Pendergast et al. |
| 2007/0250286 A1* | 10/2007 | Duncan ............ A61B 5/1121 702/139 |
| 2007/0254593 A1 | 11/2007 | Jollota et al. |
| 2007/0255114 A1 | 11/2007 | Ackermann et al. |
| 2007/0255116 A1 | 11/2007 | Mehta et al. |
| 2007/0255250 A1 | 11/2007 | Moberg |
| 2007/0276261 A1 | 11/2007 | Banet et al. |
| 2007/0276262 A1 | 11/2007 | Banet et al. |
| 2007/0276632 A1 | 11/2007 | Banet et al. |
| 2007/0282478 A1 | 12/2007 | Al-Ali et al. |
| 2008/0000479 A1 | 1/2008 | Elaz et al. |
| 2008/0003200 A1 | 1/2008 | Arap et al. |
| 2008/0021854 A1 | 1/2008 | Jung et al. |
| 2008/0033661 A1 | 2/2008 | Syroid et al. |
| 2008/0051670 A1 | 2/2008 | Banet et al. |
| 2008/0053438 A1 | 3/2008 | DeVries et al. |
| 2008/0058614 A1 | 3/2008 | Banet et al. |
| 2008/0058657 A1 | 3/2008 | Schwartz et al. |
| 2008/0077026 A1 | 3/2008 | Banet et al. |
| 2008/0082004 A1 | 4/2008 | Banet et al. |
| 2008/0090626 A1 | 4/2008 | Griffin et al. |
| 2008/0091089 A1 | 4/2008 | Guillory et al. |
| 2008/0091090 A1 | 4/2008 | Guillory et al. |
| 2008/0091471 A1 | 4/2008 | Michon et al. |
| 2008/0097167 A1 | 4/2008 | Yudkovitch et al. |
| 2008/0099366 A1 | 5/2008 | Niemiec et al. |
| 2008/0108884 A1 | 5/2008 | Kiani |
| 2008/0114220 A1 | 5/2008 | Banet et al. |
| 2008/0119412 A1 | 5/2008 | Tymianski et al. |
| 2008/0138278 A1 | 6/2008 | Scherz et al. |
| 2008/0169922 A1 | 7/2008 | Issokson |
| 2008/0171919 A1 | 7/2008 | Stivoric et al. |
| 2008/0188795 A1 | 8/2008 | Katz et al. |
| 2008/0194918 A1 | 8/2008 | Kulik et al. |
| 2008/0208912 A1 | 8/2008 | Garibaldi |
| 2008/0221396 A1 | 9/2008 | Garces et al. |
| 2008/0221399 A1 | 9/2008 | Zhou et al. |
| 2008/0221461 A1 | 9/2008 | Zhou et al. |
| 2008/0228077 A1 | 9/2008 | Wilk et al. |
| 2008/0275309 A1 | 11/2008 | Stivoric et al. |
| 2008/0281167 A1 | 11/2008 | Soderberg et al. |
| 2008/0281168 A1 | 11/2008 | Gibson et al. |
| 2008/0281181 A1 | 11/2008 | Manzione et al. |
| 2008/0287751 A1 | 11/2008 | Stivoric et al. |
| 2008/0292172 A1 | 11/2008 | Assmann et al. |
| 2008/0300020 A1 | 12/2008 | Nishizawa et al. |
| 2008/0312542 A1 | 12/2008 | Banet et al. |
| 2008/0319275 A1 | 12/2008 | Chiu et al. |
| 2008/0319327 A1 | 12/2008 | Banet et al. |
| 2008/0319354 A1 | 12/2008 | Bell et al. |
| 2009/0005651 A1 | 1/2009 | Ward et al. |
| 2009/0018409 A1 | 1/2009 | Banet et al. |
| 2009/0018422 A1 | 1/2009 | Banet et al. |
| 2009/0018453 A1 | 1/2009 | Banet et al. |
| 2009/0018808 A1 | 1/2009 | Bronstein et al. |
| 2009/0024008 A1 | 1/2009 | Brunner et al. |
| 2009/0052623 A1 | 2/2009 | Tome et al. |
| 2009/0054735 A1 | 2/2009 | Higgins et al. |
| 2009/0054743 A1 | 2/2009 | Stewart |
| 2009/0062682 A1 | 3/2009 | Bland et al. |
| 2009/0069642 A1 | 3/2009 | Gao et al. |
| 2009/0069868 A1 | 3/2009 | Bengtsson et al. |
| 2009/0099480 A1 | 4/2009 | Salgo et al. |
| 2009/0112072 A1 | 4/2009 | Banet et al. |
| 2009/0118628 A1 | 5/2009 | Zhou et al. |
| 2009/0119330 A1 | 5/2009 | Sampath et al. |
| 2009/0119843 A1 | 5/2009 | Rodgers et al. |
| 2009/0124867 A1 | 5/2009 | Hirsch et al. |
| 2009/0131759 A1 | 5/2009 | Sims et al. |
| 2009/0143832 A1 | 6/2009 | Saba |
| 2009/0157058 A1 | 6/2009 | Ferren et al. |
| 2009/0171170 A1 | 7/2009 | Li et al. |
| 2009/0171225 A1 | 7/2009 | Gadodia et al. |
| 2009/0177090 A1 | 7/2009 | Grunwald et al. |
| 2009/0182287 A1 | 7/2009 | Kassab |
| 2009/0226372 A1 | 9/2009 | Ruoslahti et al. |
| 2009/0247984 A1 | 10/2009 | Lamego et al. |
| 2009/0264778 A1 | 10/2009 | Markowitz et al. |
| 2009/0275813 A1 | 11/2009 | Davis |
| 2009/0275844 A1 | 11/2009 | Al-Ali |
| 2009/0281462 A1 | 11/2009 | Heliot et al. |
| 2009/0299157 A1 | 12/2009 | Telfort et al. |
| 2009/0309755 A1 | 12/2009 | Williamson et al. |
| 2010/0004518 A1 | 1/2010 | Vo et al. |
| 2010/0030040 A1 | 2/2010 | Poeze et al. |
| 2010/0030094 A1 | 2/2010 | Lundback |
| 2010/0036209 A1 | 2/2010 | Ferren et al. |
| 2010/0069725 A1 | 3/2010 | Al-Ali |
| 2010/0125217 A1 | 5/2010 | Kuo et al. |
| 2010/0130875 A1 | 5/2010 | Banet et al. |
| 2010/0144627 A1 | 6/2010 | Vitek et al. |
| 2010/0160794 A1 | 6/2010 | Banet et al. |
| 2010/0160795 A1 | 6/2010 | Banet et al. |
| 2010/0160796 A1 | 6/2010 | Banet et al. |
| 2010/0160797 A1 | 6/2010 | Banet et al. |
| 2010/0160798 A1 | 6/2010 | Banet et al. |
| 2010/0168536 A1 | 7/2010 | Banet et al. |
| 2010/0168589 A1 | 7/2010 | Banet et al. |
| 2010/0185101 A1 | 7/2010 | Sakai et al. |
| 2010/0198622 A1 | 8/2010 | Gajic et al. |
| 2010/0210958 A1 | 8/2010 | Manwaring et al. |
| 2010/0261979 A1 | 10/2010 | Kiani |
| 2010/0261982 A1 | 10/2010 | Noury et al. |
| 2010/0298650 A1 | 11/2010 | Moon et al. |
| 2010/0298651 A1 | 11/2010 | Moon et al. |
| 2010/0298652 A1 | 11/2010 | McCombie et al. |
| 2010/0298653 A1 | 11/2010 | McCombie et al. |
| 2010/0298654 A1 | 11/2010 | McCombie et al. |
| 2010/0298655 A1 | 11/2010 | McCombie et al. |
| 2010/0298656 A1 | 11/2010 | McCombie et al. |
| 2010/0298657 A1 | 11/2010 | McCombie et al. |
| 2010/0298658 A1 | 11/2010 | McCombie et al. |
| 2010/0298659 A1 | 11/2010 | McCombie et al. |
| 2010/0298660 A1 | 11/2010 | McCombie et al. |
| 2010/0298661 A1 | 11/2010 | McCombie et al. |
| 2010/0298742 A1 | 11/2010 | Perlman et al. |
| 2010/0305412 A1 | 12/2010 | Darrah et al. |
| 2010/0312103 A1 | 12/2010 | Gorek et al. |
| 2010/0317936 A1 | 12/2010 | Al-Ali et al. |
| 2010/0317951 A1 | 12/2010 | Rutkowski et al. |
| 2010/0324384 A1 | 12/2010 | Moon et al. |
| 2010/0324385 A1 | 12/2010 | Moon et al. |
| 2010/0324386 A1 | 12/2010 | Moon et al. |
| 2010/0324387 A1 | 12/2010 | Moon et al. |
| 2010/0324388 A1 | 12/2010 | Moon et al. |
| 2010/0324389 A1 | 12/2010 | Moon et al. |
| 2011/0001605 A1 | 1/2011 | Kiani et al. |
| 2011/0021930 A1 | 1/2011 | Mazzeo et al. |
| 2011/0023130 A1 | 1/2011 | Gudgel et al. |
| 2011/0028809 A1 | 2/2011 | Goodman |
| 2011/0046495 A1 | 2/2011 | Osypka |
| 2011/0066051 A1 | 3/2011 | Moon et al. |
| 2011/0077473 A1 | 3/2011 | Lisogurski |
| 2011/0077488 A1 | 3/2011 | Buxton et al. |
| 2011/0078596 A1 | 3/2011 | Rawlins et al. |
| 2011/0080294 A1 | 4/2011 | Tanishima et al. |
| 2011/0082711 A1 | 4/2011 | Poeze et al. |
| 2011/0087084 A1 | 4/2011 | Jeong et al. |
| 2011/0087117 A1 | 4/2011 | Tremper et al. |
| 2011/0087756 A1 | 4/2011 | Biondi et al. |
| 2011/0098583 A1 | 4/2011 | Pandia et al. |
| 2011/0105854 A1 | 5/2011 | Kiani et al. |
| 2011/0118573 A1 | 5/2011 | Mckenna |
| 2011/0125060 A1 | 5/2011 | Telfort et al. |
| 2011/0152629 A1 | 6/2011 | Eaton et al. |
| 2011/0172967 A1 | 7/2011 | Al-Ali et al. |

(56) References Cited

U.S. PATENT DOCUMENTS

| | | |
|---|---|---|
| 2011/0184252 A1 | 7/2011 | Archer et al. |
| 2011/0184253 A1 | 7/2011 | Archer et al. |
| 2011/0208015 A1 | 8/2011 | Welch et al. |
| 2011/0208018 A1 | 8/2011 | Kiani |
| 2011/0208073 A1 | 8/2011 | Matsukawa et al. |
| 2011/0209915 A1 | 9/2011 | Telfort et al. |
| 2011/0212090 A1 | 9/2011 | Pedersen et al. |
| 2011/0213212 A1 | 9/2011 | Al-Ali |
| 2011/0224498 A1 | 9/2011 | Banet et al. |
| 2011/0224499 A1 | 9/2011 | Banet et al. |
| 2011/0224500 A1 | 9/2011 | Banet et al. |
| 2011/0224506 A1 | 9/2011 | Moon et al. |
| 2011/0224507 A1 | 9/2011 | Banet et al. |
| 2011/0224508 A1 | 9/2011 | Moon et al. |
| 2011/0224556 A1 | 9/2011 | Moon et al. |
| 2011/0224557 A1 | 9/2011 | Banet et al. |
| 2011/0224564 A1 | 9/2011 | Moon et al. |
| 2011/0227739 A1 | 9/2011 | Gilham et al. |
| 2011/0230733 A1 | 9/2011 | Al-Ali |
| 2011/0237911 A1 | 9/2011 | Lamego et al. |
| 2011/0257489 A1 | 10/2011 | Banet et al. |
| 2011/0257544 A1 | 10/2011 | Kaasinen et al. |
| 2011/0257551 A1 | 10/2011 | Banet et al. |
| 2011/0257552 A1 | 10/2011 | Banet et al. |
| 2011/0257553 A1 | 10/2011 | Banet et al. |
| 2011/0257554 A1 | 10/2011 | Banet et al. |
| 2011/0257555 A1 | 10/2011 | Banet et al. |
| 2011/0263950 A1 | 10/2011 | Larson et al. |
| 2011/0288421 A1 | 11/2011 | Banet et al. |
| 2011/0295094 A1 | 12/2011 | Doyle et al. |
| 2012/0001751 A1 | 1/2012 | Baker et al. |
| 2012/0004579 A1 | 1/2012 | Luo et al. |
| 2012/0029300 A1 | 2/2012 | Paquet |
| 2012/0029304 A1 | 2/2012 | Medina et al. |
| 2012/0029879 A1 | 2/2012 | Sing et al. |
| 2012/0059230 A1 | 3/2012 | Teller et al. |
| 2012/0059267 A1 | 3/2012 | Lamego et al. |
| 2012/0071771 A1 | 3/2012 | Behar |
| 2012/0075464 A1 | 3/2012 | Derenne et al. |
| 2012/0095778 A1 | 4/2012 | Gross et al. |
| 2012/0101353 A1 | 4/2012 | Reggiardo et al. |
| 2012/0108983 A1 | 5/2012 | Banet et al. |
| 2012/0116175 A1 | 5/2012 | Al-Ali et al. |
| 2012/0117209 A1 | 5/2012 | Sinha |
| 2012/0123799 A1 | 5/2012 | Nolen et al. |
| 2012/0136221 A1 | 5/2012 | Killen et al. |
| 2012/0165629 A1 | 6/2012 | Merritt et al. |
| 2012/0179006 A1 | 7/2012 | Jansen et al. |
| 2012/0179011 A1 | 7/2012 | Moon et al. |
| 2012/0184120 A1 | 7/2012 | Basta et al. |
| 2012/0190949 A1 | 7/2012 | McCombie et al. |
| 2012/0197619 A1 | 8/2012 | Namer Yelin et al. |
| 2012/0203078 A1 | 8/2012 | Sze et al. |
| 2012/0209082 A1 | 8/2012 | Al-Ali |
| 2012/0209084 A1 | 8/2012 | Olsen et al. |
| 2012/0226160 A1 | 9/2012 | Kudoh |
| 2012/0227739 A1 | 9/2012 | Kiani |
| 2012/0239434 A1 | 9/2012 | Breslow et al. |
| 2012/0242501 A1 | 9/2012 | Tran et al. |
| 2012/0265039 A1 | 10/2012 | Kiani |
| 2012/0282583 A1 | 11/2012 | Thaler et al. |
| 2012/0283524 A1 | 11/2012 | Kiani et al. |
| 2012/0284053 A1 | 11/2012 | Rosenfeld |
| 2012/0286955 A1 | 11/2012 | Welch et al. |
| 2012/0294801 A1 | 11/2012 | Scherz et al. |
| 2012/0296178 A1 | 11/2012 | Lamego et al. |
| 2012/0302894 A1 | 11/2012 | Diab et al. |
| 2012/0319816 A1 | 12/2012 | Al-Ali |
| 2012/0330112 A1 | 12/2012 | Lamego et al. |
| 2013/0006131 A1 | 1/2013 | Narayan et al. |
| 2013/0006151 A1 | 1/2013 | Main et al. |
| 2013/0023775 A1 | 1/2013 | Lamego et al. |
| 2013/0035603 A1 | 2/2013 | Jarausch et al. |
| 2013/0041591 A1 | 2/2013 | Lamego |
| 2013/0045685 A1 | 2/2013 | Kiani |
| 2013/0046197 A1 | 2/2013 | Dlugos, Jr. et al. |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0096405 A1 | 4/2013 | Garfio |
| 2013/0096936 A1 | 4/2013 | Sampath et al. |
| 2013/0109929 A1 | 5/2013 | Menzel |
| 2013/0109935 A1 | 5/2013 | Al-Ali et al. |
| 2013/0109937 A1 | 5/2013 | Banet et al. |
| 2013/0116515 A1 | 5/2013 | Banet et al. |
| 2013/0155889 A1 | 6/2013 | Brownworth et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0261494 A1 | 10/2013 | Bloom et al. |
| 2013/0262730 A1 | 10/2013 | Al-Ali et al. |
| 2013/0274571 A1 | 10/2013 | Diab et al. |
| 2013/0296672 A1 | 11/2013 | O'Neil et al. |
| 2013/0296713 A1 | 11/2013 | Al-Ali et al. |
| 2013/0317327 A1 | 11/2013 | Al-Ali et al. |
| 2013/0317370 A1 | 11/2013 | Dalvi et al. |
| 2013/0317393 A1 | 11/2013 | Weiss et al. |
| 2013/0324808 A1 | 12/2013 | Al-Ali et al. |
| 2013/0324817 A1 | 12/2013 | Diab |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2013/0340176 A1 | 12/2013 | Stevens et al. |
| 2014/0005502 A1 | 1/2014 | Klap et al. |
| 2014/0012100 A1 | 1/2014 | Al-Ali et al. |
| 2014/0022081 A1 | 1/2014 | Ribble et al. |
| 2014/0025010 A1 | 1/2014 | Stroup et al. |
| 2014/0025306 A1 | 1/2014 | Weber et al. |
| 2014/0031650 A1 | 1/2014 | Weber et al. |
| 2014/0034353 A1 | 2/2014 | Al-Ali et al. |
| 2014/0046674 A1 | 2/2014 | Rosenfeld |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0073167 A1 | 3/2014 | Al-Ali et al. |
| 2014/0077956 A1 | 3/2014 | Sampath et al. |
| 2014/0081097 A1 | 3/2014 | Al-Ali et al. |
| 2014/0081099 A1 | 3/2014 | Banet et al. |
| 2014/0081100 A1 | 3/2014 | Muhsin et al. |
| 2014/0081175 A1 | 3/2014 | Telfort |
| 2014/0088385 A1 | 3/2014 | Moon et al. |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0142445 A1 | 5/2014 | Banet et al. |
| 2014/0152673 A1 | 6/2014 | Lynn et al. |
| 2014/0155712 A1 | 6/2014 | Lamego et al. |
| 2014/0163344 A1 | 6/2014 | Al-Ali |
| 2014/0163393 A1 | 6/2014 | McCombie et al. |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |

(56) References Cited

U.S. PATENT DOCUMENTS

| | | |
|---|---|---|
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200415 A1 | 7/2014 | McCombie et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0235964 A1 | 8/2014 | Banet et al. |
| 2014/0243627 A1 | 8/2014 | Diab et al. |
| 2014/0249431 A1 | 9/2014 | Banet et al. |
| 2014/0249432 A1 | 9/2014 | Banet et al. |
| 2014/0249433 A1 | 9/2014 | Banet et al. |
| 2014/0249434 A1 | 9/2014 | Banet et al. |
| 2014/0249435 A1 | 9/2014 | Banet et al. |
| 2014/0249440 A1 | 9/2014 | Banet et al. |
| 2014/0249441 A1 | 9/2014 | Banet et al. |
| 2014/0249442 A1 | 9/2014 | Banet et al. |
| 2014/0257056 A1 | 9/2014 | Moon et al. |
| 2014/0257057 A1 | 9/2014 | Reis Cunha et al. |
| 2014/0266787 A1 | 9/2014 | Tran |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0276145 A1 | 9/2014 | Banet et al. |
| 2014/0276175 A1 | 9/2014 | Banet et al. |
| 2014/0288400 A1 | 9/2014 | Diab et al. |
| 2014/0296664 A1 | 10/2014 | Bruinsma et al. |
| 2014/0301893 A1 | 10/2014 | Stroup et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0343889 A1 | 11/2014 | Ben Shalom et al. |
| 2014/0357966 A1 | 12/2014 | Al-Ali et al. |
| 2014/0375428 A1 | 12/2014 | Park |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0094618 A1 | 4/2015 | Russell et al. |
| 2015/0097701 A1 | 4/2015 | Al-Ali et al. |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0164437 A1 | 6/2015 | McCombie et al. |
| 2015/0165312 A1 | 6/2015 | Kiani |
| 2015/0196249 A1 | 7/2015 | Brown et al. |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0254956 A1 | 9/2015 | Shen et al. |
| 2015/0257689 A1 | 9/2015 | Al-Ali et al. |
| 2015/0272481 A1 | 10/2015 | Glaser et al. |
| 2015/0272514 A1 | 10/2015 | Kiani et al. |
| 2015/0282717 A1 | 10/2015 | McCombie et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank et al. |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0022224 A1 | 1/2016 | Banet et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0045163 A1 | 2/2016 | Weisner et al. |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali |
| 2016/0143546 A1 | 5/2016 | McCombie et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0183794 A1* | 6/2016 | Gannon ............... A61B 5/0008 600/549 |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom |
| 2016/0228043 A1 | 8/2016 | O'Neil et al. |
| 2016/0228050 A1 | 8/2016 | Sugla et al. |
| 2016/0233632 A1 | 8/2016 | Scruggs et al. |
| 2016/0234944 A1 | 8/2016 | Schmidt et al. |
| 2016/0242681 A1 | 8/2016 | Shen et al. |
| 2016/0256080 A1 | 9/2016 | Shen et al. |
| 2016/0270735 A1 | 9/2016 | Diab et al. |
| 2016/0275776 A1 | 9/2016 | Shen et al. |
| 2016/0278691 A1 | 9/2016 | Larson et al. |
| 2016/0278692 A1 | 9/2016 | Larson et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296159 A1 | 10/2016 | Larson et al. |
| 2016/0296160 A1 | 10/2016 | Larson et al. |
| 2016/0296169 A1 | 10/2016 | McHale et al. |
| 2016/0302698 A1 | 10/2016 | Perlman |
| 2016/0302715 A1 | 10/2016 | Larson et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367170 A1 | 12/2016 | Larson et al. |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |

(56) References Cited

U.S. PATENT DOCUMENTS

| | | |
|---|---|---|
| 2017/0014083 A1 | 1/2017 | Diab et al. |
| 2017/0014084 A1 | 1/2017 | Al-Ali et al. |
| 2017/0027456 A1 | 2/2017 | Kinast et al. |
| 2017/0027498 A1 | 2/2017 | Larson et al. |
| 2017/0042488 A1 | 2/2017 | Muhsin |
| 2017/0049365 A1 | 2/2017 | Perlman et al. |
| 2017/0053083 A1 | 2/2017 | Perlman |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |

FOREIGN PATENT DOCUMENTS

| | | |
|---|---|---|
| EP | 2 766 834 | 8/2014 |
| EP | 2 811 894 | 12/2014 |
| JP | 10-336064 | 12/1998 |
| JP | 2002-513602 | 5/2002 |
| JP | 2002-542493 | 12/2002 |
| JP | 2005-218036 | 8/2005 |
| JP | 2005-295375 | 10/2005 |
| JP | 2007-095365 | 4/2007 |
| JP | 2007-174051 | 7/2007 |
| JP | 2008-519635 | 6/2008 |
| JP | 2009-017959 | 1/2009 |
| JP | 2010-524510 | 7/2010 |
| JP | 2014-533997 | 12/2014 |
| WO | WO 98/029790 | 7/1998 |
| WO | WO 99/013766 | 3/1999 |
| WO | WO 00/063713 | 10/2000 |
| WO | WO 2004/056266 | 7/2004 |
| WO | WO 2004/059551 | 7/2004 |
| WO | WO 2010/135518 | 11/2010 |
| WO | WO 2011/002904 | 1/2011 |
| WO | WO 2013/056160 | 4/2013 |
| WO | WO 2013/119982 | 8/2013 |
| WO | WO 2015/054665 | 4/2015 |
| WO | WO 2015/074007 | 5/2015 |
| WO | WO 2017/040700 | 3/2017 |
| WO | WO 2018/071715 | 4/2018 |

OTHER PUBLICATIONS

Dhillon et al., "Towards the Prevention of Pressure Ulcers with a Wearable Patient Posture Monitor Based on Adaptive Accelerometer Alignment", 34th Annual International Conference of the IEEE EMBS, San Diego, CA, Aug. 28-Sep. 1, 2012, pp. 4513-4516.

Invitation to Pay Additional Fees in PCT Application No. PCT/US2016/049751, dated Jan. 18, 2017.

Li et al., "Accurate, Fast Fall Detection Using Gyroscopes and Accelerometer-Derived Posture Information", Conference Paper, Sixth International Workshop on Wearable and Implantable Body Sensor Networks, BSN 2009, Berkeley, CA, USA, Jun. 3-5, 2009, pp. 6.

Aminian et al., "Spatio-Temporal Parameters of Gait Measured by an Ambulatory System Using Miniature Gyroscopes", Journal of Biomechanics, 2002, vol. 35, pp. 689-699.

Anliker et al., "AMON: A Wearable Multiparameter Medical Monitoring and Alert System", IEEE Transactions on Information Technology in Biomedicine, vol. 8, No. 4, Dec. 2004, pp. 415-427.

Asada et al., "Mobile Monitoring with Wearable Photoplethysmographic Biosensors", IEEE Engineering in Medicine and Biology Magazine, May/Jun. 2003, pp. 28-40.

Ayello et al., "How and Why to Do Pressure Ulcer Risk Assessment", Advances in Skin & Wound Care, May/Jun. 2002, vol. 15, No. 3., pp. 125-133.

Bergstrom et al., "A Prospective Study of Pressure Sore Risk Among Institutionalized Elderly", Journal of the American Geriatrics Society, Aug. 1992, vol. 40, No. 8, pp. 747-758.

Bourke et al., "Evaluation of a Threshold-Based Tri-Axial Accelerometer Fall Detection Algoithm", Gait & Posture, vol. 26, 2007, pp. 194-199.

Campo et al., "Wireless Fall Sensor with GPS Location for Monitoring the Elderly", 30th Annual International IEEE EMBS Conference Vancouver, British Columbia, Canada, Aug. 20-24, 2008, pp. 498-501.

Caporusso et al., "A Pervasive Solution for Risk Awareness in the Context of Fall Prevention", Pervasive Health, 2009, pp. 8.

Capuano et at. "Remote Telemetry—New Twists for Old Technology." Nursing Management. vol. 26, No. 7. Jul. 1995.

Chen et al., "In-Bed Fibre Optic Breathing and Movement Sensor for Non-Intrusive Monitoring", Proceedings of SPIE vol. 7173, 2009, pp. 6.

Chen et al., "Wearable Sensors for Reliable Fall Detection", Proceedings of the 2005 IEEE Engineering in Medicine and Biology 27th Annual Conference, Shanghai, China, Sep. 1-4, 2005, pp. 3551-3554.

Degen et al., "SPEEDY: A Fall Detector in a Wrist Watch", Proceedings of the Seventh IEEE International Symposium on Wearable Computers (ISWC'03), 2003, pp. 184-187.

Di Rienzo et al., "MagIC System: a New Textile-BasedWearable Device for Biological Signal Monitoring. Applicability in Daily Life and Clinical Setting", Proceedings of the 2005 IEEE Engineer-

(56) References Cited

OTHER PUBLICATIONS ing in Medicine and Biology 27th Annual Conference Shanghai, China, Sep. 1-4, 2005, pp. 7167-7169.
Dinh et al, "A Fall and Near-Fall Assessment and Evaluation System", The Open Biomedical Engineering Journal, 2009, vol. 3, pp. 1-7.
Elmer-Dewitt, Philip, Apple's iWatch: The killer apps may be in hospitals, not health clubs, Fortune.com, Feb. 3, 2014, http://fortune.com/2014/02/03/apples-iwatch-the-killer-apps-may-be-in-hospitals-not-health-clubs/, in 4 pages.
Giansanti et al., "Assessment of Fall-Risk by Means of a Neural Network Based on Parameters Assessed by a Wearable Device During Posturography", Medical Engineering & Physics, vol. 30, 2008, pp. 367-372.
Giansanti, Daniele, "Investigation of Fall-Risk Using a Wearable Device with Accelerometers and Rate Gyroscopes", Institute of Physics Publishing, Physiological Measurement, vol. 27, 2006, pp. 1081-1090.
Grundy et al., "Telemedicine in Critical Care: An Experiment in Health Care Delivery", JACEP, Oct. 1977, vol. 6, No. 10, pp. 439-444.
Grundy et al., "Telemedicine in Critical Care: Problems in Design, Implementation and Assessment", Jul. 1982, vol. 10, No. 7, pp. 471-475.
Gunningberg et al., "Accuracy in the Recording of Pressure Ulcers and Prevention after Implementing an Electronic Health Record in Hospital Care", Quality Safe Health Care, 2008, vol. 17, pp. 281-285.
Gunningberg et al., "Improved Quality and Comprehensiveness in Nursing Documentation of Pressure Ulcers after Implementing an Electronic Health Record in Hospital Care", Journal of Clinical Nursing, 2009, vol. 18, pp. 1557-1564.
Harada et al., "Portable Orientation Estimation Device Based on Accelerometers, Magnetometers and Gyroscope Sensors for Sensor Network", IEEE Conference on Multisensor Fusion and Integration for Intelligent Systems 2003, 2003, pp. 191-196.
Hwang et al., "Development of Novel Algorithm and Real-time Monitoring Ambulatory System Using Bluetooth Module for Fall Detection in the Elderly", Proceedings of the 26th Annual International Conference of the IEEE EMBS, Sep. 1-5, 2004, pp. 2204-2207.
International Preliminary Report on Patentability & Written Opinion in PCT Application No. PCT/US2013/025384, dated Aug. 21, 2014.
International Search Report & Written Opinion in PCT Application No. PCT/US2013/025384, dated Aug. 6, 2013.
Kang et al., "A Wrist-Worn Integrated Health Monitoring Instrument with a Tele-Reporting Device for Telemedicine and Telecare", IEEE Transaction on Instrumentation and Measurement, vol. 55, No. 5, Oct. 2006, pp. 1655-1661.
Kärki et al., "Pressure Mapping System for Physiological Measurements", XVIII IMEKO World Congress, Metrology for a Sustainable Development, Sep. 17-22, 2006, Rio de Janeiro, Brazil, pp. 5.
Lindemann et al., "Evaluation of a Fall Detector Based on Accelerometers: A Pilot Study", Medical & Biological Engineering & Computing, vol. 43, 2005, pp. 548-551.
Linder-Ganz et al., "Real-Time Continuous Monitoring of Sub-Dermal Tissue Stresses Under the Ischial Tuberosities in Individuals with Spinal Cord Injury", Proceedings of the ASME 2008 Summer Bioengineering Conference (SBC2008), Jun. 25-29, 2008, Marriott Resort, Marco Island, Florida, pp. 2.
Luo et al., "A Dynamic Motion Pattern Analysis Approach to Fall Detection", 2004 IEEE International Workshop on Biomedical Circuits & Systems, Dec. 1-3, 2004, pp. S2.1-5-S2.1-8.
Mathie et al., "A System for Monitoring Posture and Physical Activity Using Accelerometers", Engineering in Medicine and Biology Society, 2001. Proceedings of the 23rd Annual International Conference of the IEEE, Oct. 25-28, 2001, pp. 3654-3657.
McInerney, Joan A., "Reducing Hospital-Acquired Pressure Ulcer Prevalence Through a Focused Prevention Program", Advances in Skin & Wound Care, vol. 21, No. 2, Feb. 2008, pp. 75-78.
Merbitz et al., "Wheelchair Push-ups: Measuring Pressure Relief Frequency", Archives of Physical Medicine and Rehabilitation, vol. 66, No. 7, Jul. 1985, pp. 433-438.
Narayanan et al., "Falls Management: Detection and Prevention, Using a Waist-Mounted Triaxial Accelerometer", Proceedings of the 29th Annual International Conference of the IEEE EMBS Cité Internationale, Lyon, France, Aug. 23-26, 2007, pp. 4037-4040.
Noury, Norbert, "A Smart Sensor for the Remote Follow Up of Activity and Fall Detection of the Elderly", 2nd Annual International IEEE-EMBS Special Topic Conference on Microtechnologies in Medicine & Biology, May 2-4, 2002, pp. 314-317.
Nyan et al., "A Wearable System for Pre-Impact Fall Detection", Journal of Biomechanics, vol. 41, 2008, pp. 3475-3481.
Nyan et al., "Garment-Based Detection of Falls and Activities of Daily Living Using 3-Axis MEMS Accelerometer", Institute of Physics Publishing, International MEMS Conference 2006, Journal of Physics: Conference Series 34, 2006, pp. 1059-1067.
O'Donovan et al., "A Context Aware Wireless Body Area Network", Pervasive Health, 2009, pp. 8.
Pérolle et al., "Automatic Fall Detection and Activity Monitoring for Elderly", Jan. 2007, pp. 6.
Po et al., "Overview of MEMSWear II—Incorporating MEMS Technology Into Smart Shirt for Geriatric Care", Institute of Physics Publishing, International MEMS Conference 2006, Journal of Physics: Conference Series 34, 2006, pp. 1079-1085.
Prado et al., "Distributed Intelligent Architecture for Falling Detection and Physical Activity Analysis in the Elderly", Proceedings of the Second Joint EMBS/BMES Conference, Oct. 23-26, 2002, pp. 1910-1911.
Rithalia et al., "Quantification of Pressure Relief Using Interface Pressure and Tissue Perfusion in Alternating Pressure Air Mattresses", Archives of Physical Medicine and Rehabilitation, vol. 81, Oct. 2000, pp. 1364-1369.
Rysavy, Peter, "Making the Call with Two-Way Paging", Network Computing, Published Jan. 15, 1997, www.rysavy.com/Articles/twoway.htm, pp. 5.
Sakai et al., "Continuous Monitoring of Interface Pressure Distribution in Intensive Care Patients for Pressure Ulcer Prevention", Journal of Advanced Nursing, vol. 65, No. 4, 2009, pp. 809-817.
Spillman Jr., et al., "A 'Smart' Bed for Non-Intrusive Monitoring of Patient Physiological Factors", Measurement Science and Technology, Aug. 2004, vol. 15, No. 8, pp. 1614-1620.
Wachter et al., "The Employment of an Iterative Design Process to Develop a Pulmonary Graphical Display", Journal of the American Medical Informatics Association, vol. 10, No. 4, Jul./Aug. 2003, pp. 363-372.
Webster, John G., "A Pressure Mat for Preventing Pressure Sores", IEEE Engineering in Medicine & Bioloogy Society 11th Annual International Conference, 1989, pp. 2.
Williams et al., "A Remote Electronic Monitoring System for the Prevention of Pressure Sores", Proceedings of the 19th International Conference, IEEE/EMBS Oct. 30-Nov. 2, 1997, Chicago, IL, pp. 1076-1079.
Wu et al., "Portable Preimpact Fall Detector With Inertial Sensors", IEEE Transactions on Neural Systems and Rehabilitation Engineering, vol. 16, No. 2, Apr. 2008, pp. 178-183.
International Search Report & Written Opinion in PCT Application No. PCT/US2016/049751, dated Mar. 13, 2017.
International Preliminary Report on Patentability & Written Opinion in PCT Application No. PCT/US2016/049751, dated Mar. 6, 2018.
International Search Report & Written Opinion in PCT Application No. PCT/US2017/056405, dated Jan. 26, 2018.

\* cited by examiner

PATIENT-WORN WIRELESS PHYSIOLOGICAL SENSOR

INCORPORATION BY REFERENCE TO ANY PRIORITY APPLICATIONS

The present application claims priority benefit under 35 U.S.C. § 119(e) to U.S. Provisional Application No. 62/212,467, filed Aug. 31, 2015, U.S. Provisional Application No. 62/212,472, filed Aug. 31, 2015, U.S. Provisional Application No. 62/212,484, filed Aug. 31, 2015, and U.S. Provisional Application No. 62/212,480, filed Aug. 31, 2015, which are hereby incorporated by reference herein in entirety.

FIELD OF THE DISCLOSURE

The present disclosure relates to the field of patient monitoring. More specifically, the disclosure describes among other things a wearable sensor that measures a patient's position, orientation, and movement and wirelessly communicates the measured information to a patient monitoring system.

BACKGROUND

In clinical settings, such as hospitals, nursing homes, convalescent homes, skilled nursing facilities, post-surgical recovery centers, and the like, patients are frequently confined to bed for extended periods of time. Sometimes the patients are unconscious or sedated to such an extent that they have limited ability to change or control their position in the bed. These patients can be at risk of forming pressure ulcers, which pose a serious risk to the patient's health and well-being. Pressure ulcers, which may also be referred to as "bed sores," "pressure sores," and "decubitus ulcers," comprise injury to a patient's skin, and often the underlying tissue, which results from prolonged pressure forces applied to a site on the patient's body. Frequently, pressure ulcers develop on skin that covers bony areas of the body which have less muscle and/or fat tissue below the surface to distribute pressure applied thereto resulting from prolonged contact with the surface of a bed or chair. Examples of such body locations include the back or side of the head, shoulders, shoulder blades, elbows, spine, hips, lower back, tailbone, heels, ankles, and skin behind the knees.

Pressure ulcers are caused by application of pressure at an anatomical site that occludes blood flow to the skin and other tissue near the location. Sustained pressure between a structural surface (such as a bed) and a particular point on the patient's body can restrict blood flow when the applied pressure is greater than the blood pressure flowing through the capillaries that deliver oxygen and other nutrients to the skin and other tissue. Deprived of oxygen and nutrients, the skin cells can become damaged, leading to tissue necrosis in as few as 2 to 6 hours. Despite commonly occurring in elderly and mobility-impaired populations, hospital-acquired pressure ulcers are considered to be preventable and have been termed "never events." Insurers have imposed restrictions on the amount they will reimburse a hospital for pressure ulcer treatment, and state and federal legislation now requires hospitals to report the occurrence of pressure ulcers in their facilities.

Risk factors for pressure ulcers can be categorized as modifiable and non-modifiable. Modifiable risk factors include actions that healthcare providers can take, while non-modifiable risk factors include aspects of patient health and behavior. It is valuable to document such non-modifiable risk factors so that caregivers can identify and attend to patients at risk of developing pressure ulcers. It is recommended that caregivers develop a documented risk assessment policy to predict the risk of a patient developing a pressure ulcer. Such an assessment can encompass all aspects of a patient's health and environment, and may employ commonly used measures in the field, such as the Braden and Norton scales. The risk assessment tool may be used to direct preventative strategies not only when a patient is at rest in his or her bed, but also when undergoing surgery.

Additional factors that can contribute to the formation of pressure ulcers include friction and shear forces. Friction can occur when skin is dragged across a surface which can happen when patients are moved, especially when the skin is moist. Such frictional forces can damage the skin and make it more vulnerable to injury, including formation of a pressure ulcer. A shear is when two forces move in opposite directions. For example, when the head portion of a bed is elevated at an incline, the patient's spine, tailbone, and hip regions tend to slide downward due to gravity. As the bony portion of the patient's body moves downward, the skin covering the area can stay in its current position, thereby pulling in the opposite direction of the skeletal structure. Such shear motion can injure the skin and blood vessels at the site, causing the skin and other local tissue to be vulnerable to formation of a pressure ulcer.

An established practice for patients at risk of forming pressure ulcers is to follow a turning protocol by which the patient is periodically repositioned, or "turned" to redistribute pressure forces placed on various points of the patient's body. Individuals at risk for a pressure ulcer are be repositioned regularly. It is commonly suggested that patients be repositioned every 2 hours at specific inclination angles, and that the method of doing so minimizes the amount of friction and shear on the patient's skin. A repositioning log can be maintained and include key information, such as the time, body orientation, and outcome.

Pressure ulcer prevention programs have been effective and can reduce long-term costs associated with treatment. A 2002 study employed a comprehensive prevention program in two long-term care facilities, costing $519.73 per resident per month. Results of the program revealed pressure ulcer prevalence to be reduced by 87% and 76% in the two facilities. A later study found that prevention strategies were able to reduce pressure ulcer prevalence from 29.6% to 0% in a medical intensive care unit, and from 9.2% to 6.6% across all units of the hospital. These interventions employed strategies such as manual patient repositioning and logging, tissue visualization and palpation, pressure-reducing mattresses, and use of risk assessment tools.

Turning protocols, however, do not take into consideration position changes made by the patient between established turn intervals, which are neither observed nor recorded. Thus it is possible that in some circumstances, the act of following a turn protocol can have an unintended negative clinical effect.

SUMMARY

This disclosure describes, among other things, embodiments of systems, devices, and methods for monitoring the position and orientation of a patient at risk of forming one or more pressure ulcers.

One aspect of the present disclosure comprises a patient turn and movement monitoring system configured to help manage a patient that is at risk of forming one or more pressure ulcers. Some embodiments of the patient turn and monitoring system include a patient-worn, wireless sensor having one or more sensors configured to obtain information describing the patient's orientation and to wirelessly transmit information indicative of the sensed orientation information. The system also includes a patient monitor configured to receive, store, and process the information transmitted by the wireless sensor and to display and transmit information (or data) indicative of the patient's orientation to help caregivers manage the patient's risk of formation of one or more pressure ulcers. The patient turn and movement monitoring system can identify the present orientation of the patient and determine how long the patient has been in the present orientation. If the patient remains in an orientation beyond a predefined, clinician-prescribed patient orientation duration, the system can notify the patient and/or caretakers that the patient is due to be repositioned. In certain embodiments, a patient orientation duration timer is used to monitor such orientation times. In certain embodiments of the disclosed patient turn and movement monitoring system, a signal repeater, located within reception range of the wireless sensor, is used to receive and forward the information indicative of the sensed orientation information from the wireless sensor to a network-based processing node.

Another aspect of the present disclosure includes a wireless sensor including one or more sensors configured to obtain position, orientation, and motion information from the patient. The one or more sensors can include an accelerometer, a gyroscope, and a magnetometer, which are configured to determine the patient's position and orientation in three-dimensional space. The wireless sensor is configured to wirelessly transmit the sensor data, and/or information representative of the sensor data, to a patient monitor. The patient monitor can be configured to process the received information, to display information indicative of, or derived from the received data, and to transmit information—including displays, alarms, alerts, and notifications—to a multi-patient monitoring system which may be located, for example, at a nurse's station.

Another aspect of the present disclosure is directed to a system and method for associating the wireless sensor with a patient monitor. In some embodiments, the wireless sensor includes an activation tab which, when removed, activates the wireless sensor. Upon activation, a wireless transceiver in the wireless sensor emits a low-power pairing signal having a pairing signal transmission range of up to approximately three inches. In some embodiments, the wireless sensor has a switch or button which, when depressed, places the wireless sensor in a pairing mode of operation, causing the wireless sensor to emit the low-power pairing signal. When the patient monitor is within range of the wireless sensor (e.g., within the about three-inch range), the wireless sensor and the patient monitor associate, thereby configuring the wireless sensor and patient monitor to communicate with each other. Once the pairing between the wireless sensor and the patient monitor is completed, the wireless sensor changes into a patient parameter sensing mode of operation in which the wireless sensor transmits a patient parameter sensing signal. The patient parameter sensing signal has a patient signal transmission range that is substantially greater than the pairing signal transmission range. The wireless sensor is then in condition to be placed on the patient.

In some aspects of the present disclosure the patient's position and orientation are monitored and recorded. Once the wireless sensor is affixed to the patient's body, such as, for example, the patient's torso, sensor data corresponding to the patient's motion (e.g., acceleration and angular velocity) are obtained, pre-processed, and transmitted to the patient monitor. The patient monitor stores and further processes the received data to determine the patient's orientation. Illustratively, the patient monitor can determine whether the patient is standing, sitting, or lying down in the prone, supine, left side, or right side positions.

In some embodiments, the patient monitor determines the precise orientation of the patient's body. For example, the patient monitor can determine the degree to which the patient's body is inclined, vertically and/or horizontally, thereby generating an accurate description of the patient's position relative to the support structure (such as a bed) upon which the patient lies.

In another aspect of the present disclosure the patient monitor stores the determined position and orientation information and keeps track of how long the patient remains in each determined position, thereby creating a continuous record of the patient's positional history. The patient monitor analyzes and processes the stored data to provide clinically-relevant, actionable information to the patient's care providers. Illustratively, the patient monitor counts the number of in-bed turns performed by the patient and monitors and displays the amount of time that has elapsed since the patient last turned. When the elapsed time exceeds a clinician-defined duration (e.g., two hours), the patient monitor displays an indication that the maximum time between patient turns has been exceeded. The patient monitor can also transmit a notification to one or more clinicians responsible for caring for the patient via, for example, a multi-patient monitoring system, a clinician notification device, or the like. The patient monitor can also determine and display statistical information, such as the average, minimum, and maximum amount of time between turns for a given clinician-defined time period, such as for example, twenty-four hours. The patient monitor can also determine and display the number of turns in the same position and orientation over a clinician-defined period of time. Similarly, the patient monitor can display the total amount of time the patient remained in each specific position within a clinician-defined period. Moreover, the patient monitor can determine the frequency and duration of periods during which the patient remained in clinically-defined acceptable positions.

In yet another aspect of the present disclosure the patient monitor determines the mobility status of the patient, e.g., whether the patient is ambulatory, standing, sitting, reclining, or falling. In certain aspects, the wireless monitoring system can include an alert system to alert the caregiver that the patient is falling, getting out of bed, or otherwise moving in a prohibited manner or in a manner that requires caregiver attention. The alert can be an audible and/or visual alarm on the monitoring system, or the alert can be transmitted to a caregiver (e.g., nurses' station, clinician device, pager, cell phone, computer, or otherwise). Illustratively, the patient monitor can display the patient's mobility status and transmit a notification that the patient is active and away from the bed. In some circumstances, the patient monitor can determine whether the patient contravenes a clinician's order, such as, for example, instructions to remain in bed, or to walk to the bathroom only with the assistance of an attendant. In such circumstances, a notification, alert, or alarm can be transmitted to the appropriate caregivers.

In certain aspects, the information received by the wireless sensor can be used to create a time-sequenced representation of the patient's movement. This representation can be displayed on the patient monitor or transmitted to a nurses' station or other processing nodes to enable the caregiver to monitor the patient. The time-sequenced representation can be viewed in real time and/or be recorded for playback. For example, if an alarm alerts the caregiver that the patient has fallen out of bed, the caregiver can access and review the historical sequence of the patient's movements prior to and during that period of time.

Another aspect of the present disclosure is directed to predicting a patient's risk of falling based on the patient's gait and other information (such as, for example, the patient's current medication regimen). When the patient monitor determines that the patient's risk of falling is above a predetermined threshold, the patient monitor can issue an alarm or alert to notify care providers of the identified risk in an effort to anticipate and therefore prevent a patient fall. Additionally, the patient monitor can determine when a patient has fallen and issue the appropriate alarms and alerts to summon care provider assistance.

In an aspect of the present disclosure the patient monitor accesses the patient's health records and clinician input via a network. Illustratively, the patients' positional history data, analyzed in view of the patient's health records, may reveal or suggest a turning protocol (or other treatment protocol) that will likely yield favorable clinical outcomes for the particular patient. Accordingly, the patient monitor analyzes the accessed information in conjunction with the received information from the wireless sensor to determine a recommended patient turn protocol (or other treatment protocol) for the patient.

In still another aspect of the present disclosure, the patient monitor assesses caregiver and facility compliance with the clinician-defined patient turn protocol established for the patient. For example, the patient monitor can identify the number of times that the patient remains in a position for a period greater than the prescribed duration, indicating a patient turn protocol violation, as well as the length of each such overexposure. The patient monitor can also track the clinician's response time upon issuance of a notification, alert, or alarm.

According to another aspect of the present disclosure, care provider workflow productivity, efficiency, and effectiveness can be determined, based on aggregated positional history data corresponding to multiple patients wherein each patient is equipped with the disclosed wireless sensor. Additionally, care for patients in a particular location, such as a hospital ward or nursing home floor where the ratio of patients to staff is relatively high, can be prioritized based on the determined risk of formation of pressure ulcers. Thus, patients determined to have the highest risk are designated to receive attention first.

In yet another aspect of the present disclosure, the wireless sensor includes sensors to obtain additional physiological measurements from the patient. For example, the wireless sensor can include a temperature sensor configured to measure the patient's body core body temperature by insulating the patient's skin surface around the temperature sensor. As a result of the insulation surrounding the temperature sensor, the natural temperature difference between the patient's skin surface and body core reach equilibrium, thereby arriving at the patient's body core temperature (which is typically higher in temperature than the patient's skin surface). The wireless sensor can also include an acoustic respiration sensor configured to sense vibrational motion generated by the patient's chest. The acoustic respiration sensor is configured to mechanically transmit the sensed vibrations through rigid structures of the device to the accelerometer. Processing of the accelerometer signal can provide, among other things, the patient's respiration and heart rates. An electrocardiogram (ECG) sensor, configured to sense electrical signals from two or more electrodes in electrical contact with the patient's chest may also be included in the wireless sensor. The ECG signal can be processed to detect arrhythmias, such as bradycardia, tachyarrhythmia, ventricular fibrillation and the like. Additionally, the accelerometer signal (containing information indicative of the mechanically-transmitted vibrations from the acoustic respiration sensor) and/or the ECG signal can be processed to identify respiratory distress or dysfunction, including without limitation, snoring, coughing, choking, wheezing, apneic events, and airway obstruction.

In another aspect of the present disclosure, the patient monitor can determine a score that describes the patient's wellness/sickness state, which may also be referred to as a "Halo Index." Illustratively, the patient monitor accesses and analyzes the patient's health records, clinician input, positional history data provided by the wireless sensor, surface structure pressure data, and other physiological parameter data collected and provided by the wireless sensor (such as, by way of non-limiting example, the patient's temperature, respiration rate, heart rate, ECG signal, and the like) to assess the patient's overall health condition.

In an aspect of the present disclosure, the patient monitor accesses information provided by the patient's support structure (e.g., bed, mattress, bed sheet, mattress pad, and the like) to determine the extent of pressure forces exerted on particular anatomical sites of the patient's body. Illustratively, the patient's support structure can be configured with an array of pressure sensors that measure the pressure force exerted on the support structure by the patient at specific locations. The patient monitor can analyze the patient's postural history data in conjunction with the information provided by the support structure to determine a likelihood of pressure ulcer formation at a specific anatomical location based on the measured amount of pressure exerted on the anatomical location multiplied by the amount of time the anatomical location has been under such pressure. When the evaluated risk exceeds a predetermined threshold, the patient monitor can issue an alarm and/or an alert to reposition the patient so as to avoid formation of a pressure ulcer in the specified anatomical location. Additionally, the patient monitor can suggest particular positions and/or a patient turn protocol based on the combined analysis of pressure force exerted and length of time under such pressure.

For purposes of summarizing the disclosure, certain aspects, advantages, and novel features have been described herein. Of course, it is to be understood that not necessarily all such aspects, advantages, or features will be embodied in any particular embodiment.

BRIEF DESCRIPTION OF THE DRAWINGS

Various embodiments will be described hereinafter with reference to the accompanying drawings. The drawings and the associated descriptions are provided to illustrate embodiments of the present disclosure and do not limit the scope of the claims. In the drawings, similar elements have similar reference numerals.

DETAILED DESCRIPTION

Embodiments of the present disclosure will now be described with reference to the accompanying figures, wherein like numerals refer to like elements throughout. The following description is merely illustrative in nature and is in no way intended to limit the disclosure, its application, or uses. It should be understood that steps within a method may be executed in different order without altering the principles of the present disclosure. Furthermore, embodiments disclosed herein can include several novel features, no single one of which is solely responsible for its desirable attributes or which is essential to practicing the systems, devices, and methods disclosed herein.

The present disclosure relates to systems, devices, methods, and computer-readable media to monitor and manage the position, orientation, and movement of a patient who is at risk of forming one or more pressure ulcers. In one embodiment, the system comprises a patient-worn, wireless sensor including one or more sensors configured to obtain position, orientation and movement information from the patient. The one or more sensors can include one or more accelerometers, gyroscopes, and magnetometers (i.e., compasses). Illustratively, the sensors continuously or periodically (e.g., every second) obtain information that describes the patient's orientation in three dimensions. The wireless sensor includes a processor that is configured to process the obtained sensor information. The wireless sensor also includes a transceiver configured to wirelessly transmit the processed sensor data, and/or information representative of the sensor data, to a patient monitor (or other processing device) for further processing. The patient monitor can be configured to store and further process the received information, to display information indicative of or derived from the received data, and to transmit information—including displays, alarms, alerts, and notifications—to other patient care systems including a multi-patient monitoring system which may be accessible from, for example, a nurses' station.

Figure 1A:
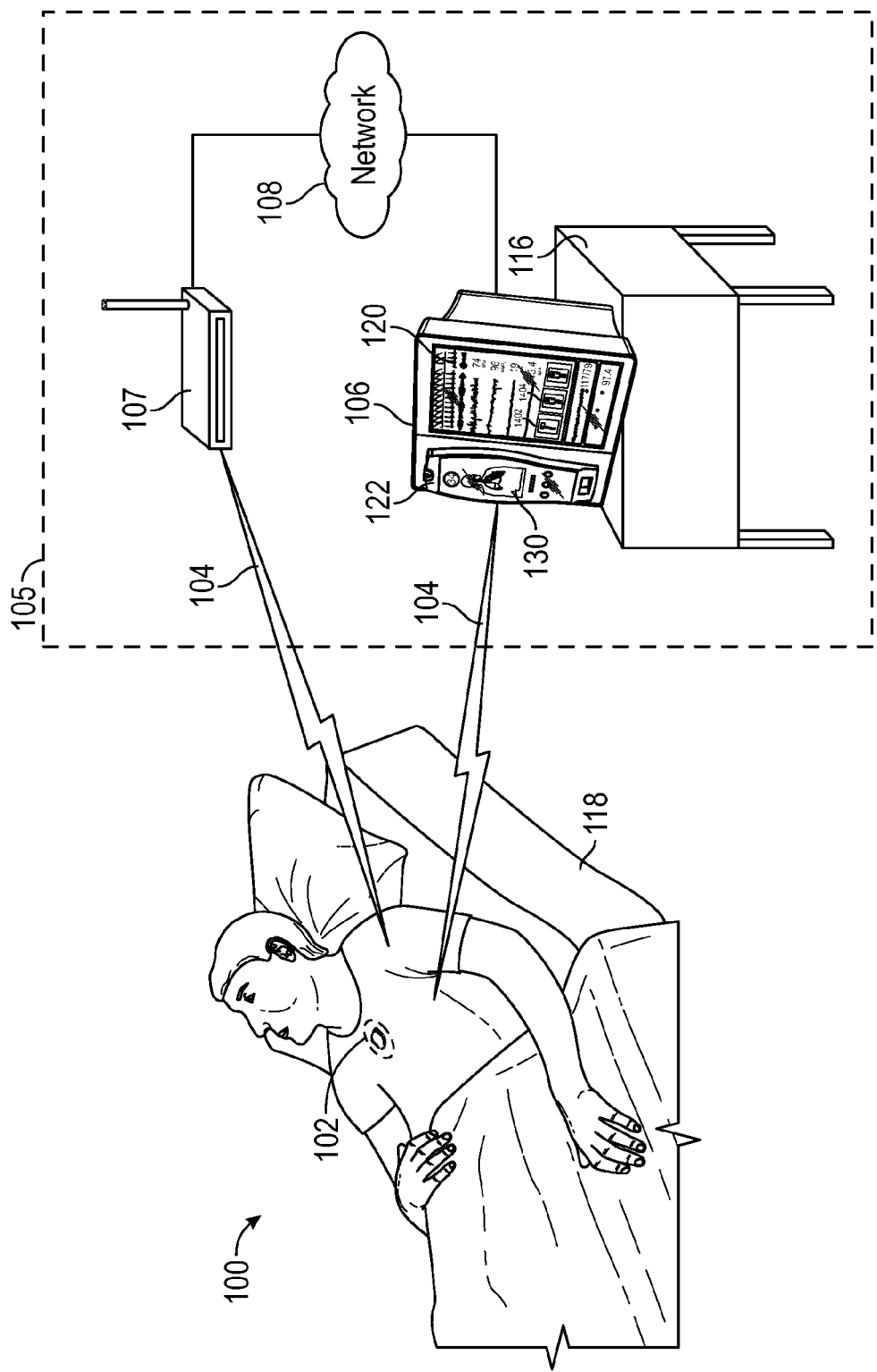
FIG. 1A is a perspective view of an embodiment of the disclosed patient monitoring system including a patient-worn wireless sensor in proximity to a patent monitor.

FIG. 1A is a perspective illustration of an embodiment of the disclosed patient monitoring system 100 in a clinical setting. The patient monitoring system 100 includes a wireless sensor 102 worn by a patient, in proximity to a patient monitor 106 located on a table 116 at the side of the patient's bed 118. The wireless sensor 102 may also be referred to herein as "a wireless physiological sensor 102," "a patient-worn sensor 102," "a movement sensor 102," and "a wearable wireless sensor 102." The wireless sensor 102 includes one or more sensors configured to measure the patient's position, orientation, and motion. In some embodiments, the wireless sensor 102 includes an accelerometer configured to measure linear acceleration of the patient and a gyroscope configured to measure angular velocity of the patient. The measured linear acceleration and angular velocity information can be processed to determine the patient's orientation in three dimensions. In some embodiments, a magnetometer is included in the wireless sensor 102 to measure the Earth's gravitational field. Information measured by the magnetometer can be used to improve accuracy of the determined orientation of the patient.

The wireless sensor 102 also includes a wireless transceiver 206 (shown in FIGS. 2A and 2B) which can transmit to the patient monitor 106 information representative of sensor data obtained by the wireless sensor 102 from the patient. Advantageously, the patient is not physically coupled to the bedside patient monitor 106 and can therefore move freely into different positions on the bed 118.

In accordance with certain embodiments of the present disclosure, the wireless sensor 102 is affixed to the skin of the patient's body under the patient's garment as reflected in FIG. 1A by the phantom drawing of the wireless sensor 102. More particularly, the wireless sensor 102 can be placed on the patient's chest over the patient's manubrium, the broad upper portion of the sternum. In this position, the wireless sensor 102 is approximately centered relative to the longitudinal axis of the patient's body and near the patient's center of mass, a position that is useful in determining the patient's orientation when, for example, the patient is in bed.

The wireless sensor 102 can be affixed to the patient's skin using any form of medically-appropriate adherent material, including a pressure-sensitive adhesive that is coated or applied to the bottom surface of the wireless sensor 102. One skilled in the art will appreciate that many other materials and techniques can be used to affix the wireless sensor 102 to the patient without departing from the scope of the present disclosure.

Frequently in clinical settings, multiple medical sensors are attached or adhered to a patient to concurrently monitor multiple physiological parameters. Some examples of medical sensors include, but are not limited to, position, orientation, and movement sensors, temperature sensors, respiration sensors, heart rate sensors, blood oxygen sensors (such as pulse oximetry sensors), acoustic sensors, EEG sensors, ECG sensors, blood pressure sensors, sedation state sensors, to name a few. Typically, each sensor that is attached to a patient transmits, often by cable, the obtained physiological data to a nearby monitoring device configured to receive and process the sensor data, and transform it into clinical information to be used by the care providers to monitor and manage the patient's condition. When a patient is concurrently monitored by several physiological sensors, the number of cables and the number of bedside monitoring devices used can be excessive and can limit the patient's freedom of movement and impede care providers' access to the patient. The cables connecting the patient to the bedside monitoring devices can also make it more difficult to move the patient from room to room or to switch to different bedside monitors.

Advantageously, the disclosed wireless sensor 102 can transmit data, wirelessly, to a patient data processing environment 105 in which the sensor data can be processed using one or more processing capabilities. As illustrated in FIG. 1A, the wireless sensor 102 transmits data via a wireless communications link 104. The wireless communications link 104 can be received by the bedside patient monitor 106, and/or by an extender/repeater 107. Both the patient monitor 106 and expander/repeater 107 provide access, by way of high-speed and reliable communications interfaces, to the patient data processing environment 105. For illustration purposes, both the patient monitor 106 and the extender/repeater 107 are illustrated in FIG. 1A. However, typically only one such device is required to establish a wireless connection between the wireless sensor 102 and the patient data processing environment 105. The wireless communications link 104 can use any of a variety of wireless technologies, such as Wi-Fi (802.11x), Bluetooth, ZigBee, cellular telephony, infrared, RFID, satellite transmission, proprietary protocols, combinations of the same, and the like. The wireless sensor 102 can be configured to perform telemetry functions, such as measuring and reporting position, orientation, and movement information about the patient. According to one embodiment, the wireless sensor 102 uses the Bluetooth wireless communications standard to communicate wirelessly with the patient monitor 106.

The extender/repeater 107 can receive sensor data from the wireless sensor 102 by way of the wireless communications link 104 and forward the received sensor data, via the network 108, to one or more processing nodes within the patient data processing environment 105. For example, the extender/repeater 107 can forward the received sensor data to a patient monitor 106 that might be located beyond the range of the wireless communications link 104 of a particular wireless sensor 102. Alternatively, the extender/repeater 107 can route the sensor data to other processing nodes within the patient data processing environment 105, such as, for example, a multi-patient monitoring system 110 or a nurses' station system 113. A skilled artisan will appreciate that numerous processing nodes and systems can be used to process the data transmitted by the wireless sensor 102.

FIG. 1A also illustrates an embodiment of the patient monitor 106, which may also be referred to herein as "a processing device 106," "a portable computing device 106," and "a patient monitoring device 106." Examples of a patient monitor 106 are disclosed in U.S. Pat. Pub. Nos. 2013/0262730 and 2015/0099955, assigned to the assignee of the present disclosure, and which are incorporated by reference herein in their entirety. The patient monitor 106 is a processing device, and therefore includes the necessary components to perform the functions of a processing device, including at least one processor, a memory device, a storage device, input/output devices, and communications connections, all connected via one or more communication buses. Thus, in certain embodiments, the patient monitor 106 is configured to process the sensor data provided by the wireless sensor 102. In other embodiments, processing of the sensor data can be performed by other processing nodes within the patient data processing environment 105. The patient monitor 106 is configured to wirelessly communicate with the wireless sensor 102. The patient monitor 106 includes a display 120, and a docking station, which is configured to mechanically and electrically mate with a portable patient monitor 122 also having a display 130. The patient monitor 106 is housed in a movable, mountable, and portable housing formed in a generally upright, inclined shape configured to rest on a horizontal flat surface, as shown in FIG. 1A. Of course, a person skilled in the art will appreciate that the housing can be affixed in a wide variety of positions and mountings and can comprise a wide variety of shapes and sizes.

In an embodiment, the display 120, alone or in combination with the display 130 of the portable patient monitor 122, may present a wide variety of measurement and/or treatment data in numerical, graphical, waveform, or other display indicia. For example, the display 120 can display a variety of patient-specific configurations and/or parameters, such as the patient's weight, age, type of treatment, type of disease, type of medical condition, nutrition, hydration and/or length of stay, among others. In an embodiment, the display 120 occupies much of a front face of the housing, although an artisan will appreciate the display 120 may comprise a table or tabletop horizontal configuration, a laptop-like configuration, or the like. Other embodiments may include communicating display information and data to a tablet computer, smartphone, television, or any display system recognizable to an artisan. Advantageously, the upright inclined configuration of the patient monitor 106, as illustrated in FIG. 1A, displays information to a caregiver in an easily viewable manner.

The portable patient monitor 122 of FIG. 1A may advantageously include an oximeter, co-oximeter, respiratory monitor, depth of sedation monitor, noninvasive blood pressure monitor, vital signs monitor or the like, such as those commercially available from Masimo Corporation of Irvine, Calif., and/or disclosed in U.S. Pat. Pub. Nos. 2002/0140675, 2010/0274099, 2011/0213273, 2012/0226117, 2010/0030040; U.S. patent application Ser. Nos. 61/242,792, 61/387457, 61/645,570, 13/554,908 and U.S. Pat. Nos. 6,157,850, 6,334,065, the contents of which are incorporated herein by reference in their entireties. The portable patient monitor 122 may communicate with a variety of noninvasive and/or minimally invasive devices such as, by way of non-limiting example, wireless sensor 102, optical sensors with light emission and detection circuitry, acoustic sensors, devices that measure blood parameters from a finger prick, cuffs, ventilators, and the like. The portable patient monitor 122 may include its own display 130 presenting its own display indicia. The display indicia may change based on a docking state of the portable patient monitor 122. When undocked, the display 130 may include parameter information and may alter its display orientation based on information provided by, for example, a gravity sensor or an accelerometer. Although disclosed with reference to particular portable patient monitors 122, an artisan will recognize from the disclosure herein there is a large number and wide variety of medical devices that may advantageously dock with the patient monitor 106.

Figure 1B:
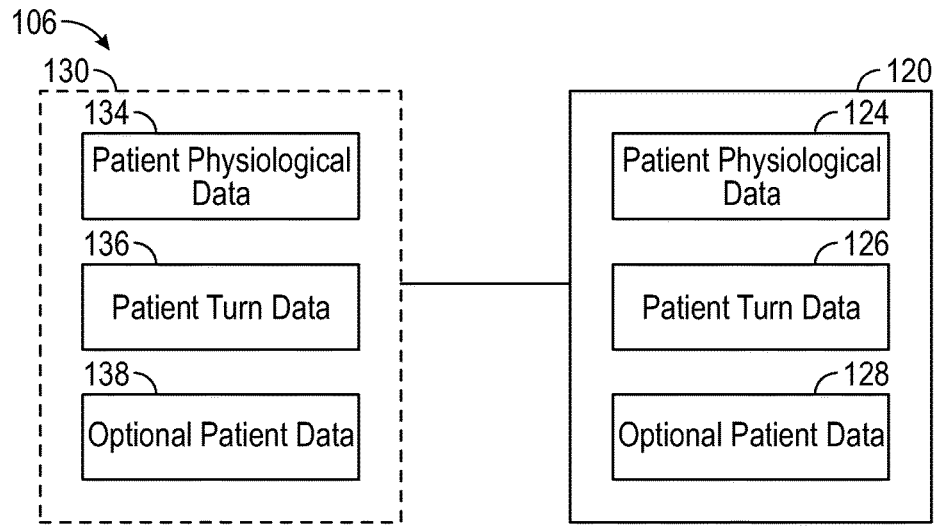
FIG. 1B is a functional block diagram of an embodiment of the display of the disclosed patient monitor.

FIG. 1B is a functional block diagram of an embodiment of the display 120 of the disclosed patient monitor 106 and the display 130 of the portable patient monitor 122. Display 120 of the patient monitor 106 can be configured to present patient physiological data 124, patient turn data 126, and/or additional, optional patient data 128. Patient physiological data can include, by way of non-limiting example, oxygen saturation, pulse rate, respiration rate, fractional arterial oxygen saturation, total hemoglobin, plethysmograph variability index, methemoglobin, carboxyhemoglobin, perfusion index, and oxygen content. Advantageously, the display 120 is configurable to permit the user to adjust the manner by which the physiologic parameters 124, patient turn data 126, and optional patient data 128 are presented on the display 120. In particular, information of greater interest or importance to the clinician may be displayed in larger format and may also be displayed in both numerical and graphical formats to convey the current measurement as well as the historical trend of measurements for a period of time, such as, for example, the preceding hour.

As illustrated by dotted lines in FIG. 1B, the display 130 of the portable patient monitor 130 is an optional feature of the patient monitor 106 which may be configured to present patient physiological data 134, patient turn data 136, and additional, optional patient data 138.

Figure 1C:
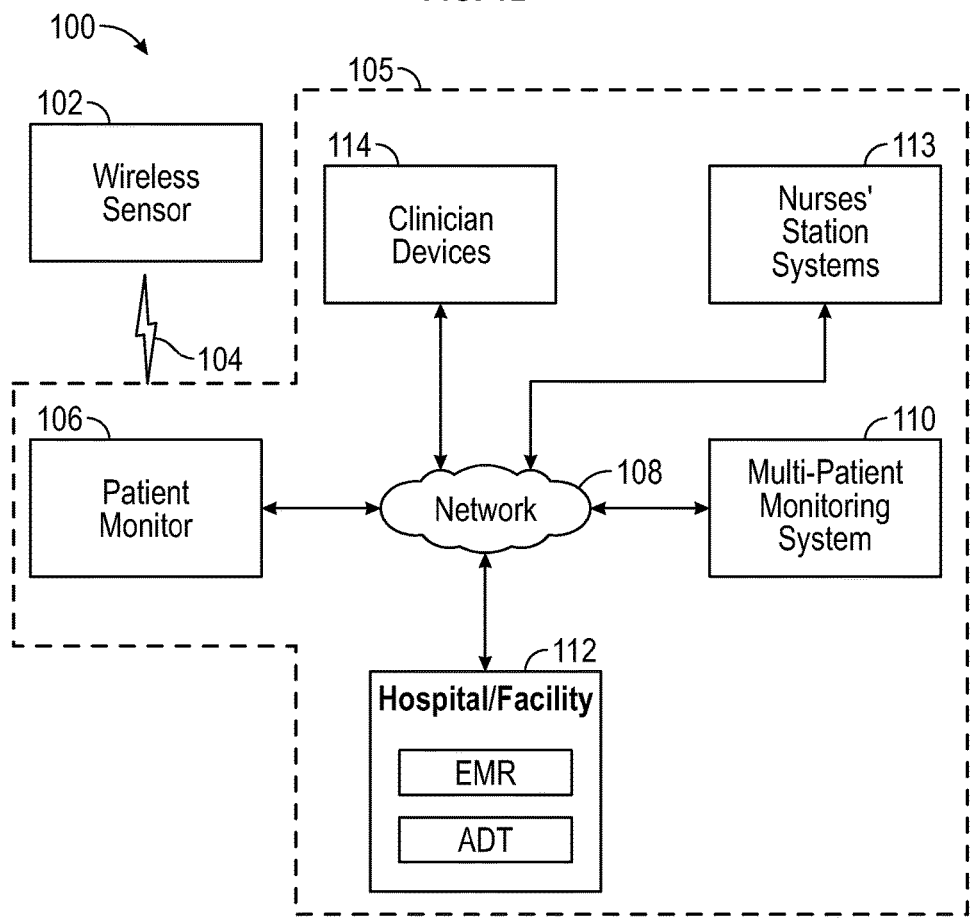
FIG. 1C is a functional block diagram of an embodiment of the disclosed patient monitoring system.

FIG. 1C is a simplified functional block diagram of an embodiment of the disclosed patient monitoring system 100. The system includes the patient-worn wireless sensor 102 having one or more sensors, a wireless communications link 104, through which sensor data from the wireless sensor 102 accesses the patient data processing environment 105 which includes a patient monitor 106, a communications network 108, a multi-patient monitoring system 110, a hospital or facility information system 112, one or more nurses' station systems 113, and one or more clinician devices 114. An artisan will appreciate that numerous other computing systems, servers, processing nodes, display devices, printers, and the like can be included in the disclosed patient monitoring system 100.

The wireless sensor 102 is worn by a patient who has been determined to be at risk of forming one or more pressure ulcers, e.g., a patient who is confined to bed for an extended period of time. The wireless sensor 102 is capable of monitoring on a continuous or periodic (e.g., every second) basis the orientation of the patient to help determine whether the patient is repositioned frequently enough to reduce the patient's risk of forming a pressure ulcer. In certain embodiments, the wireless sensor 102 minimally processes measured acceleration and/or angular velocity data and wirelessly transmits the minimally-processed data to the patient monitor 106 by way of the wireless communications link 104.

The wireless sensor 102 and the patient monitor 106 can be configured to utilize different wireless technologies to form the wireless communications link 104. In certain scenarios, it may be desirable to transmit data over Bluetooth or ZigBee, for example, when the distance between the wireless sensor 102 and the patient monitor 106 is within range of Bluetooth or ZigBee communication. Transmitting data using Bluetooth or ZigBee is advantageous because these technologies require less power than other wireless technologies. Accordingly, longevity of embodiments of the disclosed wireless sensor 102 using batteries may be increased by using Bluetooth or ZigBee protocols.

In other scenarios, it may be desirable to transmit data using Wi-Fi or cellular telephony, for example, when the distance between the wireless sensor 102 and the patient monitor 106 is out of range of communication for Bluetooth or ZigBee. A wireless sensor 102 may be able to transmit data over a greater distance using Wi-Fi or cellular telephony than other wireless technologies. In still other scenarios, it may be desirable to transmit data using a first wireless technology and then automatically switching to a second wireless technology in order to maximize data transfer and/or energy efficiency.

In some embodiments, the wireless sensor 102 automatically transmits data over Bluetooth or ZigBee when the wireless sensor 102 is within a pre-determined distance from the bedside patient monitor 106. The wireless sensor 102 automatically transmits data over Wi-Fi or cellular telephony when the wireless sensor 102 is beyond a pre-determined distance away from the bedside patient monitor 106. In certain embodiments, the wireless sensor 102 can automatically convert from Bluetooth or ZigBee to Wi-Fi or cellular telephony, and vice versa, depending on the distance between the wireless sensor 102 and the bedside patient monitor 106.

In some embodiments, the wireless sensor 102 automatically transmits data over Bluetooth or ZigBee when the Bluetooth or ZigBee signal strength is sufficiently strong or when there is interference with Wi-Fi or cellular telephony. The wireless sensor 102 automatically transmits data over Wi-Fi or cellular telephony when the Bluetooth or ZigBee signal strength is not sufficiently strong. In certain embodiments, the wireless sensor 102 can automatically convert from Bluetooth or ZigBee to Wi-Fi or cellular telephony, and vice versa, depending on signal strength.

The patient monitor 106 can be operable to receive, store and process the measured acceleration and angular velocity data transmitted by the wireless sensor 102 to determine the patient's orientation. Once determined, the patient monitor 106 can display the patient's current orientation. In some embodiments, the patient monitor 106 displays the patient's current orientation along with the patient's previous orientations over time, thereby providing the user the ability to view a historical record of the patient's orientation. In certain embodiments, e.g., as illustrated in FIGS. 13A-F and 14, the patient orientation is displayed by icons, such stick figures, enabling the clinician to readily understand the patient's present positional state and the patient's positional history. The patient monitor 106 can also be configured to keep track of the length of time the patient remains in a particular orientation. In some embodiments the patient monitor 106 displays the amount of time the patient has been in the current orientation. Additionally, the patient monitor 106 can determine when the patient remains in a particular orientation for a duration greater than that prescribed by a clinician according to a repositioning protocol. Under such conditions, the patent monitor 106 can issue alarms, alerts, and/or notifications to the patient and/or to caregivers indicating that the patient should be repositioned to adhere to the prescribed repositioning protocol to reduce the risk of pressure ulcer formation.

As illustrated in FIG. 1C, the patient monitor 106 communicates over a network 108 with a patient data processing environment 105 that includes a multi-patient monitoring system 110, a hospital/facility system 112, nurses' station systems 113, and clinician devices 114. Examples of network-based clinical processing environments, including multi-patient monitoring systems 110, are disclosed in U.S. Pat. Pub. Nos. 2011/0105854, 2011/0169644, and 2007/0180140, which are incorporated herein by reference in their entirety. In general, the multi-patient monitoring system 110 communicates with a hospital/facility system 112, the nurses' station systems 113, and clinician devices 114. The hospital/facility system 112 can include systems such as electronic medical record (EMR) and/or and admit, discharge, and transfer (ADT) systems. The multi-patient monitoring system 110 may advantageously obtain through push, pull or combination technologies patient information entered at patient admission, such as patient identity information, demographic information, billing information, and the like. The patient monitor 106 can access this information to associate the monitored patient with the hospital/facility systems 112. Communication between the multi-patient monitoring system 110, the hospital/facility system 112, the nurses' station systems 113, the clinician devices 114, and the patient monitor 106 may be accomplished by any technique recognizable to an artisan from the disclosure herein, including wireless, wired, over mobile or other computing networks, or the like.

Figure 1D:
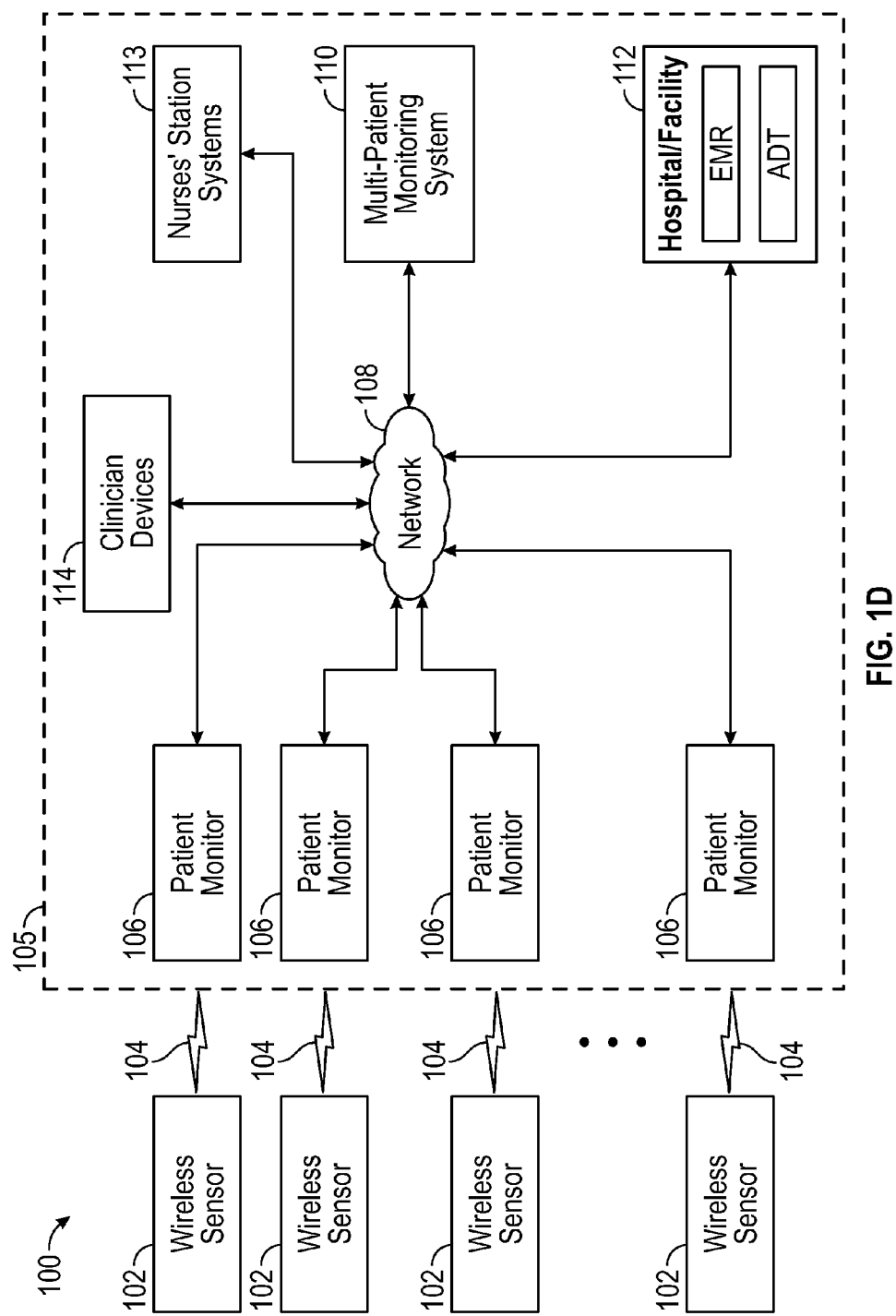
FIG. 1D is a functional block diagram of an embodiment of the disclosed patient monitoring system.

FIG. 1D is a simplified functional block diagram of the disclosed patient monitoring system 100 of FIG. 1C expanded to illustrate use of multiple wireless sensors 102 with multiple patients within a caretaking environment. Advantageously, the patient monitoring system 100 can provide individual patient information on, for example, a patient monitor 106, as well as aggregated patient information on, for example, a nurses' station server or system 114. Thus a caretaker can have an overview of positional information corresponding to a population of patients located, for example, in a hospital floor or unit.

In some circumstances, there may not be the need, desire, or resources available to employ a bedside patient monitor 106 associated with a wireless sensor 102 being worn by a patient. For example, the clinical environment might be staffed such that patient data are collected, analyzed, displayed, and monitored at a central observation station, such as a nurses' station, rather than at the patient's bedside. Moreover, when the information is to be accessed by a clinician at the bedside, portable clinician devices 114, such as, for example, tablets, PDAs or the like, may be used by caregivers to access the required patient-specific information while at the patient's bedside.

Figure 1E:
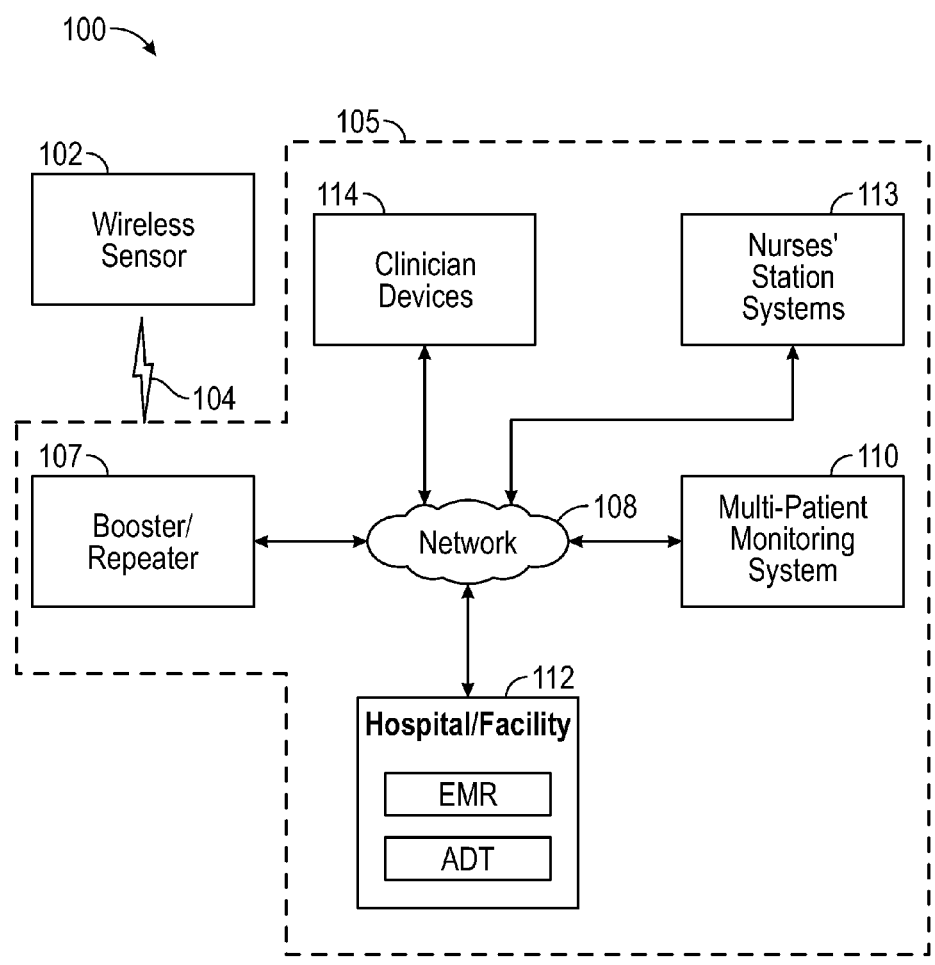
FIG. 1E is a functional block diagram of an embodiment of the disclosed patient monitoring system.
Figure 1F:
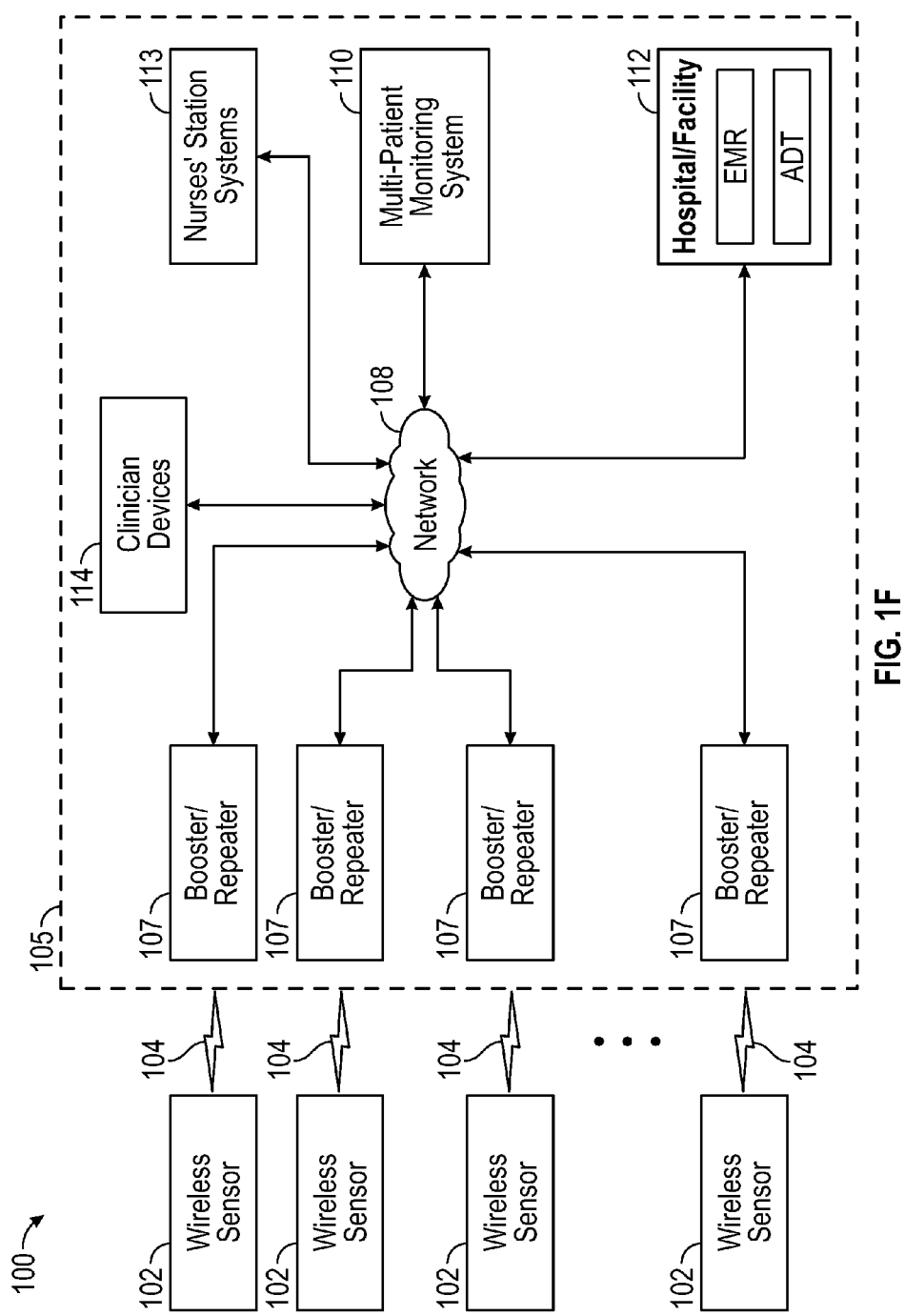
FIG. 1F is a functional block diagram of an embodiment of the disclosed patient monitoring system.

In such situations, as illustrated in FIGS. 1E and 1F, the wireless sensor 102 can communicate to the various systems of the clinical computing environment by way of a signal extender/repeater 107. The extender/repeater 107 is located within range of the wireless sensor 102 (e.g., near the patient's bed 118) and configured to relay data, via the network 108, between the wireless sensor 102 and one or more computing systems capable of processing, storing, displaying, and/or transmitting the data collected by the wireless sensor 102. Advantageously, a relatively low cost extender/repeater 107 can be used to receive signals transmitted from one or more wireless sensors 102 over the wireless communications link(s) 104 using a shorter-range, lower-power-consuming transmission mode, such as for example, Bluetooth or ZigBee. The extender/repeater 107 can then retransmit the received signals to one or more computing systems in the patient data processing environment 105 over the network 108. In accordance with some embodiments, the extender/repeater 107 is a Bluetooth-to-Ethernet gateway that retransmits signals received from the wireless sensor 102 to computing nodes, such as, for example, the multi-patient monitoring system 110, over the network 108. In some embodiments, the extender/repeater 107 is a Bluetooth-to-WiFi bridge that provides access to the network 108 for the wireless sensor 102. Of course, a skilled artisan will recognize that there are numerous ways to implement the extender/repeater 107.

Figure 2A:
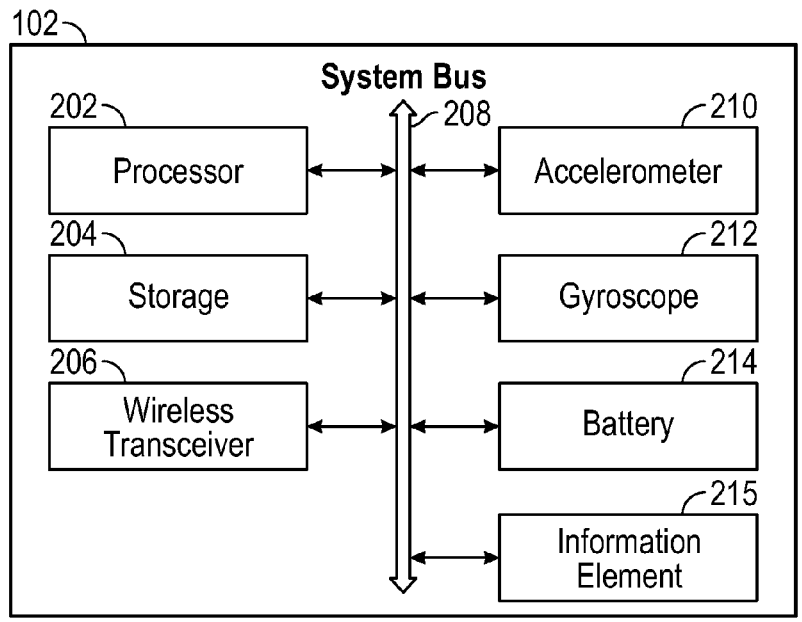
FIG. 2A is a functional block diagram of an embodiment of the disclosed wireless sensor.

FIG. 2A illustrates a simplified hardware block diagram of an embodiment of the disclosed wireless sensor 102. As shown in FIG. 2A, the wireless sensor 102 can include a processor 202, a data storage device 204, a wireless transceiver 206, a system bus 208, an accelerometer 210, a gyroscope 212, a battery 214, and an information element 215. The processor 202 can be configured, among other things, to process data, execute instructions to perform one or more functions, such as the methods disclosed herein, and control the operation of the wireless sensor 102. The data storage device 204 can include one or more memory devices that store data, including without limitation, random access memory (RAM) and read-only memory (ROM). The wireless transceiver 206 can be configured to use any of a variety of wireless technologies, such as Wi-Fi (802.11x), Bluetooth, ZigBee, cellular telephony, infrared, RFID, satellite transmission, proprietary protocols, combinations of the same, and the like. The components of the wireless sensor 102 can be coupled together by way of a system bus 208, which may represent one or more buses. The battery 214 provides power for the hardware components of the wireless sensor 102 described herein. As illustrated in FIG. 2A, the battery 214 communicates with other components over system bus 208. One skilled in the art will understand that the battery 214 can communicate with one or more of the hardware functional components depicted in FIG. 2A by one or more separate electrical connections. The information element 215 can be a memory storage element that stores, in non-volatile memory, information used to help maintain a standard of quality associated with the wireless sensor 102. Illustratively, the information element 215 can store information regarding whether the sensor 102 has been previously activated and whether the sensor 102 has been previously operational for a prolonged period of time, such as, for example, four hours. The information stored in the information element 215 can be used to help detect improper re-use of the wireless sensor 102.

In some embodiments, the accelerometer 210 is a three-dimensional (3D) accelerometer. The term 3D accelerometer as used herein includes its broad meaning known to a skilled artisan. The accelerometer 210 provides outputs responsive to acceleration of the wireless sensor 102 in three orthogonal axes, sometimes denoted as the "X," "Y," and "Z" axes. An accelerometer 210 may measure acceleration that it experiences relative to Earth's gravity. An accelerometer 210 may provide acceleration information along three axes, and it and may provide acceleration information which is the equivalent of inertial acceleration minus local gravitational acceleration. Accelerometers 210 are well known to those skilled in the art. The accelerometer 210 may be a micro-electromechanical system (MEMS), and it may include piezoresistors, among other forms of implementation. The accelerometer 210 may be a high-impedance charge output or a low-impedance charge output accelerometer 210. In some embodiments, the accelerometer 210 may be a tri-axis accelerometer, and the output of the accelerometer 210 may include three signals, each of which represents measured acceleration in particular axis. The output of the accelerometer 210 may be 8-bit, 12-bit, or any other appropriate-sized output signal. The outputs of the accelerometer may be in analog or digital form. The accelerometer 210 may be used to determine the position, orientation, and/or motion of the patient to which the wireless sensor 102 is attached.

In some embodiments, the gyroscope 212 is a three-axis digital gyroscope with angle resolution of two degrees and with a sensor drift adjustment capability of one degree. The term three-axis gyroscope as used herein includes its broad meaning known to a skilled artisan. The gyroscope 212 provides outputs responsive to sensed angular velocity of the wireless sensor 102 (as affixed to the patient) in three orthogonal axes corresponding to measurements of pitch, yaw, and roll. A skilled artisan will appreciate that numerous other gyroscopes 212 can be used in the wireless sensor 102 without departing from the scope of the disclosure herein. In certain embodiments, the accelerometer 210 and gyroscope 212 can be integrated into a single hardware component which may be referred to as an inertial measurement unit (IMU). In some embodiments, the IMU can also include an embedded processor that handles, among other things, signal sampling, buffering, sensor calibration, and sensor fusion processing of the sensed inertial data. In other embodiments, the processor 202 can perform these functions. And in still other embodiments, the sensed inertial data are minimally processed by the components of the wireless sensor 102 and transmitted to an external system, such as the patient monitor 106, for further processing, thereby minimizing the complexity, power consumption, and cost of the wireless sensor 102, which may be a single-use, disposable product.

Figure 2B:
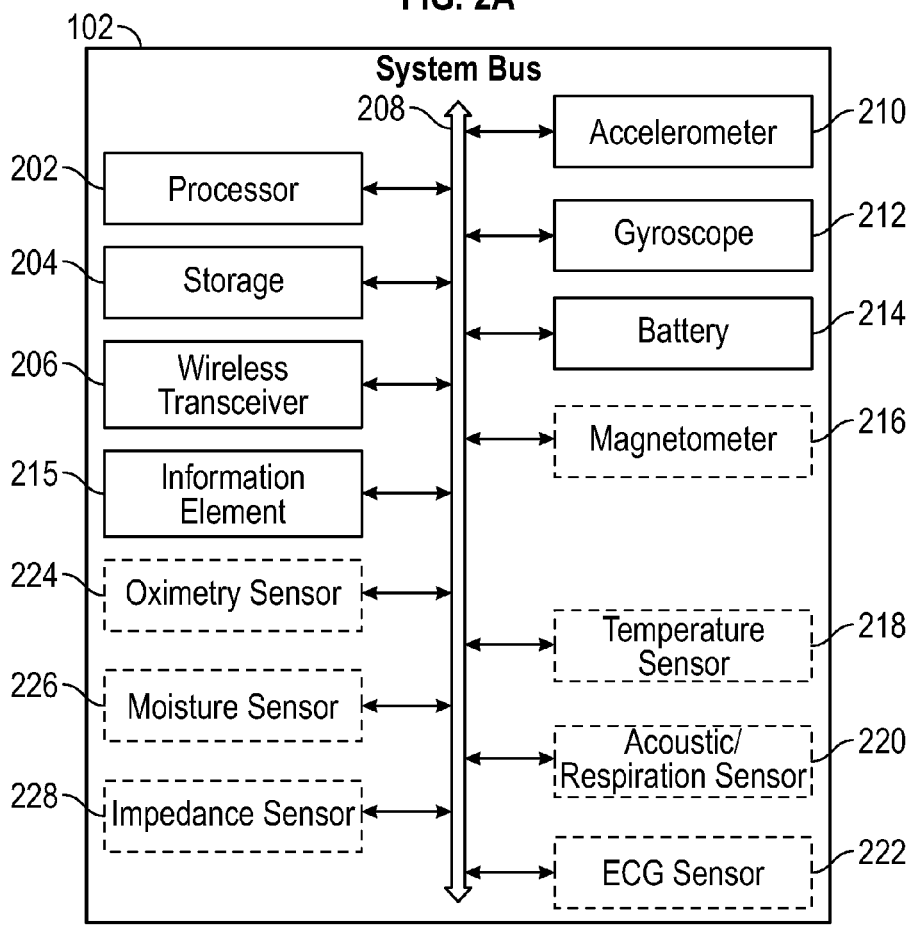
FIG. 2B is a functional block diagram of an embodiment of the disclosed wireless sensor including optional sensing components.

FIG. 2B is a simplified hardware functional block diagram of an embodiment of the disclosed wireless sensor 102 that includes the following optional (as reflected by dotted lines) sensing components: a magnetometer 216 which may also be referred to as a compass, a temperature sensor 218, an acoustic respiration sensor 220, an electrocardiogram (ECG) sensor 222, one or more oximetry sensors 224, a moisture sensor 226, and an impedance sensor 228. In some embodiments, the magnetometer 216 is a three-dimensional magnetometer that provides information indicative of magnetic fields, including the Earth's magnetic field. While depicted in FIG. 2B as separate functional elements, a skilled artisan will understand that the accelerometer 210, gyroscope 212, and magnetometer 214 can be integrated into a single hardware component such as an inertial measurement unit.

According to an embodiment, a system and method are described herein to calculate three-dimensional position and orientation of an object derived from inputs from three sensors attached to the object: an accelerometer 210 configured to measure linear acceleration along three axes; a gyroscope 212 configured to measure angular velocity around three axes; and a magnetometer 214 configured to measure the strength of a magnetic field (such as the Earth's magnetic field) along three axes. In an embodiment, the three sensors 210, 212, and 214 are attached to the wireless sensor 102 which is affixed to the patient. According to an embodiment, the sensors 210, 212, and 214 are sampled at a rate between approximately 10 Hz and approximately 100 Hz. One skilled in the art will appreciate that the sensors 210, 212, and 214 can be sampled at different rates without deviating from the scope of the present disclosure. The sampled data from the three sensors 210, 212, and 214, which provide nine sensor inputs, are processed to describe the patient's position and orientation in three-dimensional space. In an embodiment, the patient's position and orientation are described in terms of Euler angles as a set of rotations around a set of X-Y-Z axes of the patient.

Also illustrated in FIG. 2B is a temperature sensor 218 which may be used to measure the patient's body core temperature which is a vital sign used by clinicians to monitor and manage patients' conditions. The temperature sensor 218 can include a thermocouple, a temperature-measuring device having two dissimilar conductors or semiconductors that contact each other at one or more spots. A temperature differential is experienced by the different conductors. The thermocouple produces a voltage when the contact spot differs from a reference temperature. Advantageously, thermocouples are self-powered and therefore do not require an external power source for operation. In an embodiment, the temperature sensor 218 includes a thermistor. A thermistor is a type of resistor whose resistance value varies depending on its temperature. Thermistors typically offer a high degree of precision within a limited temperature range.

The acoustic respiration sensor 220 can be used to sense vibrational motion from the patient's body (e.g., the patient's chest) that are indicative of various physiologic parameters and/or conditions, including without limitation, heart rate, respiration rate, snoring, coughing, choking, wheezing, and respiratory obstruction (e.g., apneic events). The ECG sensor 222 can be used to measure the patient's cardiac activity. According to an embodiment, the ECG sensor 222 includes two electrodes and a single lead. The oximetry sensor(s) 224 can be used to monitor the patient's pulse oximetry, a widely accepted noninvasive procedure for measuring the oxygen saturation level of arterial blood, an indicator of a person's oxygen supply. A typical pulse oximetry system utilizes an optical sensor clipped onto a portion of the patient's body (such as, for example, a fingertip, an ear lobe, a nostril, and the like) to measure the relative volume of oxygenated hemoglobin in pulsatile arterial blood flowing within the portion of the body being sensed. Oxygen saturation (SpO2), pulse rate, a plethysmograph waveform, perfusion index (PI), pleth variability index (PVI), methemoglobin (MetHb), carboxyhemoglobin (CoHb), total hemoglobin (tHb), glucose, and/or otherwise can be measured and monitored using the oximetry sensor(s) 224. The moisture sensor 226 can be used to determine a moisture content of the patient's skin which is a relevant clinical factor in assessing the patient's risk of forming a pressure ulcer. The impedance sensor 228 can be used to track fluid levels of the patient. For example, the impedance sensor 228 can monitor and detect edema, heart failure progression, and sepsis in the patient.

Figure 3A:
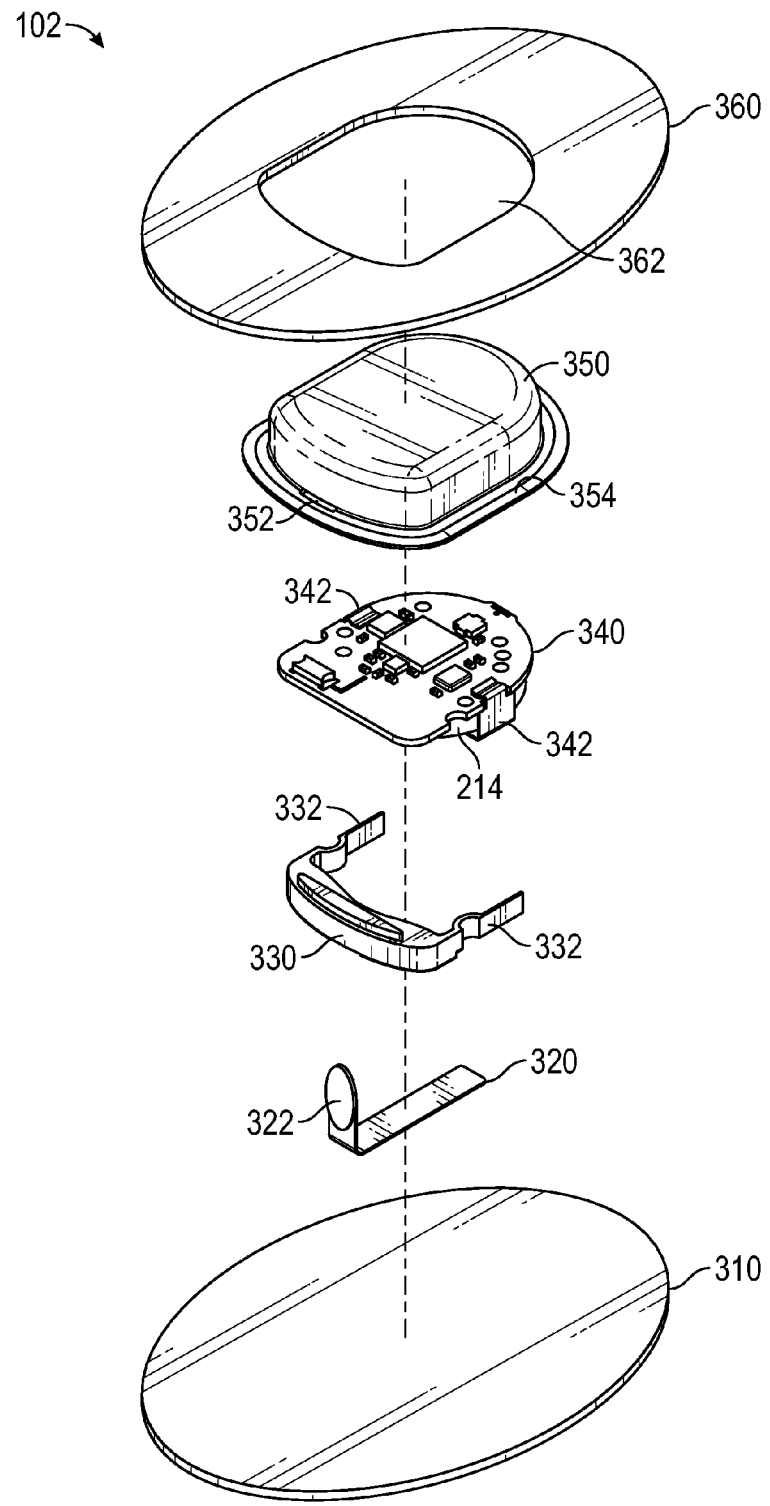
FIG. 3A is a schematic exploded perspective view of an embodiment of the disclosed wireless sensor.

FIG. 3A is a schematic exploded perspective view of an embodiment of the disclosed wireless sensor 102 including a bottom base 310, a removable battery isolator 320, a mounting frame 330, a circuit board 340, a housing 350, and a top base 360. The bottom base 310 is a substrate having a top surface on which various components of the wireless sensor 102 are positioned, and a bottom surface that is used to affix the wireless sensor 102 to the patient's body. The bottom base 310 and top base 360 can be made of medical-grade foam material such as white polyethylene, polyurethane, or reticulated polyurethane foams, to name a few. As illustrated in the embodiment illustrated in FIG. 3A, the bottom base 310 and the top base 360 are each in a substantially oval shape, with a thickness of approximately 1 mm. The top base 360 includes a cut-out 362 through which the housing 350 fits during assembly. Of course, a skilled artisan will understand that there are numerous sizes and shapes suitable for the top and bottom bases 310 and 360 that can be employed without departing from the scope of the present disclosure. The bottom surface of the bottom base 310 is coated with a high tack, medical-grade adhesive, which when applied to the patient's skin, is suitable for long-term monitoring, such as, for example two days or longer. Portions of the top surface of the bottom base 310 are also coated with a medical-grade adhesive, as the bottom base 310 and the top base 360 are adhered together during assembly of the wireless sensor 102.

The removable battery isolator 320 is a flexible strip made of an electrically insulating material that serves to block electrical communication between the battery 214 and an electrical contact (not shown) on the circuit board 340. The battery isolator 320 is used to preserve battery power until the wireless sensor 102 is ready for use. The battery isolator 320 blocks electrical connection between the battery 214 and the circuit board 340 until the battery isolator 320 is removed from the wireless sensor 102. The battery isolator 320 can be made of any material that possesses adequate flexibility to be slidably removed from its initial position and adequate dielectric properties so as to electrically isolate the battery from the circuit board 340. For example, the battery isolator can be made of plastic, polymer film, paper, foam, combinations of such materials, or the like. The battery isolator 320 includes a pull tab 322 that extends through a slot 352 of the housing 350 when the wireless sensor 102 is assembled. The pull tab 322 can be textured to provide a frictional surface to aid in gripping and sliding the pull tab 322 out of its original assembled position. Once the battery isolator 320 is removed the battery 214 makes an electrical connection with the battery contact to energize the electronic components of the wireless sensor 102.

The mounting frame 330 is a structural support element that helps secure the battery 214 to the circuit board 340. The mounting frame 340 has wings 342 that, when assembled are slid between battery contacts 342 and the battery 214. Additionally, the mounting frame 330 serves to provide rigid structure between the circuit board 340 and the bottom base 310. According to some embodiments that include an acoustic respiratory sensor, the rigid structure transmits vibrational motion (vibrations) emanating from the patient (such as, for example, vibrational motions related to respiration, heartbeat, snoring, coughing, choking, wheezing, respiratory obstruction, and the like) to the accelerometer 210 positioned on the circuit board 340.

The circuit board 340, which may also be referred to herein as a substrate layer 340 and a circuit layer 340, mechanically supports and electrically connects electrical components to perform many of the functions of the wireless sensor 102. The circuit board 340 includes conduction tracks and connection pads. Such electrical components can include without limitation, the processor 202, the storage device 204, the wireless transceiver 206, the accelerometer 210, the gyroscope 212, the magnetometer 214, the temperature sensor 218, the acoustic respiration sensor 220, the ECG sensor 222, the oximetry sensor 224, the moisture sensor 226, and the impedance sensor 228. In an embodiment, the circuit board 340 is double sided having electronic components mounted on a top side and a battery contact (not shown) on a bottom side. Of course a skilled artisan will recognize other possibilities for mounting and interconnecting the electrical and electronic components of the wireless sensor 102.

As illustrated in FIG. 3A, a battery holder 342 is attached to two sides of the top portion circuit board 340 and extends (forming a support structure) under the bottom side of the circuit board 340 to hold the battery 214 in position relative to the circuit board 340. The battery holder 342 is made of electrically conductive material. In some embodiments, the battery 214 is a coin cell battery having a cathode on the top side and an anode on the bottom side. Electrical connection between the anode of the battery 214 and the circuit board 340 is made by way of the battery holder which is in electrical contact with the anode of the battery 214 and the circuit board 340. The cathode of the battery 214 is positioned to touch a battery contact (not shown) on the bottom side of the circuit board 340. In some embodiments, the battery contact includes a spring arm that applies force on the battery contact to ensure that contact is made between the anode of the battery 214 and the battery contact. During assembly and prior to use, the battery isolator 320 is inserted between the anode of the battery 214 and the battery connector to block electrical contact.

The housing 350 is a structural component that serves to contain and protect the components of the wireless sensor 102. The housing 350 can be made of any material that is capable of adequately protecting the electronic components of the wireless sensor 102. Examples of such materials include without limitation thermoplastics and thermosetting polymers. The housing 350 includes a slot 352 through which the battery isolator 320 is inserted during assembly. The housing 350 also includes a rim 354 that extends around the outer surface of the housing 350. The rim 354 is used to secure the housing 350 in position relative to the bottom base 310 and the top base 360 when the wireless sensor 102 is assembled.

Assembly of the wireless sensor 102 is as follows: The circuit board 340 and battery holder 342 holding the battery 214 are placed into the housing 350. The wings 332 of the mounting frame 330 are inserted in between the battery 214 and the battery holder 342, so as to align the mounting frame 330 with the circuit board 340. The battery isolator 320 is then positioned between the battery contact and the battery 214. The pull tab 322 of the battery isolator 320 is then fed through the slot 352 in the housing 350. The top base 360 is then positioned over the housing 350, which now houses the assembled circuit board 340, battery holder 342, battery 214, mounting frame 330, and battery isolator 320, using the cut-out 362 for alignment. The rim 354 of the housing 350 adheres to the bottom surface of the top base 360, which is coated with high tack, medical-grade adhesive. The partial assembly, which now includes the top base 360, the housing 350, the circuit board 340, the battery holder 342, the battery 214, the mounting frame 330, and the battery isolator 320, is positioned centrally onto the top surface of the bottom base 310, aligning the edges of the base top 360 with the edges of the base bottom 310. In some embodiments, a coupon (or die cutting tool) is used to cut away excess portions of the now combined top and bottom bases 360 and 310 to form a final shape of the wireless sensor 102. The bottom surface of the bottom base 310 is then coated with a high tack, medical-grade adhesive, and a release liner (not shown) is placed on the bottom surface of the bottom base 3310 to protect the adhesive until it is time for use.

Figure 3B:
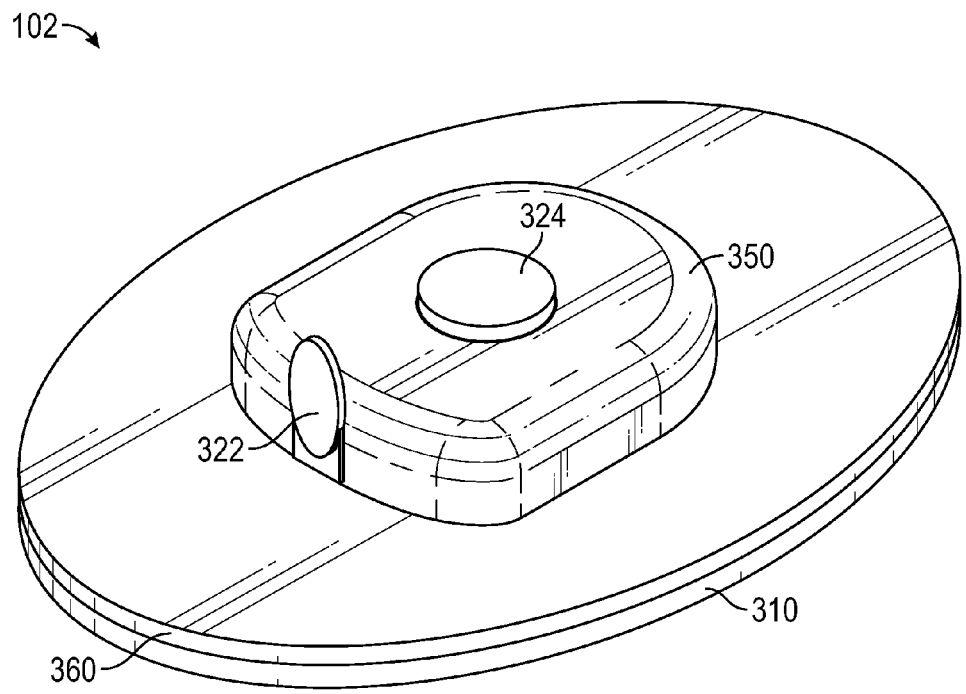
FIG. 3B is a schematic assembled perspective view of the embodiment of the disclosed wireless sensor of FIG. 3A.
Figure 3C:
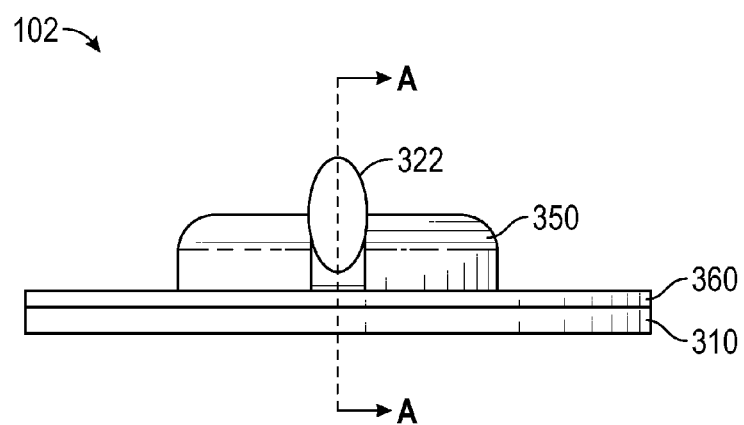
FIG. 3C is a schematic side view of the embodiment of the disclosed wireless sensor of FIGS. 3A and 3B.

A schematic perspective view of the assembled wireless sensor 102 is illustrated in FIG. 3B. Also illustrated in FIG. 3B is a button/switch 324 located on a top portion of the housing 350. The button/switch 324 can be used to change modes of the wireless sensor 102. For example, in some embodiments, pressing and holding the button/switch 324 can cause the wireless sensor 102 to switch into a pairing mode of operation. The pairing mode is used to associate the wireless sensor 102 with a patient monitor 106 or with an extender/repeater 107. FIG. 3C provides a schematic side view of an embodiment of the assembled wireless sensor 102 with cross-section line A-A identified.

Figure 4A:
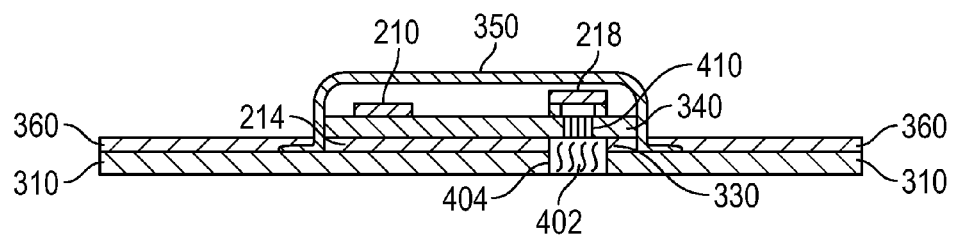
FIG. 4A is a schematic cross-sectional view of an embodiment of the disclosed wireless sensor which includes a temperature sensor.
Figure 4B:
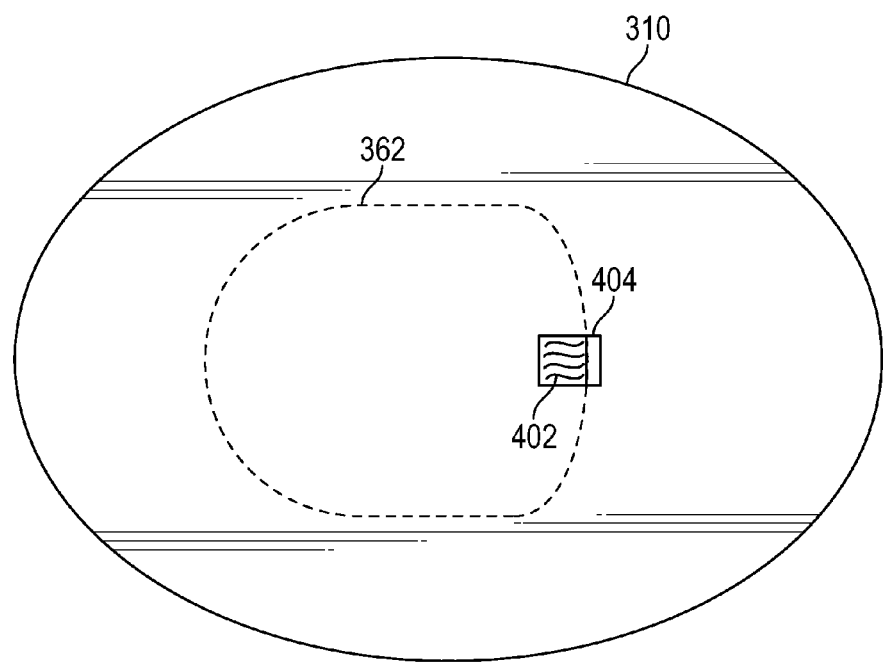
FIG. 4B is a schematic bottom view of the embodiment of the disclosed wireless sensor of FIG. 4A.

Referring now to FIGS. 4A and 4B, an embodiment of the wireless sensor 102 is disclosed which includes a temperature sensor 218. FIG. 4A is a schematic cross-sectional view, sectioned along line A-A of FIG. 3C, illustrating an assembled embodiment of the disclosed wireless sensor 102 which includes the temperature sensor 218. For easier visibility, the battery isolator 320 and the battery holder 342 are not illustrated. FIG. 4B is a schematic bottom view of the embodiment of the disclosed wireless sensor of FIG. 4A. The bottom surface of the bottom base 310 is illustrated. Also illustrated in phantom (i.e., dotted lines) is the outline of cut-out 362 which also indicates the position of the housing 350 in relation to the bottom surface of the bottom base 310.

As explained above with respect to the assembly of the wireless sensor 102, the top surface of the bottom base 310 is in contact with and adhered to the bottom surface of the top base 360. The rim 354 of the housing 350 is sandwiched between the two bases 310 and 360 to secure the housing 350. The housing 350 also protrudes through the cut-out 362 of the top base 360. Within the housing, the battery 214 and the mounting frame 330 are adjacent the top surface of the bottom base 310.

As illustrated in FIG. 4A, the temperature sensor 218 is mounted on the circuit board 340. To perform its temperature sensing function, the temperature sensor 218 is in thermal contact with the patient's skin. To achieve this, structure to transmit thermal energy from the patient's body to the temperature sensor 218 is provided. In particular, inputs to the temperature sensor 218 are thermally connected to multiple through-hole vias 410 located in the circuit board 340. A through-hole via is a small vertical opening or pathway in the circuit board 340 through which thermally and/or electrically conductive material can be placed, thereby permitting transmission of thermal and/or electrical energy from one side of the circuit board 340 to the other side. Under the through-hole vias 410 is an aperture or opening 404 which extends through the mounting frame 330 (to form a mounting frame aperture) and through the bottom base 310 of the wireless sensor 102. The aperture 404 provides access from the temperature sensor 218 to the patient's skin when the wireless sensor 102 is worn by the patient. The aperture 404 and the through-hole vias 410 are filled with thermally conductive material 402. Thermally conductive materials are well known in the art and can include, by way of non-limiting example, thermally conductive elastomers, polymers, and resins, to name a few. Illustratively, in operation, the wireless sensor 102 is affixed to the patient's skin. The thermally conductive material 402, exposed to the patient's skin, transmits thermal energy from the patient's body through the aperture 404 and the through-hole vias 410 to arrive at the inputs to the temperature sensor 218.

Advantageously, the disclosed wireless sensor 102 can measure the patient's body core temperature (an established and useful vital sign) with the temperature sensor 218 using a technique by which deep tissue temperature can be measured from the skin surface. In the human body, there is a natural heat flux between the body core and the skin surface because the body core temperature is typically at a higher temperature than that of the skin surface. Thus heat flows from the body core to the skin. By insulating the skin surface at and around the point at which the skin temperature is measured—thereby blocking heat from escaping—the temperature gradient between the body core and the skin surface will decrease. The skin temperature, under the insulated area will rise until it reaches equilibrium with the warmest region (i.e., the body core) under the insulation, thereby approaching the body core temperature. When equilibrium is reached, the skin temperature is equal to the core body temperature. Advantageously, the bottom base 310 and top base 360 of the wireless sensor 102, which are in contact with the patient's skin around the temperature sensor 218, possess thermal insulation properties. Illustratively, by way of non-limiting example, the bottom base 310 and top base 360 can be made thermally insulating materials including polyurethane foam, polystyrene foam, neoprene foam, neoprene rubber, polyester (Mylar), polytetrafluoroethylene (PTFE), silicone foam, silicone rubber, or the like. Accordingly, the temperature sensor 218 can measure the patient's body core temperature.

Figure 4C:
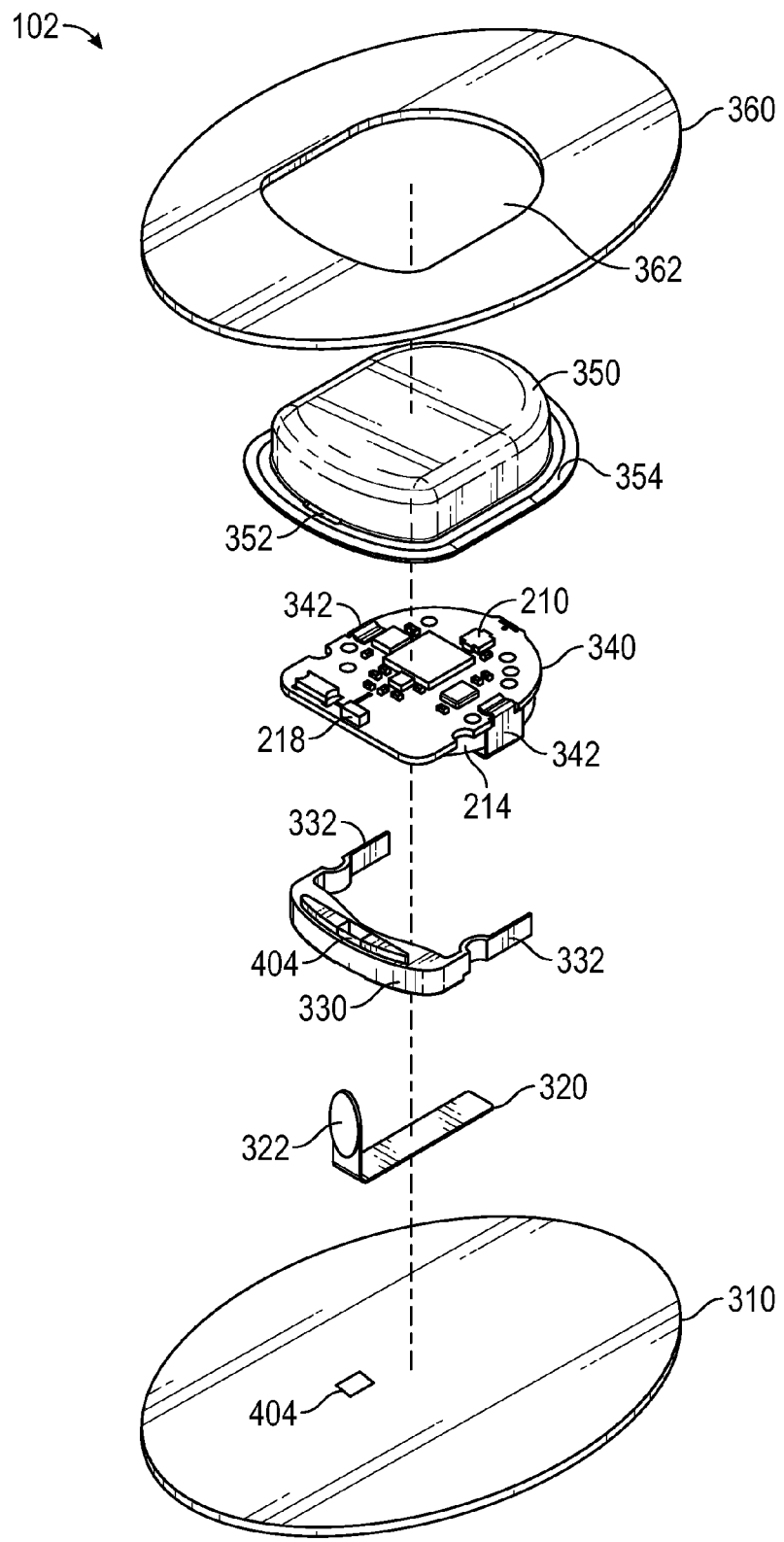
FIG. 4C is a schematic exploded perspective view of the embodiment of the disclosed wireless sensor of FIGS. 4A-B.

FIG. 4C is a schematic exploded perspective view of the embodiment of the disclosed wireless sensor of FIGS. 4A and 4B. As shown, the temperature sensor 218 is mounted on the top surface of the circuit board 340. The aperture 404 extends through the mounting frame 330 and the bottom base 310 and is aligned vertically with the through-hole vias 410 (not shown in FIG. 4C) and the temperature sensor 218. The aperture 404 and the through-hole vias 410 are filled with thermally conductive material 402. Thus the disclosed structure provides thermal connectivity between the patient's skin and the temperature sensor 218.

Figure 5A:
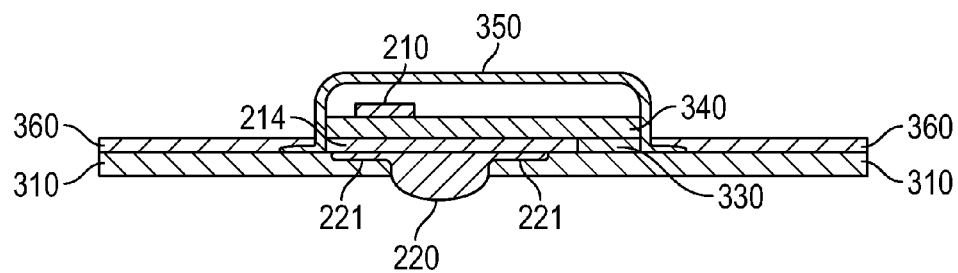
FIG. 5A is a schematic cross-sectional view of an embodiment of the disclosed wireless sensor which includes an acoustic respiration sensor.
Figure 5B:
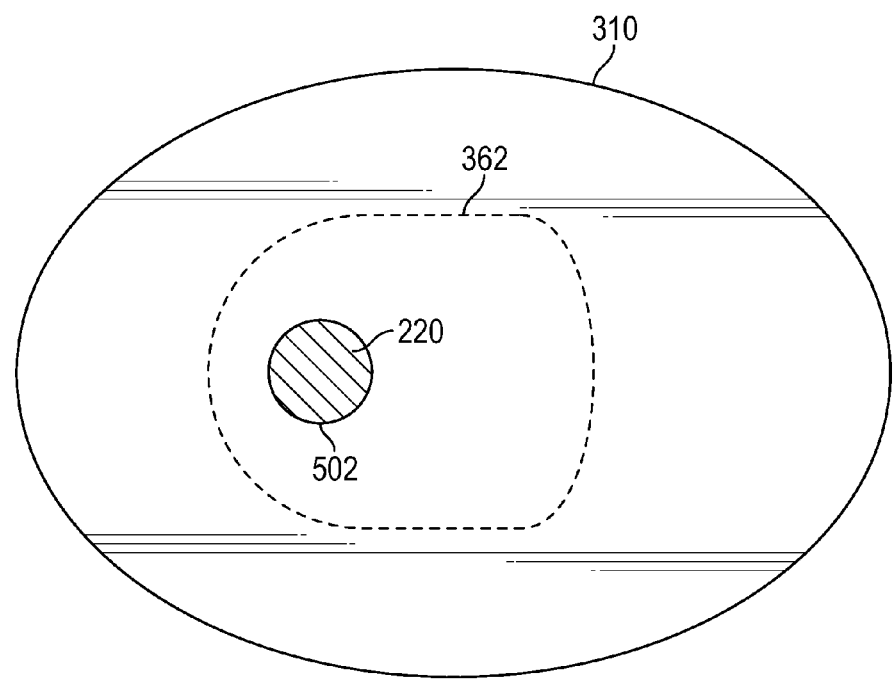
FIG. 5B is a schematic bottom view of the embodiment of the disclosed wireless sensor of FIG. 5A.

Referring now to FIGS. 5A and 5B, an embodiment of the wireless sensor 102 is disclosed which includes an acoustic respiration sensor 220. FIG. 5A is a schematic cross-sectional view, sectioned along line A-A of FIG. 3C, illustrating an assembled embodiment of the disclosed wireless sensor 102 which includes the acoustic respiration sensor 220. For easier visibility, the battery isolator 320 and the battery holder 342 are not illustrated. FIG. 5B is a schematic bottom view of the embodiment of the disclosed wireless sensor of FIG. 5A. The bottom surface of the bottom base 310 is illustrated. Also illustrated in phantom (i.e., dotted lines) is the outline of cut-out 362 which indicates the position of the housing 350 in relation to the bottom surface of the bottom base 310.

As illustrated in FIG. 5A, the acoustic respiration sensor 220 is mounted underneath the battery 214. Operationally, the acoustic respiration sensor 220 detects vibratory motion emanating from the patient's body (e.g., the patient's chest) and mechanically transmits the detected vibratory motion to the accelerometer 210. The accelerometer 210 senses the mechanically transmitted vibratory motion. The signal collected by accelerometer 210 can be processed to extract the vibratory motion from other sensed acceleration signals. Examples of such vibratory motion can include, without limitation, heart beats, respiration activity, coughing, wheezing, snoring, choking, and respiratory obstruction (e.g., apneic events). To mechanically transmit the sensed vibratory motion effectively, the acoustic respiration sensor 220 is in rigid structural contact with the accelerometer 210. To achieve this, the acoustic respiration sensor 220 is mounted to the bottom side of the battery 214. In particular, the acoustic respiration sensor 220 includes a rim 221 that is sandwiched between the bottom surface of the battery 214 and the bottom base 310. Accordingly, the rim 221 serves to rigidly secure the acoustic respiration sensor 220 to the bottom surface of the battery 214.

As illustrated in FIG. 5A, the acoustic respiration sensor 220 protrudes through an aperture or opening 502 in the bottom base 310, beyond the plane created by the bottom base 310. This is to ensure that the acoustic respiration sensor 220 is in direct contact with the patient's body (e.g., chest) so as to sense the vibrational motion emanating from the patient. Within the acoustic respiration sensor 220 is a flexible wire or other such structure under slight tension such that when the wire is exposed to vibratory motion, it will vibrate in a manner that is proportional to the sensed vibratory motion with respect to both frequency and magnitude of the sensed vibratory motion. The acoustic respiration sensor 220 is configured to transmit the sensed vibratory motion through rigid structures of the wireless sensor 102 such that the transmitted vibratory motion is sensed by the accelerometer 210. The rigid structure includes the battery 214 and the circuit board 340.

Figure 5C:
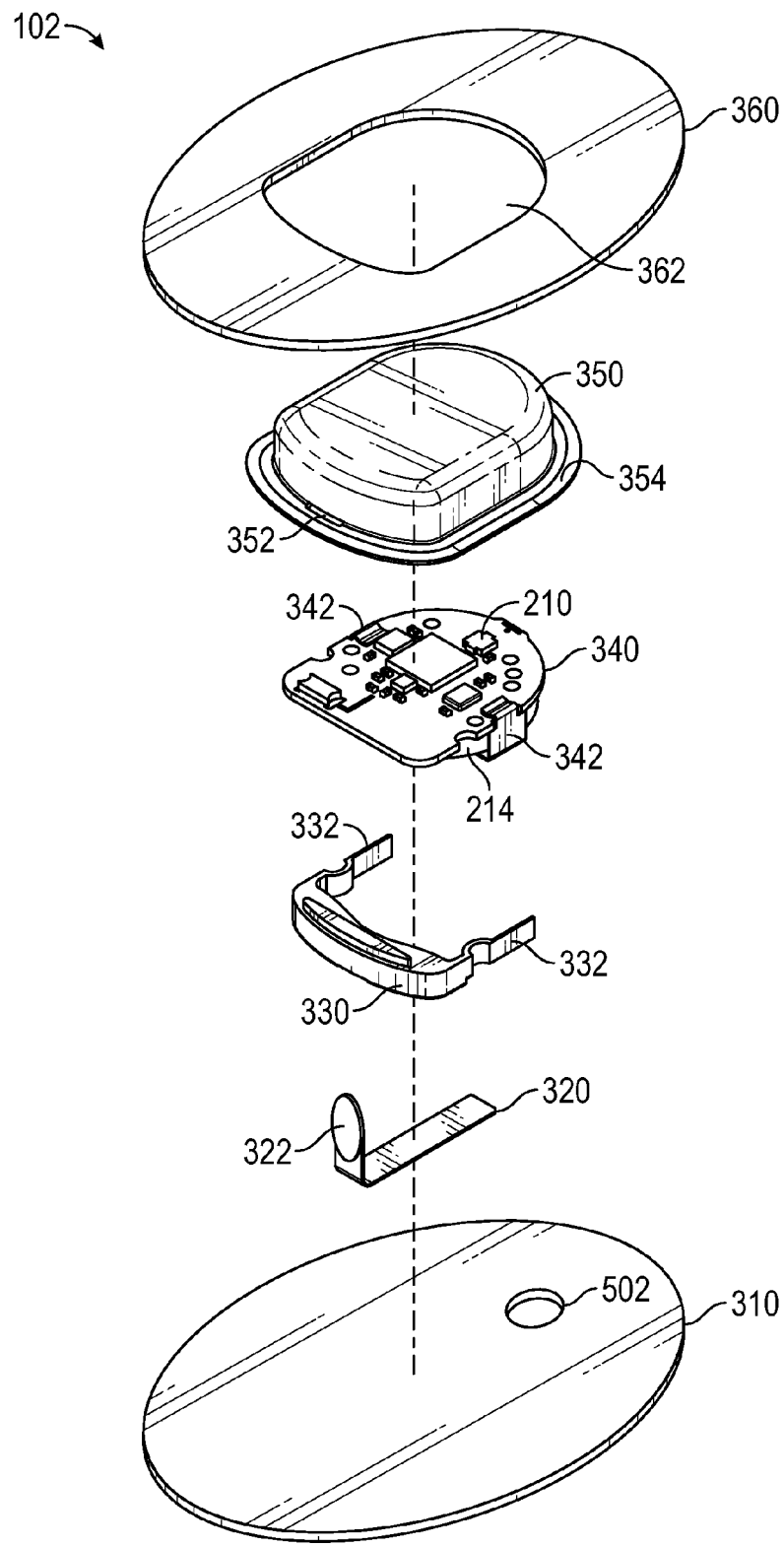
FIG. 5C is a schematic exploded perspective view of the embodiment of the disclosed wireless sensor of FIGS. 5A-B.

FIG. 5C is a schematic exploded perspective view of the embodiment of the disclosed wireless sensor of FIGS. 5A-B. As shown, the accelerometer 210 is mounted on the top surface of the circuit board 340 over the battery 214 which is secured underneath the circuit board 340. The acoustic respiration sensor 220 (not shown in FIG. 5C) fits between the battery 214 and the bottom base 310. The aperture 502 extends through the bottom base 310 and is aligned vertically with battery 214 such that the acoustic respiration sensor 220 is secured to rigid structure of the wireless sensor 102. Thus the disclosed structure provides the ability for the acoustic respiration sensor 220 to mechanically transmit vibratory motion from the patient's chest to the accelerometer 210.

Figure 6A:
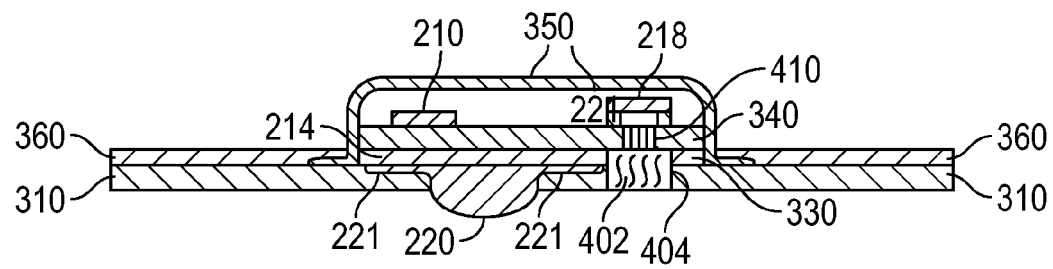
FIG. 6A is a schematic cross-sectional view of an embodiment of the disclosed wireless sensor which includes a temperature sensor and an acoustic respiration sensor.
Figure 6B:
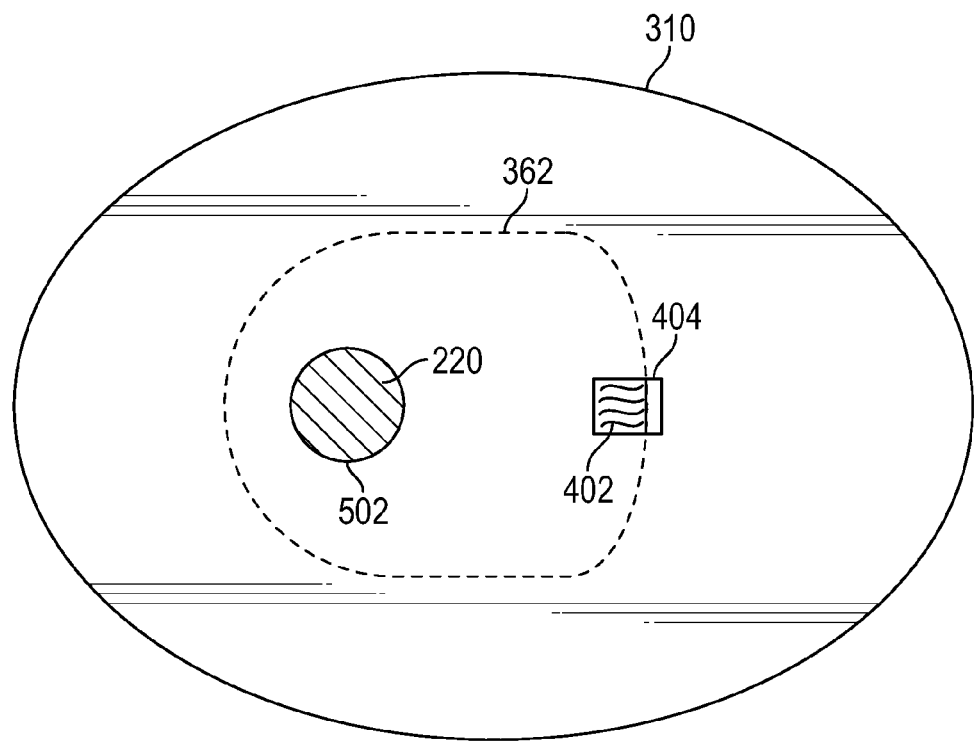
FIG. 6B is a schematic bottom view of the embodiment of the disclosed wireless sensor of FIG. 6A.
Figure 6C:
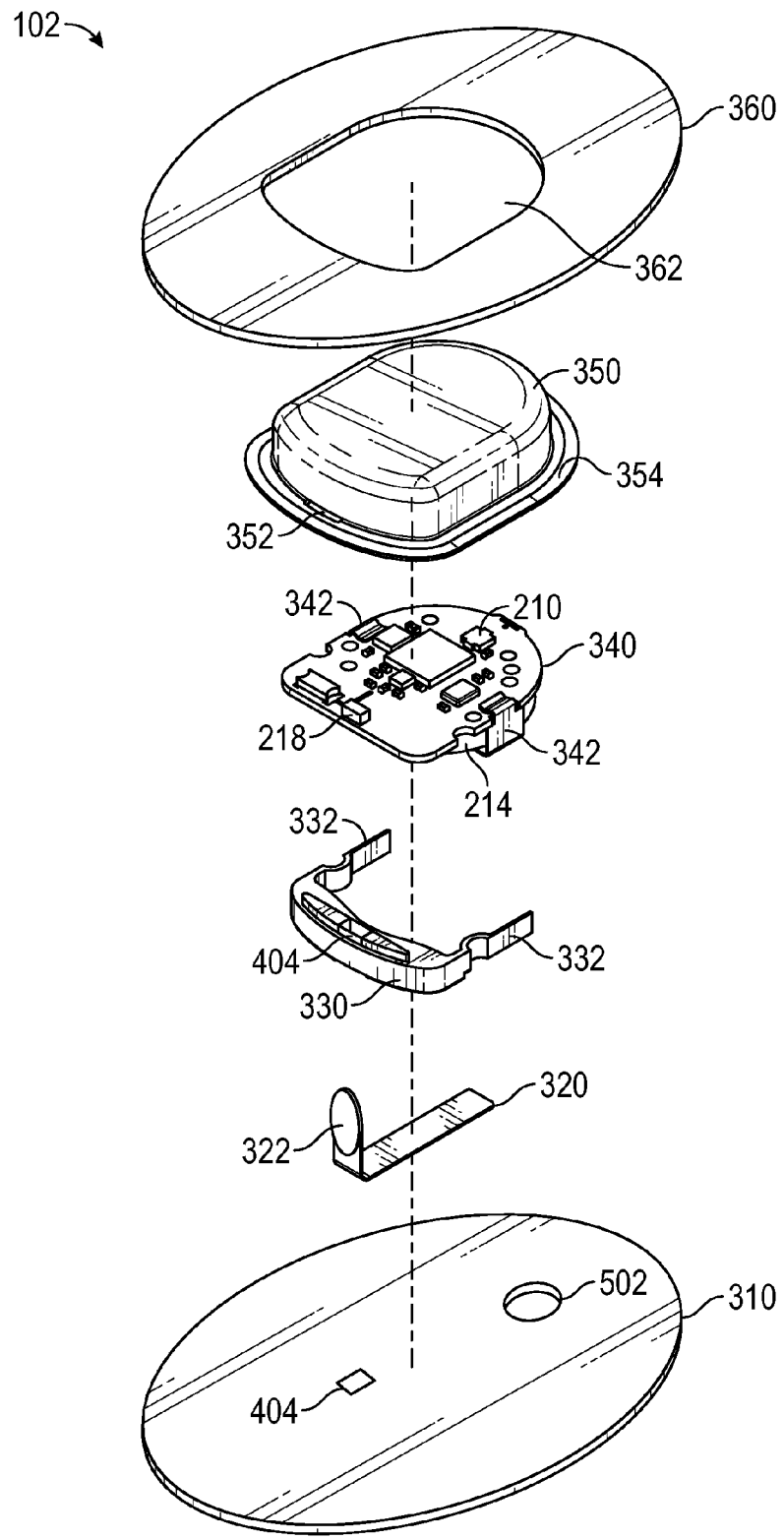
FIG. 6C is a schematic exploded perspective view of the embodiment of the disclosed wireless sensor of FIGS. 6A-B.

FIGS. 6A-C illustrate an embodiment of the disclosed wireless sensor 102 which includes a temperature sensor 218 and an acoustic respiration sensor 220. FIG. 6A is a schematic cross-sectional view, sectioned along line A-A of FIG. 3C, illustrating an assembled embodiment of the disclosed wireless sensor 102 which includes the temperature sensor 218 and acoustic respiration sensor 220. For easier visibility, the battery isolator 320 and the battery holder 342 are not illustrated. FIG. 6B is a schematic bottom view of the embodiment of the disclosed wireless sensor of FIG. 6A. FIG. 6C is a schematic exploded perspective view of the embodiment of the disclosed wireless sensor 102 of FIGS. 6A and 6B.

Structurally, the embodiment depicted in FIGS. 6A-C is a combination of the embodiments depicted in FIGS. 4A-C and 5A-C. As illustrated in FIGS. 6A-B, the temperature sensor 218 is mounted on the circuit board 340. As previously described, inputs to the temperature sensor 218 are thermally coupled to multiple through-hole vias 410 located in the circuit board 340. Under the through-hole vias 410 is an aperture 404 which extends through the mounting frame 330 and through the bottom base 310 of the wireless sensor 102. The aperture 404 provides access from the temperature sensor 218 to the patient's skin when the wireless sensor 102 is worn by the patient. The aperture 404 and the through-hole vias 410 are filled with thermally conductive material 402. In operation, the wireless sensor 102 is affixed to the patient's skin. The thermally conductive material 402, exposed to the patient's skin, transmits thermal energy from the patient's body through the aperture 404 and the through-hole vias 410 to arrive at the inputs to the temperature sensor 218.

Also as illustrated in FIGS. 6A-B, the acoustic respiration sensor 220 is mounted underneath the battery 214. In particular, the acoustic respiration sensor 220 includes rim 221 that is sandwiched between the bottom surface of the battery 214 and the bottom base 310. Accordingly, the rim 221 serves to rigidly secure the acoustic respiration sensor 220 to the bottom surface of the battery 214. The acoustic respiration sensor 220 protrudes through the aperture 502 in the bottom base 310, beyond the plane created by the bottom base 310. The acoustic respiration sensor 220 is configured to transmit vibratory motion sensed from the patient (e.g., from the patient's chest) through rigid structures of the wireless sensor 102 such that the transmitted vibratory motion is sensed by the accelerometer 210. The rigid structure includes the battery 214 and the circuit board 340.

FIG. 6C is a schematic exploded perspective view of the embodiment of the disclosed wireless sensor of FIGS. 6A and 6B. As shown, the temperature sensor 218 is mounted on the top surface of the circuit board 340. The aperture 404 extends through the mounting frame 330 and the bottom base 310 and is aligned vertically with the through-hole vias 410 (not shown in FIG. 4C) and the temperature sensor 218. The aperture 404 and the through-hole vias 410 are filled with thermally conductive material 402. Additionally, the accelerometer 210 is mounted on the top surface of the circuit board 340 over the battery 214 which is secured underneath the circuit board 340. The acoustic respiration sensor 220 (not shown in FIG. 6C) fits between the battery 214 and the bottom base 310. In some embodiments, the acoustic respiration sensor 220 abuts against the mounting frame 330 in a manner such that the acoustic respiration sensor 220, the mounting frame 330, the battery 214 and the circuit board 340 form a rigid structure capable of mechanically transmitting vibratory motion sensed by the acoustic respiration sensor 220 to the accelerometer 210 mounted on the circuit board 340. The aperture 502 extends through the bottom base 310 and is aligned vertically with battery 214 such that the acoustic respiration sensor 220 is secured to rigid structure of the wireless sensor 102. Thus the disclosed embodiment provides thermal connectivity between the patient's skin and the temperature sensor 218 and the ability for the acoustic respiration sensor 220 to mechanically transmit vibratory motion from the patient's chest to the accelerometer 210.

Advantageously, the embodiment disclosed in FIGS. 6A-C is capable of providing, among other things, three vital signs: body core temperature, pulse rate, and respiration rate. Vital signs are measurements of the body's most basic functions and are used routinely by healthcare providers to assess and monitor a patient's status. The patient's body core temperature can be provided by the temperature sensor 218. The patient's pulse rate and respiration rate can be provided by the acoustic respiration sensor 220 in combination with the accelerometer 210.

Figure 7A:
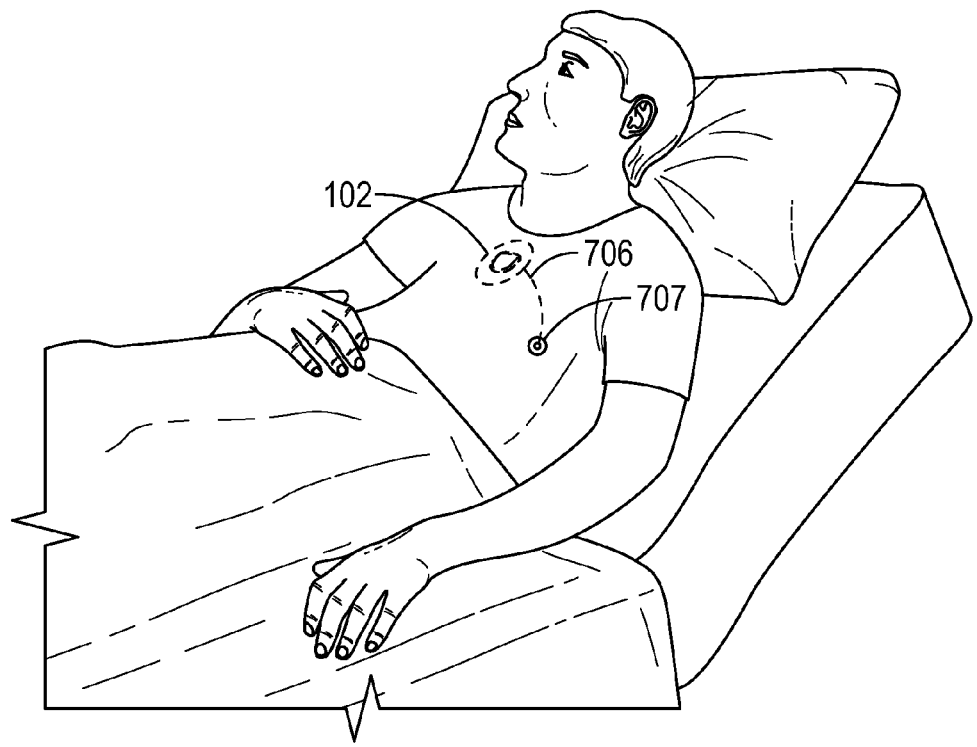
FIG. 7A is a perspective view of an embodiment of the disclosed patient monitoring system including a patient-worn wireless sensor having an ECG sensor in proximity to a patent monitor.

Referring to FIGS. 7A-F, an embodiment of the disclosed wireless sensor 102 is shown which includes an electrocardiogram (ECG) sensor 222. Chip-scale and/or component-scale ECG sensors, suitable for mounting on circuit boards are known in the art. Illustratively, by way of non-limiting example, solid state ECG sensors are offered by Texas Instruments and by Plessy Semiconductors Ltd., to name a few. FIG. 7A is a perspective view of the embodiment of the disclosed patient-worn wireless sensor 102 having an ECG sensor 222 including an ECG lead 706 that extends from the housing 350. The wireless sensor 102 is adhered to the patient's chest, for example, over the manubrium as illustrated in FIG. 7A. The ECG lead 706 extends from the housing 350 of the wireless sensor 102 to a location on the patient's chest suitable to sense electrical signals generated by the patient's heart. The ECG lead 706 is in electrical communication with an ECG electrode 707 which, in operation, is adhered to the patient's chest. In certain embodiments, the ECG electrode 707 includes conducting gel embedded in the middle of a self-adhesive pad. The ECG electrode 707 the senses electrical signals from the patient's chest and transmits the sensed signals, via the lead 706, to the ECG sensor 222. The electrode 707 adheres to the patient's skin and senses electrical signals therefrom. A skilled artisan will appreciate that many structures, forms, and formats of ECG electrodes are well known in the art and can be used to implement the ECG electrode 707.

As illustrated in FIG. 7A, the ECG lead 706 extends to the left side of the patient's chest to a position across the heart from where the wireless sensor 102 is located. Another ECG electrode 702 (described below), also in contact with the patient's skin, is formed beneath the housing 350 at the bottom base 310. Thus, a vector is formed between the ECG lead electrode 707 and the ECG electrode 702 by which the electrical signals of the patient's heart can be sensed. Illustratively, when the electrodes 702 and 707 are positioned as depicted in FIG. 7A, the ECG sensor 222 can sense ECG signals that are similar in morphology to ECG signals detected on Lead I or Lead II of a standard 12-lead ECG.

Figure 7B:
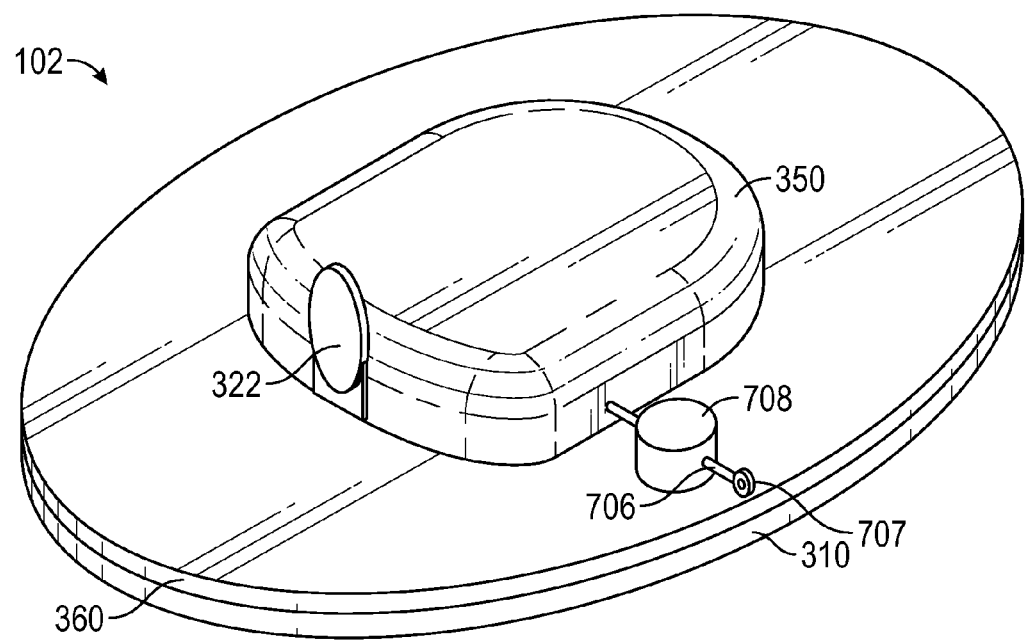
FIG. 7B is a schematic assembled perspective view of the embodiment of the disclosed wireless sensor of FIG. 7A.

FIG. 7B is a schematic assembled perspective view of the embodiment of the disclosed wireless sensor 102 of FIG. 7A. The ECG lead 706 is connected to the ECG sensor 222 (shown in FIG. 7D) which is mounted on the circuit board 340. As illustrated in FIG. 7B, the ECG lead extends through the housing 350 to a lockable retractable reel 708 that stores the ECG lead 706 in a coil when not in use. The ECG lead 706 can be extended from the reel 708 and locked in the desired position, thereby enabling placement of the ECG lead electrode 707 at a desired location on the patient's chest. In some embodiments, the locking mechanism is engaged and disengaged by applying a pulling force on the lead 706. Various forms and versions of lockable retractable reels are well known in the art and may be used to implement the reel 708.

Figure 7C:
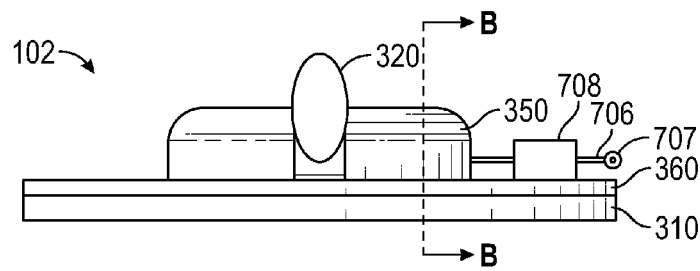
FIG. 7C is a schematic side view of the embodiment of the disclosed wireless sensor of FIGS. 7A and 7B.
Figure 7D:
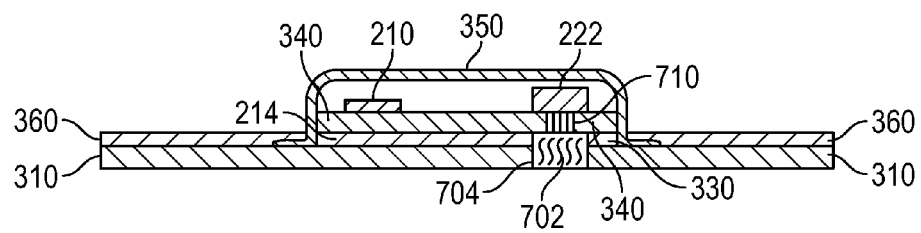
FIG. 7D is a cross-sectional view of an embodiment of the disclosed wireless sensor of FIGS. 7A-C.

FIG. 7C provides a schematic side view of the embodiment of the assembled wireless sensor 102 of FIGS. 7A and 7B with cross-section line B-B identified. FIG. 7D is a cross-sectional view of the embodiment of FIGS. 7A-C sectioned along line B-B. As illustrated in FIG. 7D, the ECG sensor 222 is mounted on the circuit board 340. To perform its sensing function, the ECG sensor 222 is in electrical contact with at least two points on the patient's skin. Two electrodes 702 and 707 are provided to achieve this purpose. While ECG electrode 707 has been described above, description of the ECG electrode 702 follows herewith.

ECG electrode 702 is located within the bottom base 310 of the wireless sensor 102. An input to the ECG sensor 222 is electrically connected to multiple through-hole vias 710 located in the circuit board 340. As previously described, through-hole vias are small vertical openings, or pathways, in the circuit board 340 through which electrically conductive material can be placed, thereby permitting transmission of electrical signals from one side of the circuit board 340 to the other side. Under the through-hole vias 710 is an aperture or opening 704 which extends through the mounting frame 330 (to form a mounting frame aperture) and through the bottom base 310 of the wireless sensor 102. The aperture 704 provides access from the ECG sensor 222 to the patient's skin when the wireless sensor 102 is worn by the patient. The aperture 704 and the through-hole vias 710 are filled with electrically conductive material to form the ECG electrode 702. Electrically conductive materials are well known in the art and can include, by way of non-limiting example, electrically conductive silicones, elastomers, polymers, epoxies, and resins, to name a few. In operation, the wireless sensor 102 is affixed to the patient's skin and the ECG electrode 702, exposed to the patient's skin, senses and transmits electrical signals from the patient's skin surface through the aperture 704 and the through-hole vias 710 to arrive at an input to the ECG sensor 222.

Figure 7E:
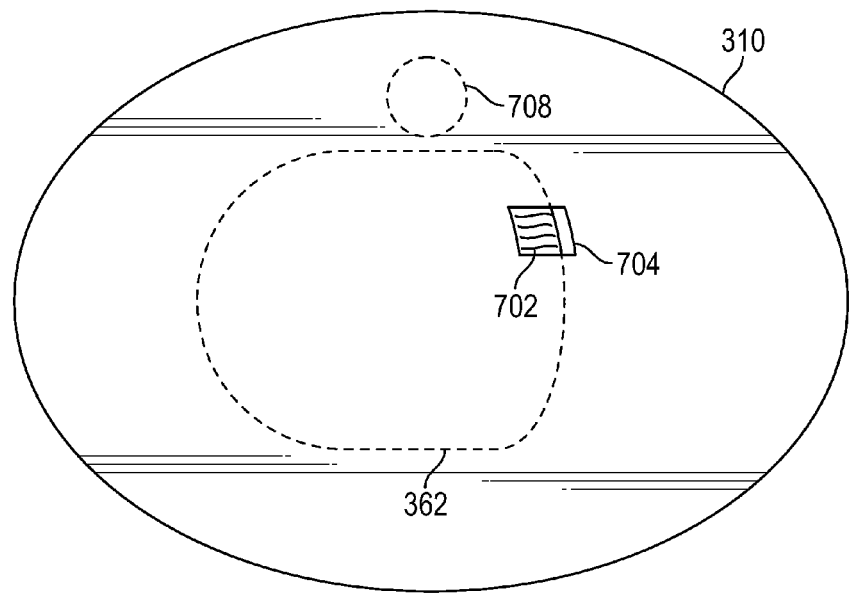
FIG. 7E is a schematic bottom perspective view of the embodiment of the disclosed wireless sensor of FIGS. 7A-D

FIG. 7E is a schematic bottom view of the embodiment of the disclosed wireless sensor of FIGS. 7A-D. The bottom surface of the bottom base 310 is illustrated. Also illustrated in phantom (i.e., dotted lines) are the outline of cut-out 362 which also indicates the position of the housing 350 in relation to the bottom surface of the bottom base 310, and the lockable retractable reel 708. The ECG electrode 702 is also illustrated as it is positioned to make contact with the patient's skin. In some embodiments, the ECG electrode may be coated with a conducting gel to improve the electrode-to-skin interface.

Figure 7F:
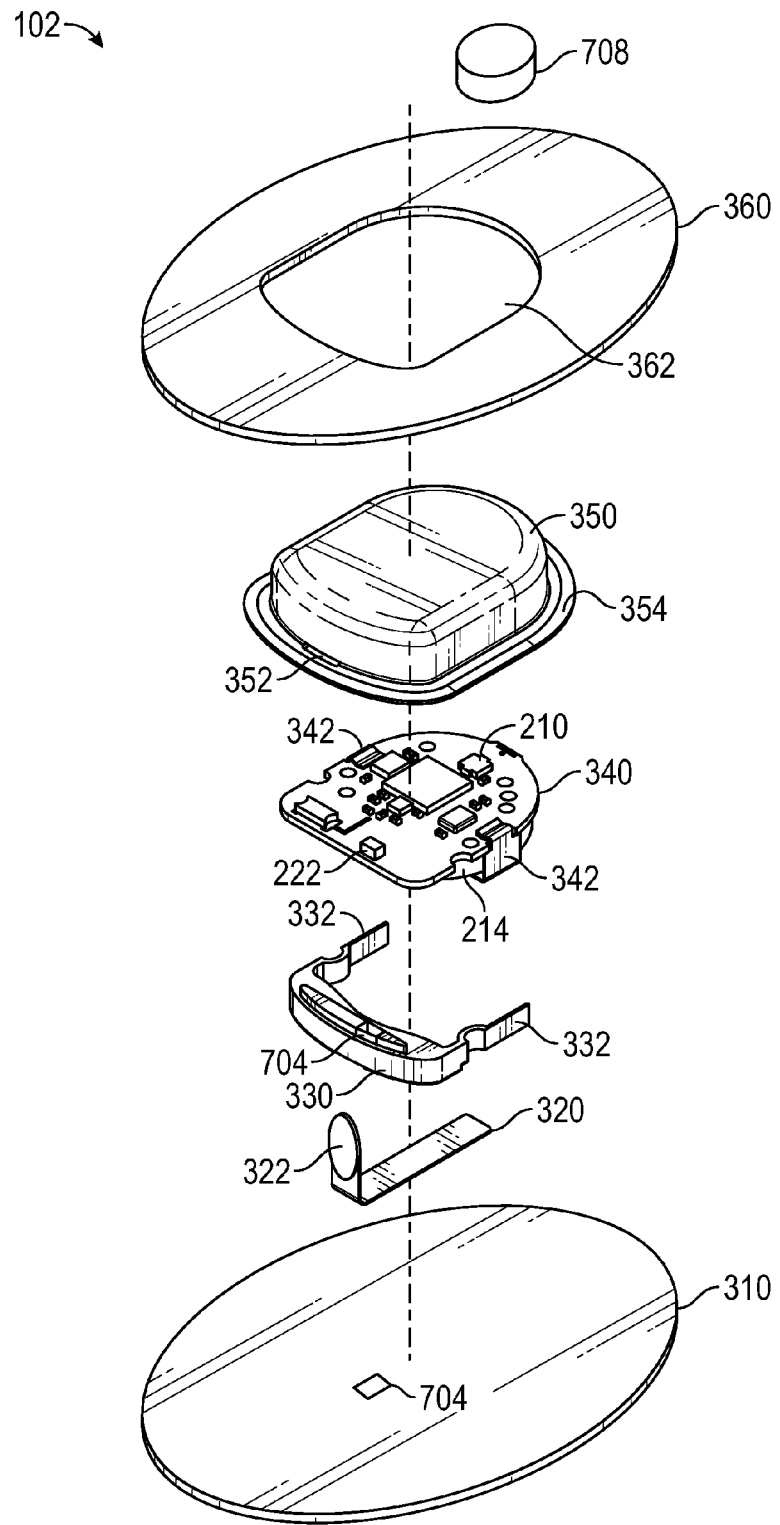
FIG. 7F is a schematic exploded perspective view of the embodiment of the disclosed wireless sensor of FIGS. 7A-7E.

FIG. 7F is a schematic exploded perspective view of the embodiment of the disclosed wireless sensor of FIGS. 7A-7E. As shown, the ECG sensor 222 is mounted on the top surface of the circuit board 340. The aperture 704 extends through the mounting frame 330 and the bottom base 310 and is aligned vertically with the through-hole vias 710 (not shown in FIG. 7F) and the ECG sensor 222. The aperture 704 and the through-hole vias 710 are filled with electrically conductive material to form electrode 702. Thus the disclosed structure provides electrical connectivity between the patient's skin and the ECG sensor 222.

Figure 8A:
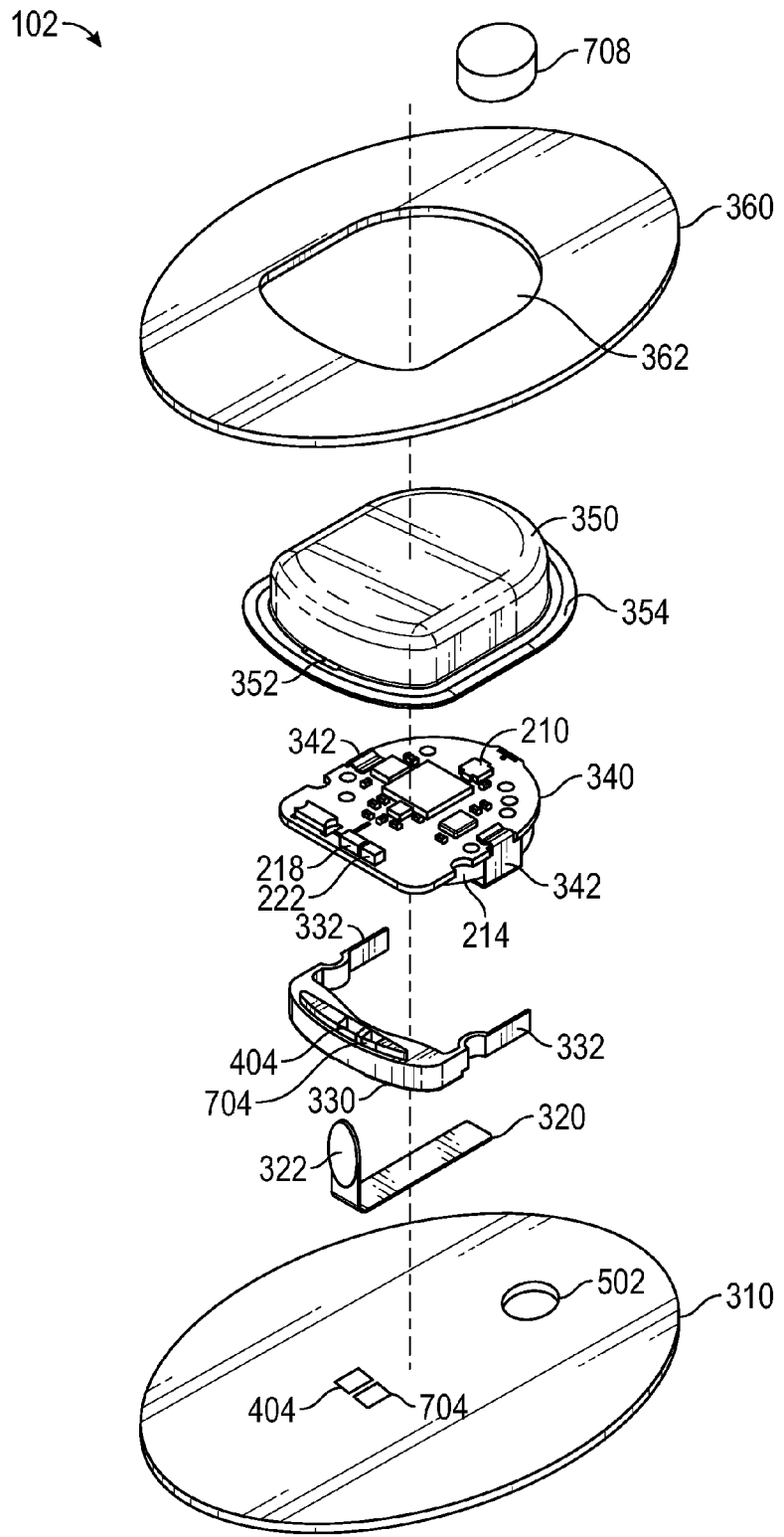
FIG. 8A is a schematic exploded perspective view of an embodiment of the disclosed wireless sensor having a temperature sensor, an acoustic respiration sensor, and an ECG sensor.
Figure 8B:
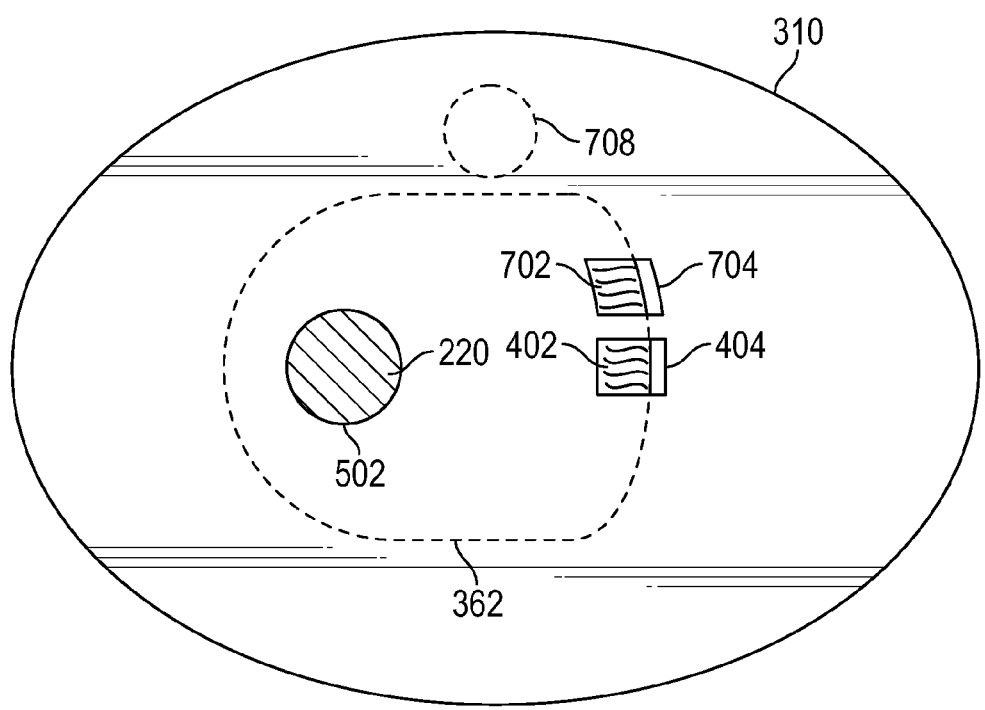
FIG. 8B is a schematic bottom view of the disclosed wireless sensor of FIG. 8A.

FIG. 8A is a schematic exploded perspective view of an embodiment of the disclosed wireless sensor having a temperature sensor 218, an acoustic respiration sensor 220, and an ECG sensor 222. FIG. 8B is a schematic bottom view of the disclosed wireless sensor of FIG. 8A. Structurally, the embodiment depicted in FIGS. 8A-B is a combination of the embodiments depicted in FIGS. 4A-C and 5A-C and 7A-F. As illustrated in FIGS. 8A-B, the temperature sensor 218 is mounted on the circuit board 340. As previously described, inputs to the temperature sensor 218 are thermally coupled to multiple through-hole vias 410 located in the circuit board 340. Under the through-hole vias 410 is an aperture 404 which extends through the mounting frame 330 and through the bottom base 310 of the wireless sensor 102. The aperture 404 provides access from the temperature sensor 218 to the patient's skin when the wireless sensor 102 is worn by the patient. The aperture 404 and the through-hole vias 410 are filled with thermally conductive material 402.

The acoustic respiration sensor 220 is mounted underneath the battery 214, held in place by rim 221 that is sandwiched between the bottom surface of the battery 214 and the bottom base 310. Accordingly, the rim 221 serves to rigidly secure the acoustic respiration sensor 220 to the bottom surface of the battery 214. The acoustic respiration sensor 220 protrudes through the aperture 502 in the bottom base 310, beyond the plane created by the bottom base 310. The acoustic respiration sensor 220 transmits vibratory motion sensed from the patient (e.g., from the patient's chest) through rigid structures of the wireless sensor 102 such that the transmitted vibratory motion is sensed by the accelerometer 210. The rigid structure through which the vibratory motion is transmitted includes the battery 214 and the circuit board 340.

The ECG electrode 702 is located within the bottom base 310 of the wireless sensor 102. An input to the ECG sensor 222 is electrically coupled to multiple through-hole vias 710 located in the circuit board 340. Under the through-hole vias 710 is an aperture or opening 704 which extends through the mounting frame 330 and through the bottom base 310 of the wireless sensor 102. The aperture 704 provides access from the ECG sensor 222 to the patient's skin when the wireless sensor 102 is worn by the patient. The aperture 704 and the through-hole vias 710 are filled with electrically conductive material to form the ECG electrode 702.

In operation, the wireless sensor 102 is affixed to the patient's skin. The thermally conductive material 402, exposed to the patient's skin, transmits thermal energy from the patient's body through the aperture 404 and the through-hole vias 410 to arrive at the inputs to the temperature sensor 218. The acoustic respiratory sensor 220 senses vibratory motion from the patient and mechanically transmits the vibratory motion to the accelerometer 210 mounted on the circuit board. And the ECG electrodes 702 and 707, exposed to the patient's skin, sense and transmit electrical signals from the patient's skin surface to arrive at inputs to the ECG sensor 222.

FIG. 8B is a schematic bottom view of the embodiment of the disclosed wireless sensor of FIG. 8A. The bottom surface of the bottom base 310 is illustrated. Also illustrated in phantom (i.e., dotted lines) are the outline of cut-out 362 and the lockable retractable reel 708. Three sensor access points are shown in FIG. 8B. The thermally conductive material 402 provides a pathway for thermal energy to be transmitted from the patient's skin the temperature sensor 218 mounted on the circuit board 340. The acoustic respiration sensor 220 is in direct contact with the patient's skin and in rigid structural contact with the accelerometer 210 so as to mechanically transmit sensed vibratory motion emanating from the patient to the accelerometer 210 mounted on the circuit board 340. And the ECG electrode 702 provides a pathway for electrical signals to be transmitted from the patient's skin to the ECG sensor 220 mounted on the circuit board 340.

In some scenarios, it may be desirable to pair, or associate, the wireless sensor 102 with the bedside patient monitor 106 to avoid interference from other wireless devices and/or to associate patient-specific information (stored, for example, on the patient monitor 106) with the sensor data that is being collected and transmitted by the wireless sensor 102. Illustratively, such patient-specific information can include, by way of non-limiting example, the patient's name, age, gender, weight, identification number (e.g., social security number, insurance number, hospital identification number, or the like), admission date, length of stay, physician's name and contact information, diagnoses, type of treatment, perfusion rate, hydration, nutrition, pressure ulcer formation risk assessments, patient turn protocol instructions, treatment plans, lab results, health score assessments, and the like. One skilled in the art will appreciate that numerous types of patient-specific information can be associated with the described patient-worn sensor without departing from the scope of the present disclosure. Additionally, pairing the wireless sensor 102 with the patient monitor 106 can be performed to provide data security and to protect patient confidentiality. Some wireless systems require the care provider to program the wireless sensor 102 to communicate with the correct patient monitor 106. Other wireless systems require a separate token or encryption key and several steps to pair the wireless device 102 with the correct bedside patient monitors 106. Some systems require the token to be connected to the bedside patient monitor 106, then connected to the wireless device 102, and then reconnected to the bedside patient monitor 106. In certain scenarios, it may be desirable to share wireless communication information between a wireless sensor 102 and a bedside patient monitor 106 without a separate token or encryption key. For security purposes, it may be desirable to use security tokens to ensure that the correct bedside patient monitor 106 receives the correct wirelessly transmitted data. Security tokens prevent the bedside patient monitor 106 from accessing the transmitted data unless the wireless sensor 102 and bedside patient monitor 106 share the same password. The password may be a word, passphrase, or an array of randomly chosen bytes.

Figure 9:
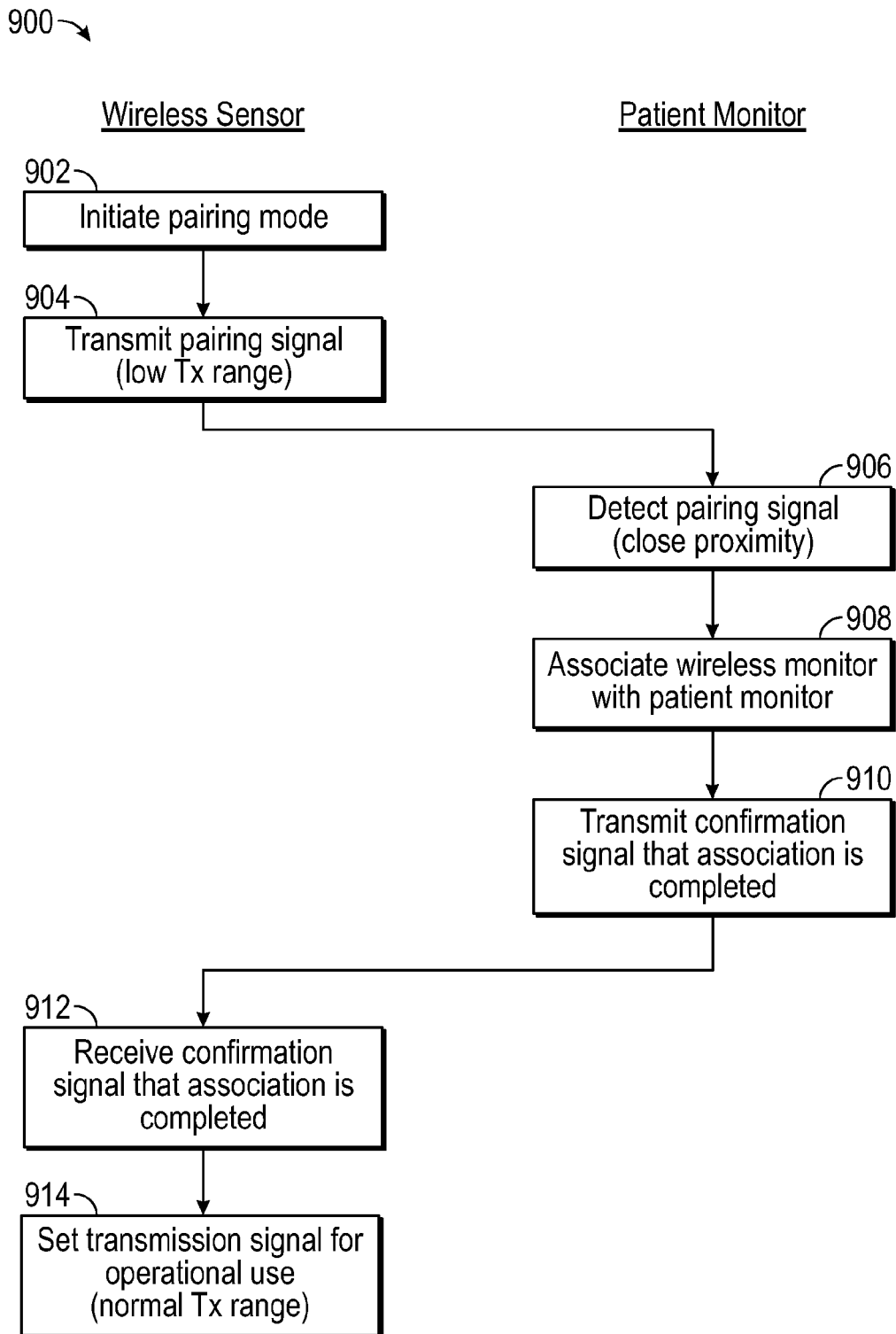
FIG. 9 is a flow diagram describing a process to associate a wireless sensor with a patient monitor according to an embodiment of the present disclosure.

FIG. 9 illustrates an exemplary method of associating a wireless sensor 102 with a patient monitor 106, which may be referred to as "pairing." At block 902 the wireless sensor 102 is set to operate in a pairing mode. In an embodiment, a user initiates the pairing mode of operation for the wireless sensor 102. This may include powering on the wireless sensor 102, switching the wireless sensor 102 to a special paring state, and/or the like. For example, in certain embodiments, the wireless sensor 102 may include a battery isolator 320 which, when removed, activates the wireless sensor 102. Upon activation, the default mode of operation is the pairing mode. In some embodiments, the wireless sensor 102 may have a button/switch 324 that can be used to activate the wireless sensor 102 and place it in the pairing mode of operation. For example, a depressible button/switch 324 can be located on the top portion of the housing 350. When the button/switch 324 is depressed and continuously held down, the wireless sensor 102 enters into the pairing mode of operation and remains in the pairing mode of operation for as long as the button/switch 324 is depressed.

As reflected at block 904, the wireless sensor 102 transmits a pairing signal indicating that it is ready to pair, or associate, with a patient monitor 106. According to some embodiments, the wireless transceiver 206 of the wireless sensor 102 is configured to emit a low-power pairing signal having a limited pairing signal transmission range. The limited pairing signal transmission range helps to prevent unintended or incidental association of the wireless sensor 102 with a patient monitor 106 that might be nearby but which is not intended to be paired with the wireless sensor 102. Such circumstances can occur in hospitals, healthcare facilities, nursing homes, and the like where patients, sensors 102 patient monitors 106 are located in close physical proximity to one another. In certain embodiments, the low-power pairing signal has a pairing signal transmission range of up to approximately three inches. In other embodiments, the low-power pairing signal has a pairing signal transmission range of up to approximately six inches. In other embodiments, the low-power pairing signal has a pairing signal transmission range of up to approximately one foot (i.e., twelve inches). A skilled artisan will recognize that other ranges can be used for the pairing signal transmission range.

Next, at block 906, the patient monitor 106, when within the pairing signal transmission range, receives the pairing signal from the wireless sensor 102. Upon detection of the pairing signal, the patient monitor 106, at block 908, associates with the wireless sensor 102 thereby configuring the wireless sensor 102 and patient monitor 106 to communicate with each other. Once the pairing is completed, the patient monitor 106 transmits a confirmation signal confirming that the patient-worn sensor 102 is associated with the patient monitor 106, thereby indicating that the paring process has been successfully completed, as reflected in block 910. At block 912, the wireless sensor 102 receives the confirmation signal. And at block 914, the wireless sensor 102 exits the pairing mode of operation and enters into a patient parameter sensing mode of operation. In the patient parameter sensing mode of operation, the patient-worn sensor 102 transmits a patient parameter sensing signal having a patient parameter sensing signal transmission range. The wireless sensor 102 increases the power of the patient parameter sensing signal transmission range to a standard operating range, such as for example, approximately three meters. In some embodiments, the patient parameter sensing signal transmission range is approximately ten feet. In some embodiments, the patient parameter sensing signal transmission range is approximately thirty feet. In certain embodiments, the paring signal transmission range is between approximately three and twelve inches, while the patient parameter sensing signal transmission range is approximately ten feet. In such embodiments, there is at least an order of magnitude difference between the pairing signal transmission range and the patient parameter sensing signal transmission range. Thus, the pairing signal transmission range is substantially less than the patient parameter sensing transmission range. Once the wireless sensor 102 enters into the patient parameter sensing mode of operation, the wireless sensor 102 is then in condition to be placed on the patient to perform sensing and monitoring functions.

In certain embodiments, an extender/repeater 107 is used to communicate with the wireless sensor 102 instead of than a patient monitor 106. Pairing with the booster/repeater may be performed in the same manner described above with respect to FIG. 9.

According to certain embodiments, the disclosed patient monitoring system 100 helps to manage a patient that is at risk of forming one or more pressure ulcers by, among other things, detecting changes in the patient's orientation and by determining how long the patient remains in the present orientation. Advantageously, the system 100 can detect when the patient is repositioned and begin timing the duration that the patient remains in that new orientation. Thus, if the patient repositions on his own without the observation of a care provider, the monitoring system 100 can detect the repositioning event and restart a timer.

The patient monitoring system 100 can aid in the administration of a clinician-established turning protocol for the patient. For example, if the patient remains in an orientation beyond a predefined, clinician-prescribed duration, the system 100 can notify the patient and/or caretakers that the patient is due to be repositioned. The wireless sensor 102 obtains sensor information indicative of the patient's orientation (e.g., acceleration data), pre-processes the sensed data, and transmits it to a processing device capable of processing the measurement data, such as, for example, the patient monitor 106. Other devices capable of processing the measurement data include, without limitation, clinician devices 114, nurses' station systems 113, the multi-patient monitoring system 110, a dedicated processing node, or the like. For ease of illustration, the description herein will describe the processing device as the patient monitor 106; however, a skilled artisan will appreciate that a large number of processing devices may be used to perform the described functions without departing from the scope of the present disclosure.

The patient monitor 106 stores and further processes the received data to determine the patient's orientation. According to some embodiments, the patient monitor 106 can determine whether the patient is standing, sitting, or lying in the prone, supine, left side, or right side positions. The patient monitor 106 can store the determined orientation information and keep track of how long the patient remains in each determined orientation, thereby creating a continuous record of the patient's positional history. In certain embodiments, the information received from the wireless sensor 102 can be used to create a time-sequenced representation of the patient's positional history. This representation can be displayed on the patient monitor 106 or transmitted to a nurses' station or other processing node to enable caregivers to monitor the patient's position in bed. The time-sequenced representation can be viewed in real time and/or be accessed for playback. For example, if an alarm alerts the caregiver that the patient has exceeded the maximum amount of time to remain in the present orientation, the caregiver can access and review the historical sequence of the patient's orientations prior to and during that period of time to determine the next orientation to which the patient may be repositioned. In some embodiments, the system 100 suggests the orientation to which the patient may be repositioned.

Illustratively, the patient monitor 106 counts the number of in-bed turns performed by the patient and displays the amount of time that has elapsed since the patient last turned. When the elapsed time exceeds a clinician-defined duration (e.g., two hours), the patient monitor 106 displays an indication that the maximum time between patient turns has been exceeded. The patient monitor 106 can also transmit a notification to clinicians responsible for caring for the patient via, for example, the multi-patient monitoring system 110, a clinician notification device 114, or the like. The patient monitor 106 can also determine and display statistical information, such as the average, minimum, and maximum amount of time between turns for a given clinician-defined time period, such as for example, twenty-four hours. The patient monitor 106 can also determine and display the number of patient turns in the same orientation over a clinician-defined period of time. Similarly, the patient monitor 106 can display the total amount of time the patient has remained in each specific orientation within a clinician-defined period. Moreover, the patient monitor 106 can determine the frequency and duration of periods that the patient remained in clinically-defined acceptable orientations.

In some embodiments of the present disclosure, the patient monitor 106 accesses the patient's health records and clinician input via the network 108. Illustratively, the patients' positional history data, analyzed in view of the patient's health records, may reveal or suggest a turning protocol (or other treatment protocol) that will likely yield favorable clinical outcomes for the particular patient. Accordingly, the patient monitor 106 analyzes the accessed information in conjunction with the received information from the wireless sensor 102 to determine a recommended patient turn protocol (or other treatment protocol) for the patient.

According to some embodiments of the present disclosure, the patient monitor 106 assesses caregiver and facility compliance with the clinician-defined turning protocol established for the patient. For example, the patient monitor 106 can identify the number of times that the patient remains in a position for a period greater than the prescribed duration, as well as the length of each such overexposure. The patient monitor 106 can also track the time between issuance of a notification, alert, or alarm and action taken in response to the event that triggered the issuance, corresponding to clinician response time.

Figure 10:
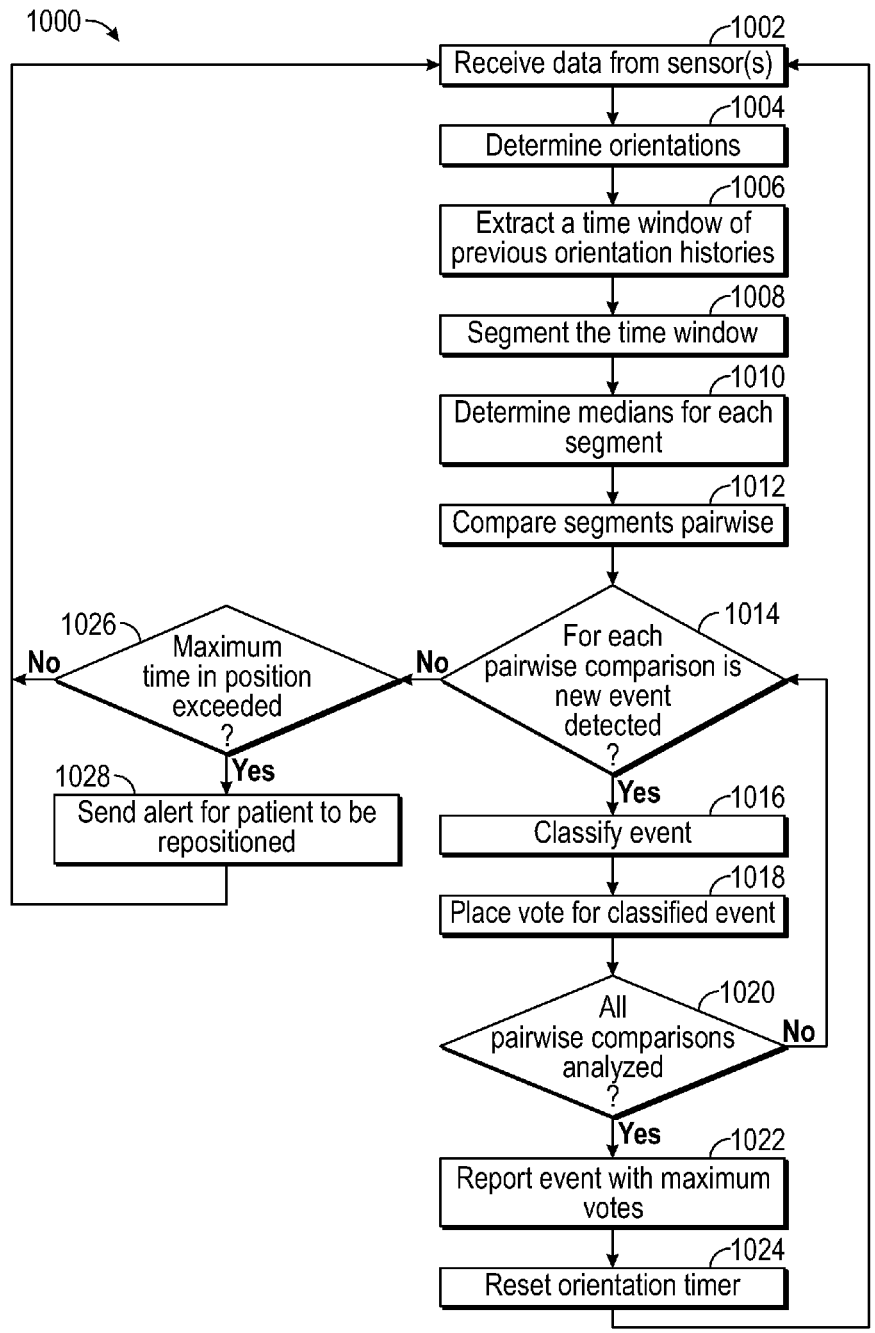
FIG. 10 is a flow diagram describing a process to determine whether a patient has changed orientation according to an embodiment of the present disclosure.

FIG. 10 illustrates a method 1000 of estimating and monitoring the orientation of a patient in bed according to an embodiment of the present disclosure. The method 1000 also identifies when the patient changes orientation and keeps track of the amount of time the patient spends in that orientation. The patient orientations that may be determined include, without limitation, whether the patient is prone, supine, on the left side, on the right side, sitting, and lying. In some embodiments, the patient monitor 106 determines the precise orientation of the patient's body. For example, the patient monitor 106 can determine the degree to which the patient's body is inclined, vertically and/or horizontally, thereby generating an accurate description of the patient's orientation relative to the support structure (such as a bed) upon which the patient lies.

According to an embodiment of the present disclosure, measurements from the accelerometer 210 of the wireless sensor 102 are used to determine the patient's orientation. The accelerometer 210 measures linear acceleration of the patient with respect to gravity. In some embodiments the accelerometer 210 measures linear acceleration in three axes. One axis, referred to as "roll," corresponds to the longitudinal axis of the patient's body. Accordingly, the roll reference measurement is used to determine whether the patient is in the prone position (i.e., face down), the supine position (i.e., face up), or on a side. Another reference axis of the accelerometer 210 is referred to as "pitch." The pitch axis corresponds to the locations about the patient's hip. Thus, the pitch measurement is used to determine whether the patient is sitting up or lying down. A third reference axis of the accelerometer 210 is referred to as "yaw." The yaw axis corresponds to the horizontal plane in which the patient is located. When in bed, the patient is supported by a surface structure that generally fixes the patient's orientation with respect to the yaw axis. Thus, in certain embodiments of the disclosed method 1000, the yaw measurement is not used to determine the patient's orientation when in bed.

Illustratively, the described method 1000 continuously or periodically (e.g., every second) determines the patient's orientation based on the measurements of pitch and roll provided by the accelerometer 210. The measurements are tracked over time, and the current measurement is compared to one or more measurements in the recent past (e.g., the previous few seconds) to determine whether an orientation change event has occurred.

The method 1000 is described in further detail herein with respect to FIG. 10. The method 1000 begins at block 1002 in which acceleration measurement data are received from the wireless sensor 102 by a device capable of processing the measurement data, such as, for example, the patient monitor 106. Other devices capable of processing the measurement data include, without limitation, clinician devices 114, nurses' station systems 113, the multi-patient monitoring system 110, a processing node, or the like. For ease of illustration, the description herein will describe the processing device as the patient monitor 106; however, a skilled artisan will appreciate that a large number of devices may be used to perform the described method 1000 without departing from the scope of the present disclosure.

The acceleration measurement data may be provided directly from the wireless sensor 102 to the patient monitor 106, or the measurement data may be relayed over a network such as network 108, by an extender/repeater 107, for example. The acceleration measurement data may be initially sampled at a sampling rate suitable to provide an acceptable degree of precision, such as for example, 100 Hz. In some embodiments, the measured data are sub-sampled by the wireless sensor 102 before being transmitted in order to reduce power consumption of the battery 214 of the wireless sensor 102. In an embodiment, the acceleration measurement data are initially sampled at 100 Hz and subsequently down-sampled, for transmission purposes, to a rate of 26 Hz. In an embodiment, the acceleration measurement data are initially sampled at a range between approximately 10 Hz and approximately 200 Hz and subsequently down-sampled, for transmission purposes, at a rate between approximately 5 Hz and approximately 40 Hz. A skilled artisan will understand that many other sampling rates and sub-sampling rates may be used.

At block 1004, the patent monitor 106 determines the present orientation of the patient. The received acceleration measurement data are processed to determine orientation values for the roll and pitch axes. The processed acceleration measurement data are provided in units of degrees, ranging from −180 degrees to +180 degrees. A lookup table, based on empirical data, provides a correlation between pairs of roll and pitch measurements and patient orientations. Illustratively, by way of non-limiting example, a roll measurement of 180 degrees can mean that the patient is on his back, and a pitch measurement of 0 degrees can mean that the patient is lying down. Thus the combination of a roll measurement of 180 degrees and a pitch measurement of 0 degrees can correspond to an orientation in which the patient is lying down on his back. Similarly, a combination of a roll measurement of 180 degrees and a pitch measurement of 90 degrees can correspond to an orientation in which the patient is lying on his right side.

Figure 11A:
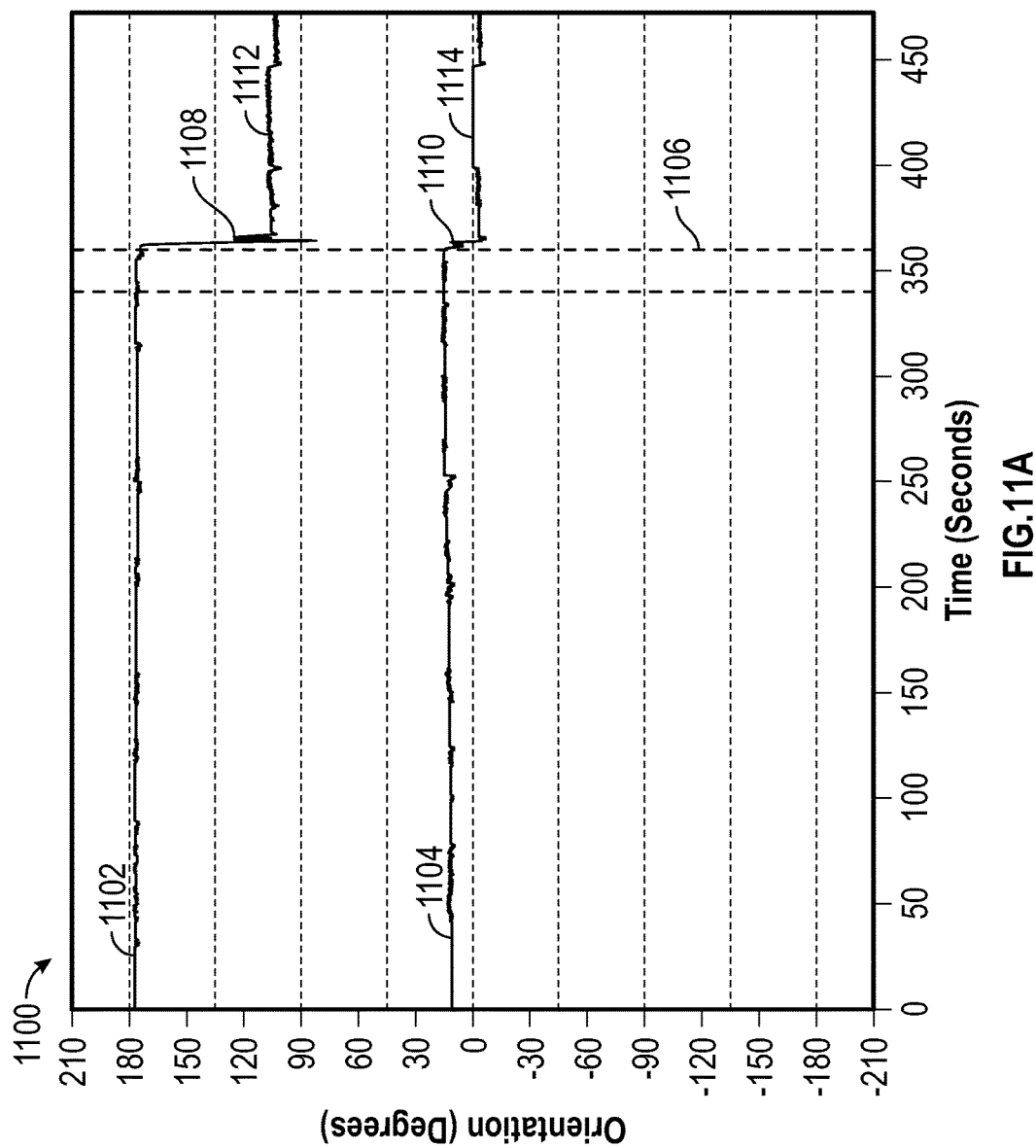
FIG. 11A is an exemplary plot of processed accelerometer data over time used to determine a patient's orientation according to an embodiment of the present disclosure.

FIG. 11A illustrates an exemplary plot 1100 of processed accelerometer 210 data over time (from 0 to 450 seconds) used to determine a patient's orientation according to an embodiment of the present disclosure. Initially, at for example, 50 seconds, the data corresponding to the roll (i.e., body length) axis 1102 is at approximately 180 degrees, indicating that the patient is on his back (i.e., in the supine orientation). The data corresponding to the pitch (i.e., hip rotation) axis 1104 is at approximately 0 degrees, indicating that the patient is reclining. Thus, combining the orientation information provided by the accelerometer 210 with respect to the roll and pitch axes 1102 and 1104, the patient is determined to be lying on his back. At approximately 360 seconds on the plot, denoted by vertical line 1106, we see that the patient changes orientation. During a short transition period, the data oscillates, as illustrated in the data representing the pitch axis at transition point 1108 and in the data representing the roll axis at transition point 1110. The oscillations can be caused by, among other things, jostling of the patient while moving from one position to the next. Shortly thereafter, the data achieves a steady state, as reflected by relatively stable graphs 112 and 114. Notably, the data indicative of the pitch axis 1102 has moved from approximately 180 degrees to approximately 90 degrees. This corresponds to a ninety-degree rotation of the patient's longitudinal body axis to the patient's right side. The data indicative of the roll axis remains at approximately zero degrees, indicating that the patient remains in the reclining position. Thus, combining the orientation information provided by the accelerometer 210 with respect to the roll and pitch axes 1112 and 1114, the patient is determined to be lying on his right side. In this manner, a lookup table of patient orientation change actions can be created. The table identifies profiles (e.g., combinations of pitch and roll axis measurements, within certain tolerances) of various possible orientations that a patient can assume while in bed. The table of profiles of patient orientation change actions can be based on empirical data that is collected and analyzed.

Referring back to FIG. 10, at block 1006, previous patient orientation determinations are extracted and combined with the current orientation determinations to form a time window of patient orientation information. For example, the time window can include information indicative of the patient's orientation from one or more time periods that are in close temporal proximity to the present information indicative of the patient's orientation, such as for example, the previous few seconds. Of course, any number of previous patient orientations can be selected for the time window. In an embodiment, the patient's orientation determinations for the previous two seconds are combined with the present determination to create a three-second time window of the patient's orientation. The purpose for creating the time window is to determine whether the patient has recently repositioned.

At block 1008, the time window is divided into segments for purposes of analysis. Any number of segments can be used for such analysis of the time window data. In an embodiment, the time window is segmented into three segments. In another embodiment, the time window is segmented into two segments. As illustrated in FIG. 11A at transition points 1108 and 1110, it is possible that the measured data used for the time window contains multiple sources of noise, some of which can have spikes of notable magnitude. To reduce the impact of the noise in the analysis, a segment value for each segment is determined. As disclosed at block 1010, the median value of the sampled data within each segment is used to determine the segment values for each segment. By taking the median value of each segment, a segment value is determined with minimal impact of potential noisy spikes. In certain embodiments, the segment value is a vector comprising values corresponding to each axis of measured data. Illustratively, by way of non-limiting example, each segment value comprises a vector including a roll axis segment component and a pitch axis segment component. According to some embodiments, the units of the determined segment values and/or segment components are in units of degrees ranging from −180 degrees to +180 degrees.

At block 1012 the median values of each segment are pairwise compared. Illustratively, by way of non-limiting example, a time window that is segmented into three sections would have three pairwise comparisons: the first segment value compared to the second segment value, the first segment value compared to the third segment value, and the second segment value compared to the third segment value.

At block 1014, each pairwise comparison is analyzed to determine whether an orientation change event occurred. The determination is made by comparing the magnitude of the difference of each pairwise comparison with a predetermined threshold value. If the magnitude of the difference of a pairwise comparison exceeds the threshold, then an orientation change event is considered to have occurred. If the magnitude of the difference of a pairwise comparison does not exceed the threshold, then no change in orientation is considered to have occurred. Thus, a change that exceeds a certain threshold in the roll dimension corresponds to an orientation change event that includes a rotation about the longitudinal axis of the patient's body. Similarly, a change that exceeds a certain threshold in the pitch dimension corresponds to an orientation change event that includes a transition from sitting up to lying down, or vice versa. A change that exceeds a certain threshold in both the roll and pitch dimensions corresponds to and orientation change event that includes a rotation about the longitudinal axis of the patient's body and a transition from sitting up to lying down, or vice versa. According to an embodiment, the threshold is 45 degrees and thus, if the magnitude of difference between any two segment values is greater than 45 degrees, then an orientation change event is determined to have occurred. In another embodiment, an additional comparison is made between consecutive one-second segments of data to determine whether a change of at least 30 degrees has occurred. This is to prevent repeated posture changes, when for instance, the patient is in a posture near 135 degrees, that is, right in the middle between two postures.

If an orientation change event is determined to have occurred, then at block 1016, the detected event is classified. Reference is made to a look-up table of events which includes a set of profiles of orientation change actions or activities. In an embodiment, each profile includes four data points: a "before" and an "after" measurement for the roll axis, and a "before" and an "after" measurement for the pitch axis. For example, as illustrated in FIG. 11A, the profile of the orientation event activity of turning from lying on the back to lying on the right side can be as follows:

TABLE 1

| Roll Before | Roll After | Pitch Before | Pitch After |
|---|---|---|---|
| 180 degrees | 90 degrees | 0 degrees | 0 degrees |

As illustrated in Table 1, the roll axis changes from 180 degrees to 90 degrees indicating that the patient rotated from lying on his back to lying on his right side. The pitch axis does not change because the patient remains in a reclining orientation. The table of events is developed and updated off-line and is based on the analysis of empirical data of known orientation change events. Accordingly, classification of orientation change events can be performed by identifying in the look-up table of events the orientation event profile that matches the data of the pairwise comparison when the magnitude of the difference of the pairwise comparison exceeds the predetermined threshold.

At block 1018, a vote is placed for the classified event. Illustratively, for the example described with respect to Table 1, the vote would be for the orientation change event profile of turning from lying on the back to lying on the right side. At block 1020, the method 1000 repeats the acts of determining whether an orientation change event occurred, classifying the orientation change event (if an event occurred), and voting for the classified orientation change event (again, if an event occurred), for each pairwise comparison. The maximum number of iterations for these blocks will be equal to the number of segments in the time window.

Once all of the pairwise comparisons have been analyzed, at block 1022, the method 1000 tallies the votes recorded at block 1018. The orientation change event that has the most votes is determined to be the orientation change event that occurred. The determined orientation change event is then reported as the orientation of the patient. At block 1024, an orientation duration timer is reset to keep track of the time the patient remains in the new orientation. The method 1000 then returns to block 1002 to begin the analysis again with respect to the next incremental (e.g., second) of measurement data.

If at block 1014, none of the pairwise comparisons result in a detected orientation change event (i.e., the patient has remained in the same orientation throughout the entire time window) then the method 1000 progresses to block 1026 to determine whether the patient has remained in the present orientation for a period of time greater than a predefined maximum duration, which may also be referred to herein as a predetermined duration or a predetermined maximum duration. If not, the method 1000 returns to block 1002 to begin the analysis again with respect to the next incremental set (e.g., second) of measurement data. If the patient has remained in the present orientation for a period of time greater than the predefined maximum duration, then at block 1028, an alert is sent to, for example, the patient's caregiver, to notify the caregiver that the patient should be repositioned. The method 1000 then returns to block 1002 to begin the analysis again with respect to the next incremental (e.g., second) of measurement data.

Figure 11B:
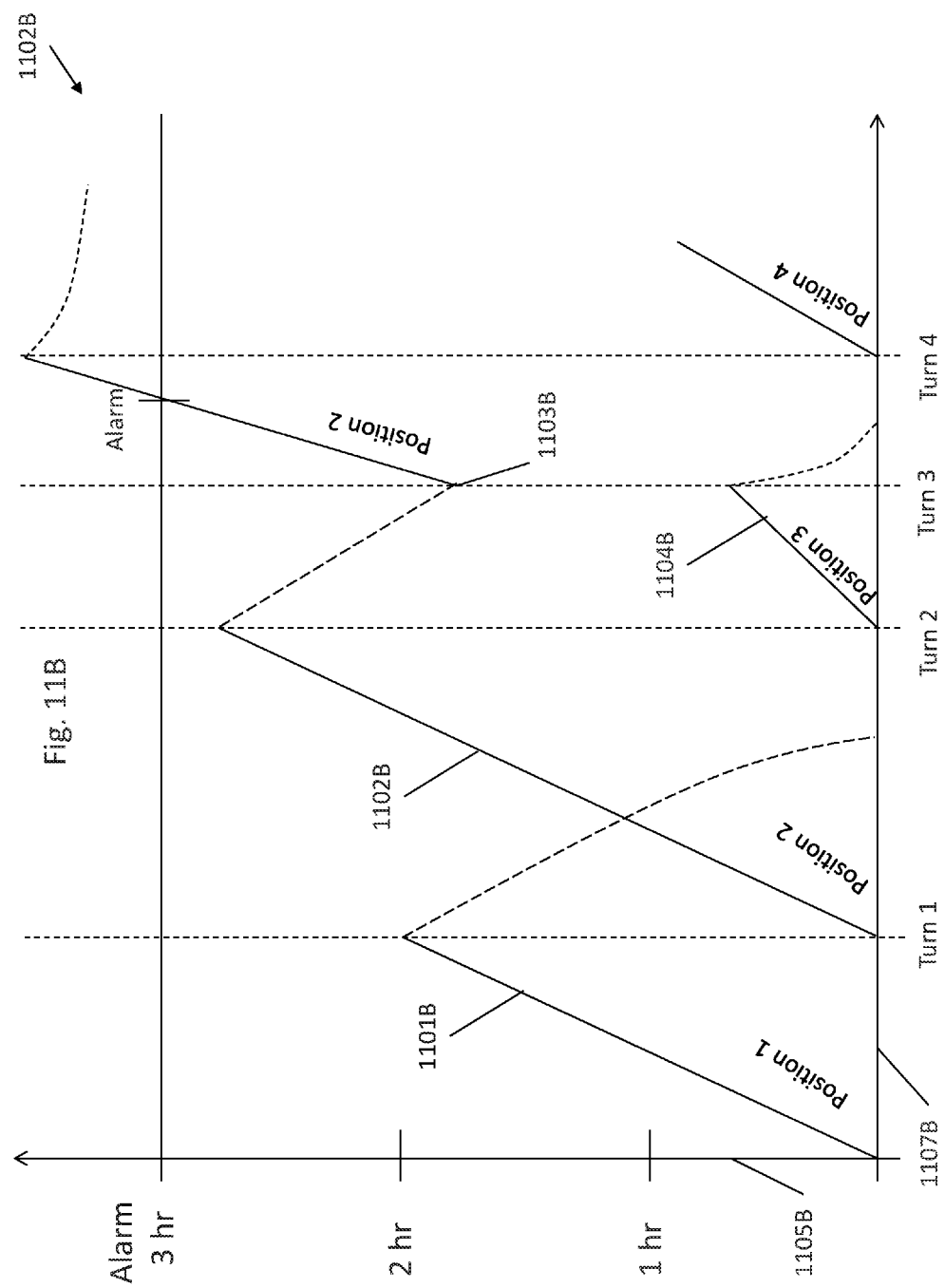
FIG. 11B is an exemplary plot of the duration of a patient's orientation according to an embodiment of the present disclosure.

FIG. 11B is an exemplary plot of an embodiment of a patient position monitoring paradigm for determining when a patient's orientation needs to be changed, according to an embodiment of the present disclosure. In an embodiment, the plot 1102B may be part of a display to a caregiver on a bedside monitor, a multi-room monitor, both, or the like. The plot can be updated in real time, at predefined intervals, and/or manually. In other embodiments, the paradigm may be illustrative of the signal processing performed by a signal processor to determine when to activate an alarm informing a caregiver of the potential of a pressure ulcer if a patient is not repositioned. In these embodiments, each portion of the paradigm may be customized to a particular patient, patient demographics, hospital protocol, unit protocol such as, for example, a protocol specific to a surgical IOU or other hospital unit, home care, or the like.

In the illustrated embodiment, a patient's position is monitored over time. A vertical axis 1105B represents time and a horizontal axis 1107B represents a patient movement event, such as, for example, In the illustrated embodiment, an alarm is set to alert a caregiver when a patient has been in a certain position for 3 hours or more. The illustrated embodiment is a non-limiting example, as the alarm can be set to alert the caregiver at 1 hour, 2 hours, 3 hours, 4 hours, 5 hours, 6 hours, 7 hours. 8 hours, 9 hours, and/or 10 or more hours. The alarm can include a noise, color, and/or other indicator that will alert the caregiver. In some embodiments, the alarm can indicate to the caregiver that the patient has remained in the same position for a threshold amount of time (e.g., 3 hours). The threshold amount of time can be predefined or adjusted over time. In some embodiments, the alarm indicates to the caregiver that the patient has fallen, moved into an incorrect position, left the bed and/or the like. In an embodiment, empirical data about a particular patient, or a group of like patients, can be used to customized some or all of the parameters for the alarm discussed herein.

As shown in FIG. 11B, the monitor begins monitoring a patient as the patient is in Position 1 (e.g., the patient is lying on their back, side, front, sitting slightly up, sitting mostly up, or the like). As the patient remains in Position 1, a timing mechanism starts and a line 1101B as its growth line. The slope of the line 1101B depicts a growth rate as the patient remains in the same position. As shown in the illustrated embodiment, the growth rate can be depicted linearly. In some embodiments, the grown rate can be linear, non-linear, exponential, and/or the like. In some embodiments, the growth rate is predefined. In some embodiments, the growth rate can change in real time and/or adjust to various physiological parameters and/or empirical data, as described below. The growth rate can depend on a number of factors and empirical data already known and/or determined by the system, depending on for example, how the patient's skin reacts to remaining in a single position, how fast negative effects experienced by the patient (e.g., pressure sores) form or heal, the particular position the patient is lying in, and/or demographic information about the patient, including the patient's age, health, blood perfusion rates, hydration, and/or nutrition, among others. Accordingly, in some embodiments, the growth rate can indicate a growth rate of the effects (e.g. bed sores) as the patient remains in the same position (e.g., Position 1) over a period of time.

As illustrated in FIG. 11B, the patient remains in Position 1 for approximately 2 hours. At that time, the patient turns and/or is turned by a caregiver to Position 2. In the illustrated embodiment, Position 2 is a different position from Position 1. When the patient turns and/or is turned, the timing mechanism can restart a new line 1102B and begin to measure, track, monitor, and/or calculate the amount of time the patient remains in Position 2.

A the same time, line 1101B transforms into its decay line. The decay line of line 1101B can comprise data relating to a decay rate of a bed sore, potential bed sore, particular area of a patient's skin, and/or the amount of time the patient or a group of like patients, or all patients, takes to recover from remaining in a particular position (e.g., Position 1), among other things. Similar to the growth rate, the decay rate can be linear, non-linear, and/or exponential, among others. In some embodiments, the decay rate is predefined. In some embodiments, the decay rate can change in real time and/or adjust to various physiological parameters and/or empirical data, as described below. The decay rate may depend on a number of factors and empirical data, depending on for example, how the patient's skin reacts to remaining in a single position, how fast negative effects experienced by the patient (e.g., pressure sores) heal, how quickly the patient recovers, the particular position the patient is lying in, and/or demographic information about the patient, including the patient's age, health, blood perfusion rates, hydration, and/or nutrition, among others. As shown in the illustrated embodiment, when the patient is in one or more positions that are not Position 1, the decay line of Position 1 continues to decay at the decay rate. That is, in an embodiment, the decay line of Position 1 will continue to decay at its decay rate through one or multiple other positions until it approaches zero so long as that other one or multiple positions do not include Position 1. In this example, the decay rate, or recovery rate for example, approaches zero more quickly the longer the patient remains not in Position 1.

In the illustrated embodiment, the patient turns and/or is turned again at Turn 2. Turn 2 occurs at a time before the threshold amount of time is reached, and therefore, before the alarm alerts the caregiver to turn the patient. At Turn 2, the patient turns/is turned to Position 3. In some examples, Position 3 is the same as Position 1. In such embodiments, because the decay line of line 1101B associated with the previous Position 1 has reached zero, a line 1104B starts at zero as its growth line for Position 3/1. However in some examples, Position 3 is a different position from Position 1. In the illustrated example, Position 3 is different from Position 1 and its growth rate for line 1104B is different from that of Position 1. In some examples, the decay line of Position 1 can continue to decay as the decay line of Position 2 continues to decay when the patient turns and/or is turned to Position 3 as long as Position 3 is different from Positions 1 and 2. In this example, the patient can continue to heal as a result of the effects of remaining in both Positions 1 and 2. In some examples, Position 1 continues to decay as the patient turned and/or is turned to multiple positions, such as a second, third, fourth, and/or fifth or more positions.

As shown in the illustrated embodiment, the patient remains in Position 3 for a relatively short period of time. During that time, any effects of remaining in Position 2 begin to decay. Thereafter, however the patient turns and/or is turned back to Position 2. Advantageously, rather than restarting at time zero, the system can determine that the patient has turned back to Position 2 and the timing mechanism begins timing from the current value of the decay line of Line 1102B, which corresponds to point or time 1103B. Time 1103B is greater than zero in this example, but less than the threshold amount of time. Additionally, in this example, the time 1103B is less than the amount of time the patient originally remained in Position 2. In some embodiments time 1103B can be equal to the time the patient turned from Position 2. However, in the illustrated embodiment, the system can take into account the decay rate and the time the patient has spent recovering from remaining in Position 2. Thus, in the illustrated embodiment, Time 1103B can be determined by the system through a number of methods. For example, the system can subtract the recovery time from the growth time, and/or count down from the time of the turn (e.g., Turn 2), among other methods. Advantageously, the preferred embodiment of the system can ensure the patient does not exceed the threshold total time, taking into account the growth and decay rate, a patient spends in a particular location. Although in an embodiment, the system restarts the timer at each turn, without accounting for the previous time the patient spent at a particular position, such embodiments may not be as precise in allowing adequately recovery of tissue, blood pooling, or the like caused by the previous position, and therefore, a patient may be more likely to experience negative effects (e.g., bed sores). Accordingly, the preferred embodiment of the system can more precisely reduce a likelihood of a patient developing harmful effects, such as bed sores by ensuring a patient would not remain in a particular position for too long. Once the total time spent in a position, taking into account the patient's growth and decay rates, reaches the threshold time (e.g. 3 hours in this example), an alarm can alert the caregiver.

In some embodiments, the alarm will alert the caregiver until the patient turns and/or is turned again, for example as illustrated by Turn 4 in FIG. 11B. In some embodiments, the growth line will continue to grow, thus requiring longer for the line to decay, when a patient has not been turned within the threshold time. Such continued growth ensures that a patient will not be too soon returned to a position where the patient spent too much time and can help ensure that the corresponding tissue has sufficient time to recover from a particular patient position. In an embodiment, the decay rate of the line is adjusted to account for exceed the threshold limit. As shown in the illustrated embodiment, the decay rate is reduced after exceed a threshold, meaning it will take longer for the line corresponding to the alarmed position to reach zero.

As discussed, in an embodiment, when the patient turns and/or is turned after the time of the alarm, the growth line will exceed the threshold time, as indicated by the plot of FIG. 11B. Once the patient turns and/or is turned, the decay line can be shown above the threshold (e.g. alarm) line. In some examples, the patient may take longer to recover when the time spent in a particular position exceeds the threshold time. In some examples, the alarm can alert the caregiver that the decay line has reached the threshold time as the line continues to decay towards zero and the patient remains in a different position. In some embodiments, the alarm does not alert the caregiver that the decay line has passed the threshold time.

According to certain embodiments of the present disclosure, the patient monitor 106 determines the mobility status of the patient, e.g., whether the patient is ambulatory, standing, sitting, reclining, or falling. The wireless monitoring system 100 can include an alert system to alert the caregiver that the patient is falling, getting out of bed, or otherwise moving in a prohibited manner or in a manner that requires caregiver attention. The alert can be an audible and/or visual alarm on the monitoring system or transmitted to a caregiver (e.g., nurses' station system 113, clinician device 114, pager, cell phone, computer, or otherwise). Illustratively, the patient monitor 106 can display the patient's mobility status and transmit a notification that the patient is active and away from the bed. In some circumstances, the patient monitor 106 can determine whether the patient contravenes a clinician's order, such as, for example, instructions to remain in bed, or to walk to the bathroom only with the assistance of an attendant. In such circumstances, a notification, alert, or alarm can be transmitted to the appropriate caregivers.

In certain aspects, the information received from the wireless sensor 102 can be used to create a time-sequenced representation of the patient's movement. This representation can be displayed on the patient monitor or transmitted to a nurses' station or other processing node to enable the caregiver to monitor the patient. The time-sequenced representation can be viewed in real time and/or be recorded for playback. For example, if an alarm alerts the caregiver that the patient has fallen, the caregiver can access and review the historical sequence of the patient's movements prior to and during that period of time.

In some embodiments, the patient monitoring system 100 can predict a patient's risk of falling based on analysis of the patient's movement (e.g., gait) and other information (such as, for example, the patient's current medication regimen). When the patient monitor 106 determines that the patient's risk of falling is above a predetermined threshold, the patient monitor 106 can issue an alarm or alert to notify care providers of the identified risk in an effort to anticipate and therefore prevent a patient fall. Additionally, the patient monitor 106 can determine when a patient has fallen and issue the appropriate alarms and alerts to summon care provider assistance.

Figure 12:
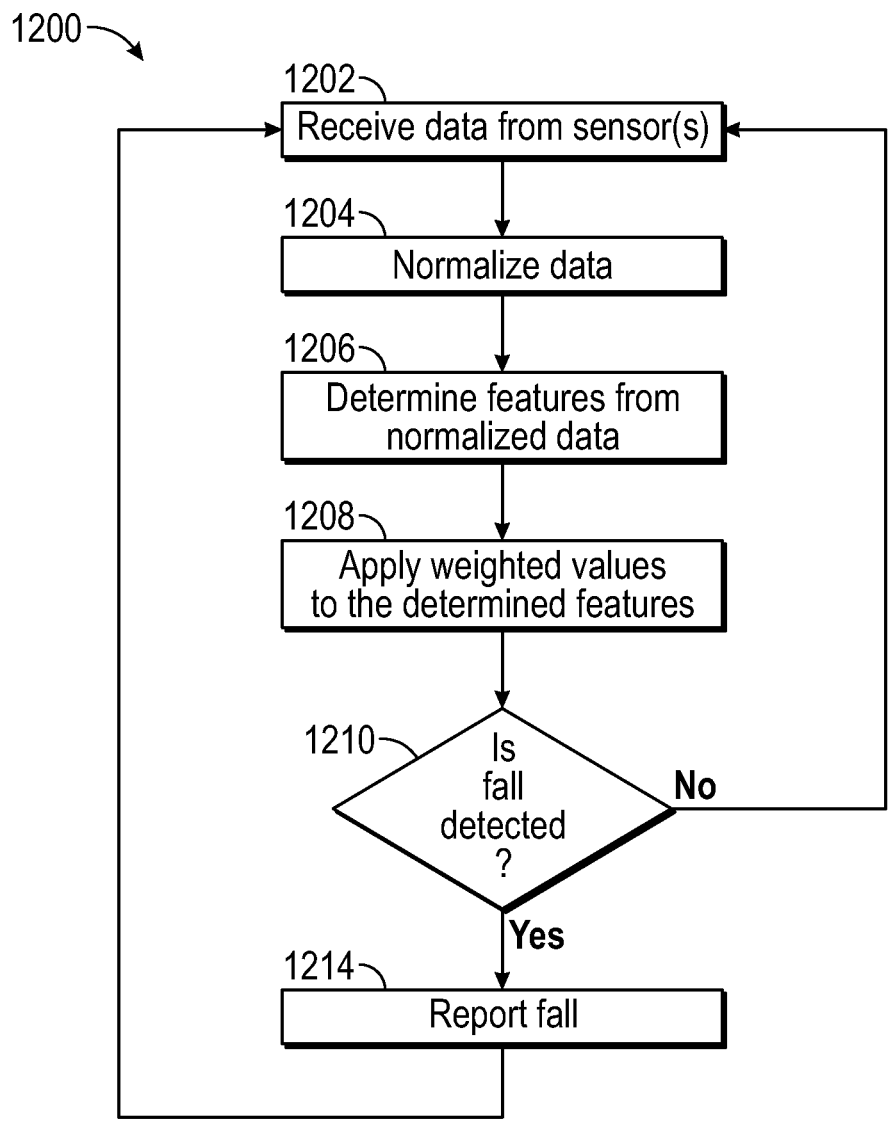
FIG. 12 is a flow diagram describing a process to determine whether a patient has fallen according to an embodiment of the present disclosure.
Figure 13A:
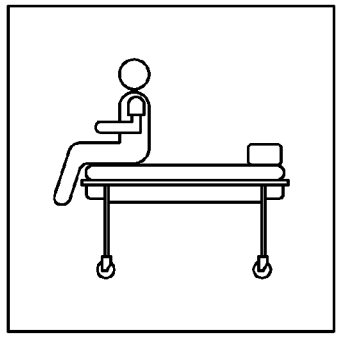
FIGS. 13A-F illustrate embodiments of displays reflecting a patient's position according to an embodiment of the present disclosure.
Figure 13B:
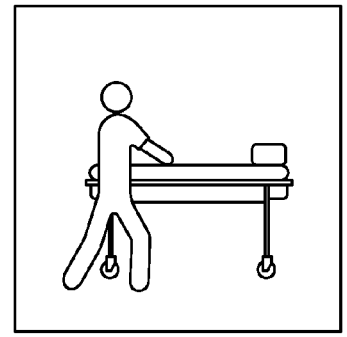
Figure 13C:
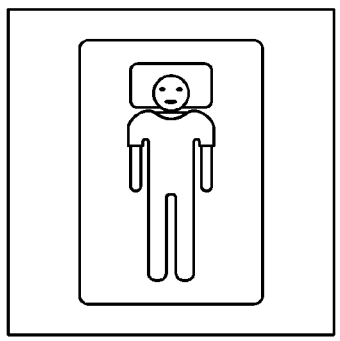
Figure 13D:
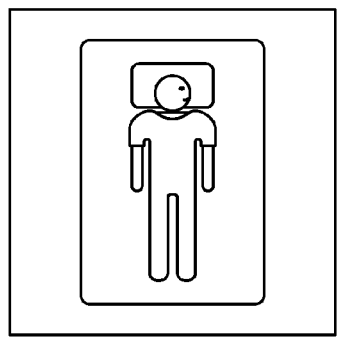
Figure 13E:
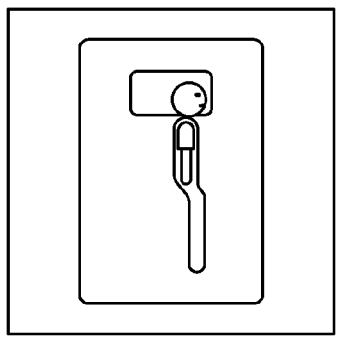
Figure 13F:
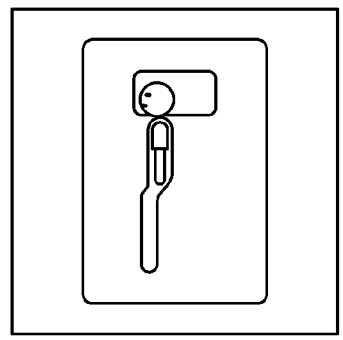

FIG. 12 illustrates a method 1200 of determining whether a patient has fallen according to an embodiment of the present disclosure. The method 1200 uses, among other things, information sensed by the accelerometer 210 and by the gyroscope 212 of the wireless sensor 102 to determine whether the patient has fallen. The method 1200 can be performed by the wireless sensor 102, using its processor 202 and storage device 204, or it can be performed by an external processing device that receives the sensed information from the wireless sensor 102, such as, for example, the patient monitor 106.

According to an embodiment of the present disclosure, measurements from the accelerometer 210 and the gyroscope 212 of the wireless sensor 102 are used, among other things, to determine whether the patient has fallen. As discussed above, the accelerometer 210 measures linear acceleration of the patient with respect to gravity in three axes. The three axes of the accelerometer 210 are represented in fixed, inertial references. The roll axis corresponds to the longitudinal axis of the patient's body. Accordingly, the roll reference measurement is used to determine whether the patient is in the prone position (i.e., face down), the supine position (i.e., face up), or on a side. The pitch axis corresponds to the locations about the patient's hip. Thus, the pitch measurement is used to determine whether the patient is upright or lying down. Advantageously, the pitch axis provided by the accelerometer 210 can be a useful source of information in determining whether a patient has fallen because it can indicate a change in the patient's orientation from standing to lying, a frequently-seen scenario when a patient falls. The yaw axis corresponds to the horizontal plane in which the patient is located.

The gyroscope 212 provides outputs responsive to sensed angular velocity of the wireless sensor 102, as positioned on the patient, in three orthogonal axes corresponding to measurements of pitch, yaw, and roll. In contrast to the fixed, inertial reference frame relative to gravity of the accelerometer 210, the frame of reference provided by the gyroscope is relative to the patient's body, which moves.

At block 1202, the method 1200 begins in which acceleration measurement data and angular velocity data are received from the wireless sensor 102 by a device capable of processing the measurement data, such as, for example, the patient monitor 106. Other devices capable of processing the measurement data include, without limitation, clinician devices 114, nurses' station systems 113, the multi-patient monitoring system 110, or the like. For ease of illustration, the description herein will describe the processing device as the patient monitor 106. A skilled artisan will appreciate that a large number of devices may be used to perform the described method 1200 without departing from the scope of the present disclosure.

At block 1204, the received data are normalized, which may also be referred to as "scaling," to adjust values measured on different scales to a common scale, prior to further processing. According to an embodiment, training data are used to normalize the received data. The training data can include empirical data of multiple fall scenarios as well as non-fall scenarios that can be challenging to discriminate from fall scenarios. The training data are collected and analyzed to serve as the basis for establishing a weight vector (discussed below with respect to block 1208) used to determine whether a patient has fallen. The training data can include multiple falling and non-falling scenarios, performed multiple times, by multiple subjects. Illustratively, by way of non-limiting example, the training data can include the fall and non-fall scenarios described in Table 2.

TABLE 2

| Fall and Non-Fall Scenarios |
| --- |
| Fall forward from vertical, ending in left/right lateral position |
| Fall forward from vertical, ending in prone position |
| Fall backward, from vertical, ending in left/right lateral position |
| Fall backward from vertical, ending in supine position |
| Fall to left/right from vertical, ending in left/right lateral position |
| Fall to left/right from vertical, ending in prone position |
| Fall to left/right rom vertical falling, ending in supine position |
| Collapse from vertical, ending in left/right lateral position |
| Collapse from vertical, ending in prone position |
| Collapse from vertical, ending in supine position |
| Fall from vertical onto knees |
| Fall from vertical to the left/right against a wall, sliding down |
| Take a step down repeatedly from a podium with left foot first |
| Take a step down repeatedly from a podium with right foot first |
| In bed: roll onto left/right side, falling out of bed |
| Sit down from vertical into a chair |
| Jump off mattress repeatedly |
| Stand quietly |
| Stumble vigorously and fall onto mattress |

As with the received data, each sample of the training data includes six dimensions of information, corresponding to the three axes of accelerometer 210 data, and the three axes of gyroscope 212 data. Normalizing the received data standardizes the range of the variables of the received data. Since the range of values of raw data can vary widely, analytical algorithms may not work properly without normalization. For example, many classifiers calculate the distance between two points. If one of the independent variables has a broad range of values, the distance will be governed by this particular variable. Therefore, the range of all variables can be normalized so that each feature contributes approximately proportionately to the final distance. Normalization causes the values of each variable in the data to have zero-mean (when subtracting the mean in the numerator) and unit-variance. This can be performed by calculating standard scores. The general method of calculation is to determine the distribution mean and standard deviation for each variable of the entire set of training data. Next each determined mean is subtracted from the corresponding variable of the received data. Then the new value of each variable (having the mean already subtracted) is divided by the determined standard deviation. The result is a normalized set of values that can be further processed by the method 1200.

At block 1206, the normalized set of values is processed to determine features that are useful in determining whether a patient is falling. According to an embodiment, the method determines the following five features: the magnitude of the acceleration data (provided by the accelerometer 210), the magnitude of the angular velocity data (provided by the gyroscope 212), the magnitude of the jerk (i.e., the rate of change of acceleration); the fall duration which is used to characterize a fall starting point and a fall impact point, and the change in pitch between two consecutively received data points. Other features can features can be used in determining whether a patient is falling such as, by way of non-limiting example, vertical velocities.

The magnitude of the received acceleration data is determined by calculating the Euclidian norm of the three-dimensional vector made up of the measurements from the accelerometer's 210 three axes. As is well understood by an artisan, this corresponds to the square root of the sum of the squares of the three accelerometer values, pitch, roll and yaw. Similarly, the magnitude of the angular velocity data is determined by calculating the Euclidian norm of the three-dimensional vector made up of the measurements from the gyroscope's 212 three axes. The magnitude of the jerk, which can also be referred to as "jolt," "surge," or "lurch," is calculated by taking the derivative of the acceleration vector, and then calculating the Euclidean norm of the derivative.

The fall duration, which is a scalar value, is determined by evaluating the acceleration magnitude profile of the patient's motion over a short duration of time. In particular, as the fall begins, acceleration of the patient relative to gravity decreases because the patient is falling. (A patient that is not falling would register an acceleration value in the up and down dimension equal to the force of gravity (i.e., 1 g or approximately 9.80665 m/s$^2$). Thus, if the magnitude of the acceleration is below a first threshold, then it is considered to be a starting point of a fall, and the value of the fall duration is incremented by 1. If the magnitude of the acceleration is above the first threshold, then the value of the fall duration is decremented by 1. In an embodiment, the first threshold is 0.6 g (or approximately 5.88399 m/s$^2$). A second threshold is used to determine the impact point of the fall. In an embodiment, the second threshold is 0.8 g (or approximately 7.84532 m/s$^2$). If the magnitude of the acceleration is below the second threshold, then it is considered to be an impact point of the fall, and the value of the fall duration is incremented by 1. If the magnitude of the acceleration is above the second threshold, then the value of the fall duration is decremented by 1.

The pitch change feature is the result of a comparison of the present pitch orientation (as determined by the accelerometer 210 data) with the pitch orientation determined one second earlier. As discussed above, the pitch dimension of the accelerometer data is useful in detecting a fall because it distinguishes between the patient being in an upright position (e.g., standing up or sitting up) and reclining. Thus a change in pitch from being upright to reclining can indicate that a fall has occurred. The output of block 1206 is a five-dimensional feature vector made up of the five determined features.

At block 1208, a weight vector of values is applied to the determined features. According to certain embodiments, the inner product of the received five-dimensional feature vector and a weight vector is calculated. In certain embodiments, the weight vector is derived using a machine learning algorithm. Machine learning is a sub-field of computer science based on the study of pattern recognition and computational learning theory in artificial intelligence. It includes the development of algorithms that can learn from and make predictions on data. Algorithms developed through machine learning operate by building a model from example inputs in order to make data-driven predictions or decisions, rather than following strictly static program instructions. Machine learning is employed in a range of computing tasks where use of explicit computer programs is infeasible. When employed in industrial contexts, machine learning methods may be referred to as predictive analytics or predictive modelling. As applied in the present disclosure, the machine learning system includes supervised learning, where the machine learning algorithm is presented with training data that include example inputs and their known outputs, given by a "teacher", and the goal is to learn a general rule that maps the inputs to the outputs. In an embodiment, Fisher's linear discriminant is employed to derive the weight vector. Fisher's linear discriminant is a method used to find a linear combination of features that characterizes or separates two or more classes of objects or events. The resulting combination may be used as a linear classifier or for dimensionality reduction before later classification. Other methods of machine learning that can be used with the present disclosure include, without limitation, linear discriminant analysis, analysis of variance, regression analysis, logistic regression, and probit regression, to name a few. A skilled artisan will recognize that many other machine learning algorithms can be used to determine the weight vector without departing from the scope of the present disclosure.

The training data, described above, include empirical data collected from multiple fall and non-fall scenarios which can be used to identify the predictive indicators of patient falls. Illustratively, for each training scenario, the five features described above with respect to block 1206 are determined and provided as input to the machine learning system. Additionally, an output is provided for each training scenario that identifies whether the scenario describes a falling event or a non-falling event. The machine learning system analyzes the training data to derive a rule that maps the inputs to the outputs. According to certain embodiments of the present disclosure, the output of the machine learning system is five-dimensional weight vector that weights each of the five features according to their relative value in determining whether or not a fall has occurred. The weight vector is determined off-line and is provided as a fixed, five-dimensional vector to the method 1200. Of course, the weight vector can be updated, based on analysis of additional empirical data.

The inner product (also referred to as the "dot product" and the "scalar product") of the received five-dimensional feature vector and the weight vector is calculated in a manner well understood by skilled artisans. The inner product yields a scaler value, also referred to herein as an activation value, that may be either positive or negative. At block 1210, the method 1200 determines whether a fall has been detected. According to some embodiments, the sign of the inner product of the received five-dimensional feature vector and the weight vector indicates whether a fall has occurred. If the inner product is less than zero, then no fall has been detected, and the method returns to block 1202 to begin analyzing the next set of data from the wireless sensor 102. If the inner product is greater than zero, then a fall has been detected and the method 1200 progresses to block 1214, where a notification, alarm, and/or alert indicating that the patient has fallen is transmitted to, for example, clinician devices 114, nurses' station systems 113, multi-patient monitoring system 110, and the like. The method returns to block 1202 to begin analyzing the next set of data from the wireless sensor 102.

In some embodiments, the system can determine a spatial location of the patient within the patient's room. The system can monitor the room and spatially monitor and/or calculate how long the patient has been in a position, when the patient was in the position, and/or how long the patient was in the position, among other parameters. As discussed above, the system uses, among other things, information sensed by the accelerometer 210 and by the gyroscope 212 of the wireless sensor 102 to track the patient. This method can be performed by the wireless sensor 102, using its processor 202 and storage device 204, or it can be performed by an external processing device that receives the sensed information from the wireless sensor 102, such as, for example, the patient monitor 106.

In some embodiments, the system can determine the position of the patient within the patient's room, relative to certain features of the patient's room, such as the patient's bed, a bathroom, a monitor, a doorway, and/or a window, among other room feature. In particular, using methods described herein, the system can determine a patient's vertical position, vertical displacement, horizontal position, horizontal displacement, angular position and/or angular displacement in the patient's room. For example, the accelerometer 210 and/or the gyroscope 212 can monitor the patient's movements as the patient walks throughout the patient's room. The system can determine whether the patient is falling, getting out of bed, or otherwise moving in a prohibited manner or in a manner that requires caregiver attention.

According to some embodiments, measurements from the accelerometer 210 and the gyroscope 212 of the wireless sensor 102 are used, among other things, to determine whether the patient is bending down and/or has fallen and/or where the patient has fallen (for example, by measuring the vertical displacement of the patient and/or the height of the patient relative to the floor). In some embodiments in which the patient has fallen, the clinician can determine the location of the fall according to an embodiment of the present disclosure. As discussed above, the accelerometer 210 measures linear acceleration of the patient with respect to gravity in three axes. The three axes of the accelerometer 210 are represented in fixed, inertial references. The gyroscope 212 provides outputs responsive to sensed angular velocity of the wireless sensor 102, as positioned on the patient, in three orthogonal axes corresponding to measurements of pitch, yaw, and roll. Based on these measurements, the system can determine whether the patient has fallen according to methods described herein.

In such configurations, the system can record the position of the patient. In certain aspects, the information received from the wireless sensor 102 can be used to create a time-sequenced representation of the patient's movement. This representation can be displayed on the display 120 or transmitted to a nurses' station or other processing node to enable the caregiver to monitor the patient. The time-sequenced representation can be viewed in real time and/or be recorded for playback. For example, if an alarm alerts the caregiver that the patient has fallen, the caregiver can access and review the historical sequence of the patient's movements prior to and during that period of time.

FIGS. 15A-H illustrate various configurations of a room display displayed on the patient display monitor. As illustrated in FIGS. 15A-H, the caregiver and/or patient can select any number of room items and/or configurations of the room items. The caregiver can select a room item, and place it within the room on the room display. The caregiver can rotate and/or place the room item in any configuration. In an embodiment, the caregiver could select the location of a major element of a room at a time. For example, the caregiver could select a position of the bed, then a position of the bathroom, then a position of the door, equipment, tables, chairs, couches, etc. In other embodiments, various room layout approximation are some to fully presented in selection screens and the determination of layout is made in one or just a few caregiver selections.

Figure 16:
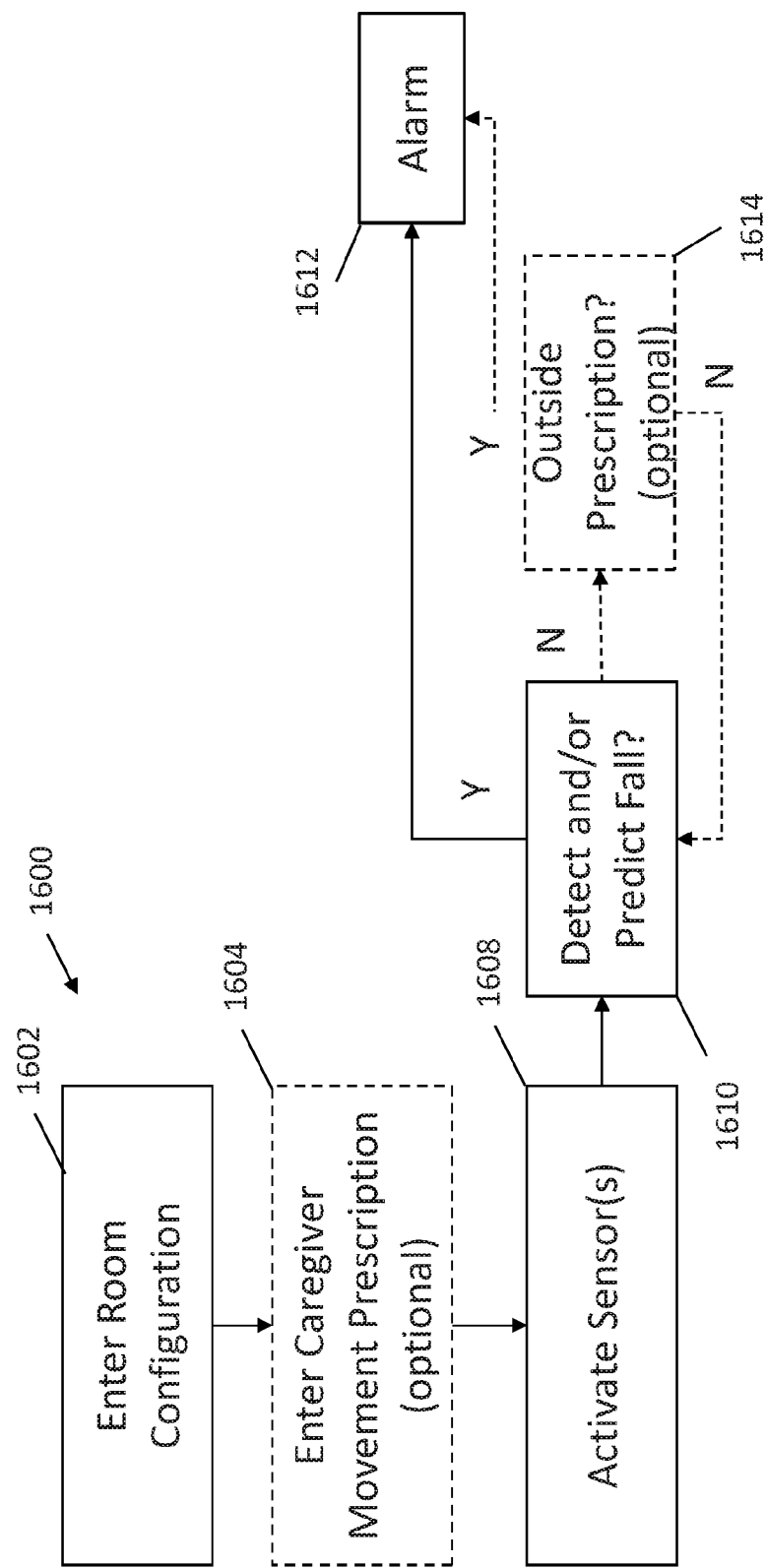
FIG. 16 illustrates an example method according to an embodiment of the present disclosure.

FIG. 16 illustrates an example method 1600 for detecting and/or predicting a patient's fall, determining a particular location of a patient within a patient's room, and/or determining whether the patient has moved outside of a prescribed movement of the patient, among others, for example.

At block 1602, the caregiver can enter a room configuration. For example, the caregiver can select any number of room items to be displayed in any number of configurations within a patient room display. The room items can include a patient's bed, a bathroom, a monitor, a doorway, and/or a window, among other room items. The caregiver can select a room item by selecting, dragging, and/or dropping each room item around the room display. In some embodiments, the caregiver can select a certain size for each room item. In some embodiments, the caregiver can simply select a room item and select the location within the room display for the room item to be oriented and displayed. In some embodiments, the room item can be snapped into place in the room display.

At block 1604, the caregiver can optionally enter a movement prescription. For example, the caregiver can enter instructions to the patient, including instructions to remain in bed, and/or to walk to the bathroom only with the assistance of an attendant.

At block 1608, one or more of the sensors described herein can be activated. In some examples, the caregiver manually activates the one or more sensors. In some examples, the system activates the one or more sensors automatically to begin tracking, monitoring, measuring, and/or calculating certain physiological parameters, according to methods described herein.

At block 1610, the patient monitoring system 100 can predict and/or detect a patient's fall and/or risk of falling based on analysis of the patient's movement (e.g., gait) and other information (such as, for example, the patient's current medication regimen). At block 1612, when the patient monitor 106 determines that the patient's risk of falling is above a predetermined threshold, the patient monitor 106 can issue an alarm or alert to notify care providers of the identified risk in an effort to anticipate and therefore prevent a patient fall. Additionally, the patient monitor 106 can determine when a patient has fallen and issue the appropriate alarms and alerts to summon care provider assistance. The alert system can alert the caregiver that the patient is falling, getting out of bed, or otherwise moving in a prohibited manner or in a manner that requires caregiver attention. The alert can be an audible and/or visual alarm on the monitoring system or transmitted to a caregiver (e.g., nurses' station system 113, clinician device 114, pager, cell phone, computer, or otherwise).

If the patient monitoring system has not detected a patient's fall, the patient monitoring system 100 can optionally determine whether the patient has moved outside of the movement prescription. For example, as described above, the patient monitor 106 can determine the mobility status of the patient, e.g., whether the patient is ambulatory, standing, sitting, reclining, or falling.

If the patient monitoring system 100 determines that the patient has contravened a caregiver's order, such as, for example, instructions to remain in bed, or to walk to the bathroom only with the assistance of an attendant, a notification, alert, or alarm can be transmitted to the appropriate caregivers at block 1612.

If the patient monitoring system 100 determines that the patient has not contravened a caregiver's order, the system will return to block 1610 to detect and/or predict whether the patient has fallen.

FIGS. 13A-F illustrate embodiments of icon displays reflecting a patient's position according to an embodiment of the present disclosure. According to some embodiments, the graphical icons are used to visually depict the detected orientation of the patient. In particular, the icons of FIGS. 13A-F show, in stick figure-type format, the patient sitting, standing, and lying in the supine position (on the back), the prone position (on the belly), on the left side, and on the right side, respectively.

Figure 14:
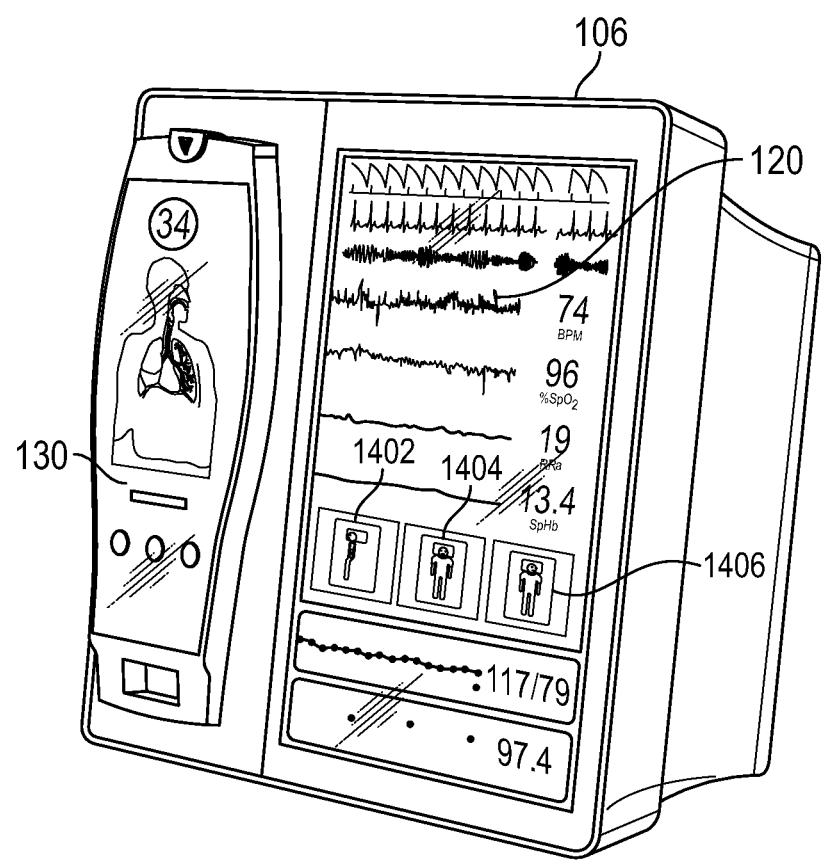
FIG. 14 illustrates an example display of a patient monitor incorporating the icons illustrated in FIGS. 13A-F according to an embodiment of the present disclosure.'
Figure 15A:
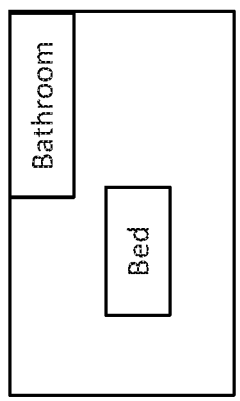
FIGS. 15A-15H illustrate various configurations of a room display displayed on a patient display monitor according to an embodiment of the present disclosure.
Figure 15B:
Figure 15C:
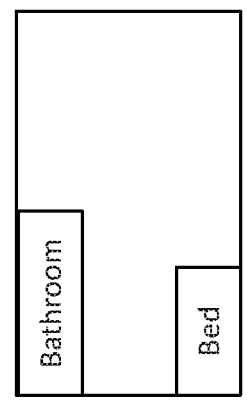
Figure 15D:
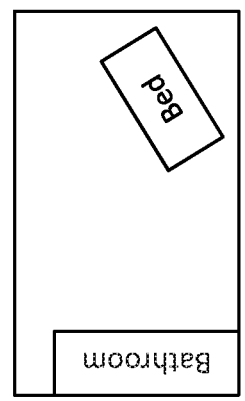
Figure 15E:
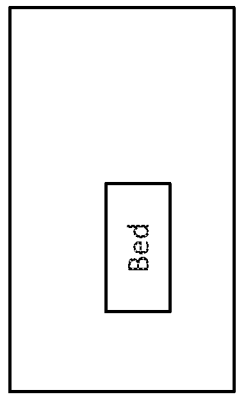
Figure 15F:
Figure 15G:
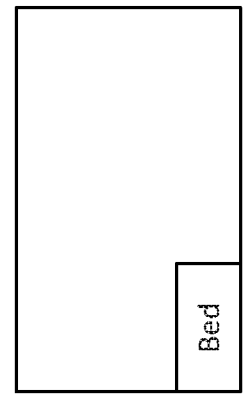
Figure 15H:
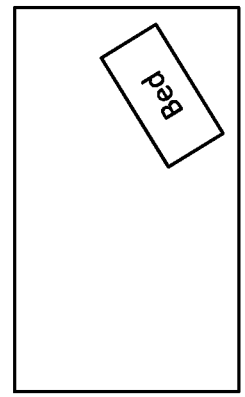

FIG. 14 illustrates an example of how the icons described with respect to FIGS. 13A-F can be presented on the display 120 of the patient monitor 106. Toward the bottom of the main display 120 are a set of 3 icons 1402, 1404, and 1406 indicating the patient's position. The left-most icon 1404 shows the patient lying on his right side. The two icons to the right of the left-most icon 1404 and 1406 show the patient lying on his back. According to certain embodiments, the display 120 of the patient monitor 106 can include a touchscreen interface. The touchscreen interface can enable finger controls, including a touch gesture, a touch and move gesture, and a flick gesture. Illustratively, a clinician may use the touch gesture on an icon 1406 to expand the icon in the display 120 to include additional information associated with that icon 1406. For example, additional information associated with the "touched" icon 1406 can include, the time at which the patient assumed the particular orientation, the time (if available) at which the patient moved from the orientation, the total duration of time the patient spent in the particular orientation, the number if discrete times that the patient has been in the particular orientation over a defined period (such as 24 hours), the total duration of time that the patient the patient has been in the particular orientation over a defined period (such as 24 hours), and the like. The clinician may also use the flick finger gesture to scroll right and left, corresponding to moving forward and backward in time, to access the historical positional record of the patient.

The service life of the wireless sensor 102 disclosed herein can vary depending on, among other things, battery size, and data transmission characteristics such as data rate, frequency of transmission, and quantity of data transmitted. According to one embodiment, the wireless sensor 102 is configured to operate continuously or near continuously (e.g., waking up every second or so to sense and transmit the patient's physiological data) for approximately two days, after which the wireless sensor 102 is to be disposed of properly. Other embodiments of the wireless sensor 102, equipped with a larger battery, for example, are configured to operate for longer periods of time before disposal. Some embodiments can be configured for sterilization and reuse.

Certain medical device manufacturers implement quality control measures for disposable medical devices, such as embodiments of the disclosed wireless sensor 102, to carefully control and manage the performance characteristics of their disposable devices. In particular, there is a risk that used and disposed-of wireless sensors 102 can be salvaged and refurbished or retrofitted for additional use beyond the defined and intended service life of the wireless sensor 102. Features can be included in the disclosed patient monitoring system 100 to help prevent improper use of the wireless sensor 102 beyond its defined service life.

According to one embodiment of the patient monitoring system 100, the wireless sensor 102 is configured to set an activation flag in the storage device 204 of the wireless sensor 102 upon initial activation, indicating that the wireless sensor 102 has been activated for use. In some embodiments, the activation flag is set in an information element 215 which is provided to store information about the usage of the wireless sensor 102 to help maintain quality control. Advantageously, the activation flag is set in nonvolatile memory of the storage device 204, or in the information element 215, so that disconnection from the battery 214 will not disrupt or erase the set activation flag. Thus, if the wireless sensor 102 is reconditioned such that it may be activated a second time, the activation flag will indicate, through a standard sensor 102 start-up routine, that the sensor 102 has been previously activated. Upon detection of the activation flag, the wireless sensor 102 can transmit a prior activation message and/or alert which can serve as a warning notification that the quality of the sensor 102 may be compromised. The transmitted warning or alert can be received by, for example, a patient monitor 106 which can then provide a menu of actions that the user may take in response to the transmitted quality warning or alert. The menu of actions can include the option to shut down the wireless sensor 102. In certain situations it may be desirable to continue to use the wireless sensor 102. Illustratively, it is possible that the battery 214 connection to the wireless sensor 102 is established and then unintentionally disconnected. For example, a battery isolator 322 may be initially removed from the sensor 102 but then re-inserted so as to once again isolate the battery 214 from the electronic circuitry of the wireless sensor 102. Removing the battery isolator 322 a second time will result in transmission of a quality warning or alert as described above. In such a situation the user, being aware of the circumstances that led to the quality warning, may choose to continue to use the wireless sensor 102.

According to another embodiment, the wireless sensor 102 is configured to set a prolonged service flag, after the wireless sensor has been in an activated state for a predefined period of time, such as, for example, four hours. The prolonged service flag can serve to indicate upon start-up that the sensor 102 has previously been active for a prolonged duration of time. In another embodiment, the wireless sensor 102 tracks and records on the storage device 204 the duration of time that the sensor 102 has been active. Advantageously, the sensor 102 can issue notifications and/or alerts to the user that the sensor 102 is nearing the end of service life, providing the user an opportunity to take steps to replace the wireless sensor 102 before it ceases to operate. Additionally, the recorded duration of time that the sensor 102 has been active can serve to detect when a sensor 102 has been refurbished to operate beyond its intended service life. The appropriate warning can then be transmitted to the user. According to some embodiments, once the wireless sensor has been active for a period of time equal to a maximum service life duration, the sensor 102 sets a flag in the storage device 204, or otherwise configures itself to prohibit the sensor 102 from operating further.

In other embodiments, the wireless sensor 102 transmits to the patient monitor 106 a unique identifier such as, for example, a product serial number that is encoded in one of the hardware components of the wireless sensor 102. Once the wireless sensor 102 is paired with a patient monitor or with an expander/repeater 107 and is operational, the patient monitor 106 or the expander/repeater 107 can transmit the sensor's 102 unique identifier to a central repository that lists the unique identifiers of sensors 102 known to have been operational. Illustratively, during the pairing operation, the patient monitor 106 or the expander/repeater 107 can check the central repository to determine whether the wireless sensor 102 that is attempting to pair has been listed on in the central repository, thereby indicating that the wireless sensor 102 might have quality issues.

In other various embodiments, the wireless sensor 102 includes a sensor information element 215, which can be provided through an active circuit such as a transistor network, memory chip, EEPROM (electronically erasable programmable read-only memory), EPROM (erasable programmable read-only memory), or other identification device, such as multi-contact single wire memory devices or other devices, such as those commercially available from Dallas Semiconductor or the like. The sensor information element 215 may advantageously store some or all of a wide variety of information, including, for example, sensor type designation, sensor configuration, patient information, sensor characteristics, software such as scripts or executable code, algorithm upgrade information, software or firmware version information, or many other types of data. In a preferred embodiment, the sensor information element 215 may also store useful life data indicating whether some or all of the sensor components have expired.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the systems, devices or methods illustrated can be made without departing from the spirit of the disclosure. As will be recognized, certain embodiments described herein can be embodied within a form that does not provide all of the features and benefits set forth herein, as some features can be used or practiced separately from others.

The term "and/or" herein has its broadest, least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Although the foregoing disclosure has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the description of the preferred embodiments, but is to be defined by reference to claims.

What is claimed is:

1. A wearable wireless sensor for monitoring a thermal energy of a patient and at least one of pressure ulcer risk, fall detection, or fall risk, said wearable wireless sensor comprising:
    a housing including a predetermined position for at least a first sensor and a second sensor,
    one or more accelerometers responsive to an acceleration of said patient and configured to output one or more signals indicative of at least one of said pressure ulcer risk, said fall detection, or said fall risk;
    a base including a first aperture;
    a circuit layer including a first through-hole via extending through said circuit layer; and
    a temperature sensor responsive to said thermal energy of said patient, said temperature sensor mounted on said circuit layer, said temperature sensor including a thermal contact in thermal communication with said circuit layer, wherein said temperature sensor is at least one of the first sensor or the second sensor;
    wherein said first through-hole via is aligned with said thermal contact of said temperature sensor and with said first aperture of said base, said first through-hole via is configured to provide a structure to transmit said thermal energy across a length of the first through-hole via from said patient to said temperature sensor,
    wherein said first aperture and said first through-hole via include a thermally conductive material to cause said temperature sensor to be in thermal communication with a portion of said base corresponding to said first aperture, and
    wherein the housing is configured to operably position the base and the circuit layer.

2. The wearable wireless sensor of claim 1, wherein said base insulates a portion of a patient's body surrounding said portion of said base corresponding to said first aperture.

3. The wearable wireless sensor of claim 1, further comprising:
    a second aperture in said base;
    a second through-hole via extending through said circuit layer between said top side and bottom side of said circuit layer;
    an electrocardiogram (ECG) sensor mounted on said circuit layer, said ECG sensor responsive to electrical signals, said ECG sensor including an extendible lead with an electrode responsive to said electrical signals, said ECG lead also including an electrical contact in electrical communication with said circuit layer,
    wherein said second through-hole via is aligned with said electrical contact of said ECG sensor on said circuit layer and with said second aperture of said base, and
    wherein said second aperture of said base and said second through-hole via of said circuit layer include an electrically conductive material, said ECG sensor in electrical communication with a portion of said base corresponding to said second aperture through said conductive material.

4. The wearable wireless sensor of claim 1, wherein said one or more accelerometers are mounted on said circuit layer, said one or more accelerometers responsive to acceleration of said patient, said wearable wireless sensor further comprising:
    a third aperture in said base; and
    an acoustic respiration sensor responsive to vibrational motion of said patient, said acoustic respiration sensor being disposed on said circuit layer and extending through said third aperture in said base, wherein said acoustic respiration sensor is rigidly secured to said circuit layer so as to mechanically transmit sensed vibrational motion to said one or more accelerometers.

5. The wearable wireless sensor of claim 1, further comprising a gyroscope mounted on said circuit layer, said gyroscope responsive to an angular velocity of said patient.

6. The wearable wireless sensor of claim 5, wherein said one or more accelerometers comprises a three-dimensional accelerometer and said gyroscope comprises a three-dimensional gyroscope.

7. The wearable wireless sensor of claim 6, further comprising non-volatile memory configured to store information indicative of whether said wearable wireless sensor has been previously activated.

8. The wearable wireless sensor of claim 1, wherein the second sensor is said one or more accelerometers.

9. The wearable wireless sensor of claim 1, wherein the housing includes a predetermined position for at least a third sensor.

10. The wearable wireless sensor of claim 8, wherein the housing includes a predetermined position for at least a fourth sensor.

11. The wearable wireless sensor of claim 10, wherein the third and fourth sensors include one or more of an acoustic sensor, an electrocardiogram sensor, a respiration sensor, a heart rate sensor, and a blood oxygen sensor.

* * * * *